(12) United States Patent
Porter et al.

(10) Patent No.: US 8,690,815 B2
(45) Date of Patent: Apr. 8, 2014

(54) DEVICE AND METHOD FOR VASCULAR ACCESS

(75) Inventors: Christopher H. Porter, Woodinville, WA (US); Laurie E. Lynch, Eden Prairie, MN (US); Judson A. Herrig, Elko, MN (US); Robert J. Ziebol, Blaine, MN (US)

(73) Assignee: Hemosphere, Inc., Kennesaw, GA (US)

( * ) Notice: Subject to any disclaimer, the term of this patent is extended or adjusted under 35 U.S.C. 154(b) by 278 days.

(21) Appl. No.: 12/831,092

(22) Filed: Jul. 6, 2010

(65) Prior Publication Data

US 2011/0060264 A1 Mar. 10, 2011

Related U.S. Application Data

(63) Continuation of application No. 11/216,536, filed on Aug. 31, 2005, now Pat. No. 7,762,977, which is a continuation-in-part of application No. 10/962,200, filed on Oct. 8, 2004, now abandoned.

(60) Provisional application No. 60/509,428, filed on Oct. 8, 2003, provisional application No. 60/605,681, filed on Aug. 31, 2004.

(51) Int. Cl.
*A61M 37/00* (2006.01)
*A61M 31/00* (2006.01)

(52) U.S. Cl.
USPC ............... 604/6.16; 604/507; 604/508; 604/8

(58) Field of Classification Search
USPC .............................. 604/6.16, 8, 507, 508, 533
See application file for complete search history.

(56) References Cited

U.S. PATENT DOCUMENTS

| | | | |
|---|---|---|---|
| 3,363,926 A | | 1/1968 | Wilson |
| 3,490,438 A | | 1/1970 | Lavender et al. |
| 3,683,926 A | * | 8/1972 | Suzuki .......................... 606/154 |
| 3,814,137 A | | 6/1974 | Martinez |
| 3,818,511 A | | 6/1974 | Goldberg |
| 3,826,257 A | | 7/1974 | Buselmeier |
| 3,882,862 A | | 5/1975 | Berend |
| 3,998,222 A | * | 12/1976 | Shihata ............................ 604/9 |

(Continued)

FOREIGN PATENT DOCUMENTS

| | | |
|---|---|---|
| DE | 4418910 A1 | 12/1995 |
| DE | 29515546 U1 | 1/1997 |

(Continued)

OTHER PUBLICATIONS

European Search Report dated Dec. 3, 2013.

*Primary Examiner* — Leslie Deak
(74) *Attorney, Agent, or Firm* — Sutherland Asbill & Brennan LLP

(57) ABSTRACT

Vascular access systems for performing hemodialysis are disclosed. The vascular access system contemplates a catheter section adapted for insertion into a vein and a graft section adapted for attachment to an artery. The catheter section may have metal or polymer wall reinforcements that allow the use of thin-walled, small outer diameter conduits for the vascular access system. One or more of the adhered, embedded or bonded conduit reinforcement structures may be removable without significant damage to the conduit sections to facilitate attachment of the sections, or to a connector between the sections. Various self-sealing materials are provided for use in the vascular access system, as well as temporary access sites and flow control/sensor systems.

20 Claims, 36 Drawing Sheets

(56) References Cited

U.S. PATENT DOCUMENTS

| | | |
|---|---|---|
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmerman |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler et al. |
| 4,619,641 A | 10/1986 | Schanzer |
| 4,655,771 A | 4/1987 | Wallsten |
| 4,723,948 A * | 2/1988 | Clark et al. ............. 604/533 |
| 4,734,094 A | 3/1988 | Jacob et al. |
| 4,753,236 A | 6/1988 | Healey |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,856,938 A | 8/1989 | Kuehn |
| 4,877,661 A | 10/1989 | House et al. |
| 4,898,669 A | 2/1990 | Tesio |
| 4,917,067 A | 4/1990 | Yoshida |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,330,500 A | 7/1994 | Song |
| 5,399,168 A | 3/1995 | Wadsworth et al. |
| 5,405,320 A | 4/1995 | Twardowski et al. |
| 5,405,339 A | 4/1995 | Kohnen et al. |
| 5,454,790 A | 10/1995 | Dubrul |
| 5,476,451 A | 12/1995 | Ensminger et al. |
| 5,496,294 A | 3/1996 | Hergenrother et al. |
| 5,509,897 A | 4/1996 | Twardowski et al. |
| 5,558,641 A | 9/1996 | Glantz et al. |
| 5,562,617 A | 10/1996 | Finch et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,631,748 A | 5/1997 | Harrington |
| 5,637,088 A | 6/1997 | Wenner |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Evans et al. |
| 5,755,775 A | 5/1998 | Trerotola et al. |
| 5,792,104 A | 8/1998 | Speckman et al. |
| 5,797,879 A | 8/1998 | DeCampli |
| 5,800,512 A | 9/1998 | Lentz et al. |
| 5,800,514 A | 9/1998 | Nunez et al. |
| 5,800,522 A | 9/1998 | Campbell et al. |
| 5,810,870 A | 9/1998 | Myers et al. |
| 5,829,487 A | 11/1998 | Thomas et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi et al. |
| 6,001,125 A | 12/1999 | Golds et al. |
| 6,019,788 A | 2/2000 | Butters et al. |
| 6,036,724 A | 3/2000 | Lentz et al. |
| 6,102,884 A * | 8/2000 | Squitieri ............... 604/8 |
| 6,156,016 A | 12/2000 | Maginot |
| 6,167,765 B1 * | 1/2001 | Weitzel ............. 73/861.18 |
| 6,171,295 B1 | 1/2001 | Garabedian et al. |
| 6,231,085 B1 | 5/2001 | Olson |
| 6,245,098 B1 | 6/2001 | Feeser et al. |
| 6,255,396 B1 | 7/2001 | Ding et al. |
| 6,261,255 B1 | 7/2001 | Mullis et al. |
| 6,261,257 B1 | 7/2001 | Uflacker |
| 6,319,279 B1 * | 11/2001 | Shannon et al. ........... 623/1.44 |
| 6,338,724 B1 | 1/2002 | Dossa |
| 6,398,764 B1 | 6/2002 | Finch et al. |
| 6,402,767 B1 | 6/2002 | Nash et al. |
| 6,428,571 B1 * | 8/2002 | Lentz et al. ............. 623/1.4 |
| 6,436,132 B1 | 8/2002 | Patel et al. |
| 6,536,135 B2 | 3/2003 | Lipkin |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda |
| 6,702,748 B1 | 3/2004 | Nita et al. |
| 6,702,781 B1 | 3/2004 | Reifart et al. |
| 6,706,025 B2 | 3/2004 | Engelson |
| 6,719,781 B1 | 4/2004 | Kim |
| 6,719,783 B2 | 4/2004 | Lentz et al. |
| 6,730,096 B2 | 5/2004 | Basta et al. |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway |
| 6,758,836 B2 | 7/2004 | Zawacki |
| 6,858,019 B2 | 2/2005 | McGuckin |
| 6,926,735 B2 | 8/2005 | Henderson |
| 6,976,952 B1 | 12/2005 | Maini |
| 7,011,645 B2 | 3/2006 | McGuckin |
| 7,025,741 B2 | 4/2006 | Cull |
| 7,036,599 B2 | 5/2006 | Matteucci |
| 7,101,356 B2 | 9/2006 | Miller |
| 7,131,959 B2 | 11/2006 | Blatter |
| 7,211,074 B2 | 5/2007 | Sansoucy |
| 7,252,649 B2 | 8/2007 | Sherry |
| 7,297,158 B2 | 11/2007 | Jensen |
| 7,399,296 B2 | 7/2008 | Poole |
| 7,507,229 B2 | 3/2009 | Hewitt |
| 7,722,665 B2 | 5/2010 | Anwar |
| RE41,448 E | 7/2010 | Squitieri |
| 7,789,908 B2 | 9/2010 | Sowinski et al. |
| 7,828,833 B2 | 11/2010 | Haverkost et al. |
| 7,850,675 B2 | 12/2010 | Bell et al. |
| 8,097,311 B2 | 1/2012 | Wang |
| 2002/0049403 A1 | 4/2002 | Alanis |
| 2003/0100859 A1 | 5/2003 | Henderson et al. |
| 2005/0137614 A1 | 6/2005 | Porter et al. |
| 2005/0215938 A1 | 9/2005 | Khan et al. |
| 2006/0058867 A1 | 3/2006 | Thistle et al. |
| 2006/0118236 A1 | 6/2006 | House |

FOREIGN PATENT DOCUMENTS

| | | |
|---|---|---|
| JP | 57-14358 | 1/1982 |
| JP | 62-112567 | 5/1987 |
| JP | 05-212107 | 8/1993 |
| JP | 06-105798 | 4/1994 |

(56) References Cited

FOREIGN PATENT DOCUMENTS

| | | |
|---|---|---|
| JP | 09-84871 | 3/1997 |
| WO | 9519200 A1 | 7/1995 |
| WO | 9624399 A1 | 8/1996 |
| WO | WO9834676 | 8/1998 |
| WO | 0076577 A1 | 12/2000 |
| WO | 0105463 A1 | 1/2001 |
| WO | WO0128456 | 4/2001 |
| WO | 2004112880 A1 | 12/2004 |

* cited by examiner

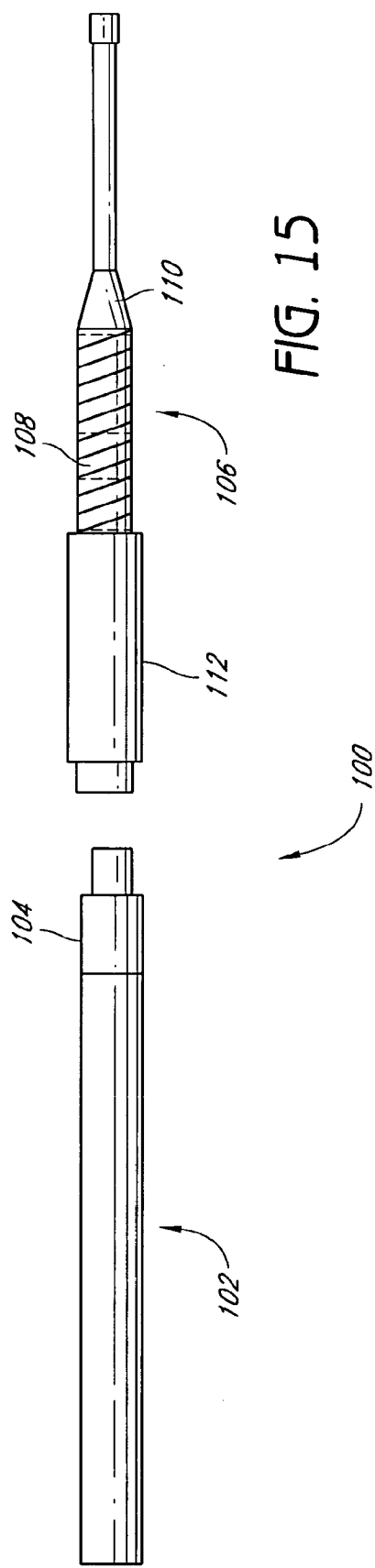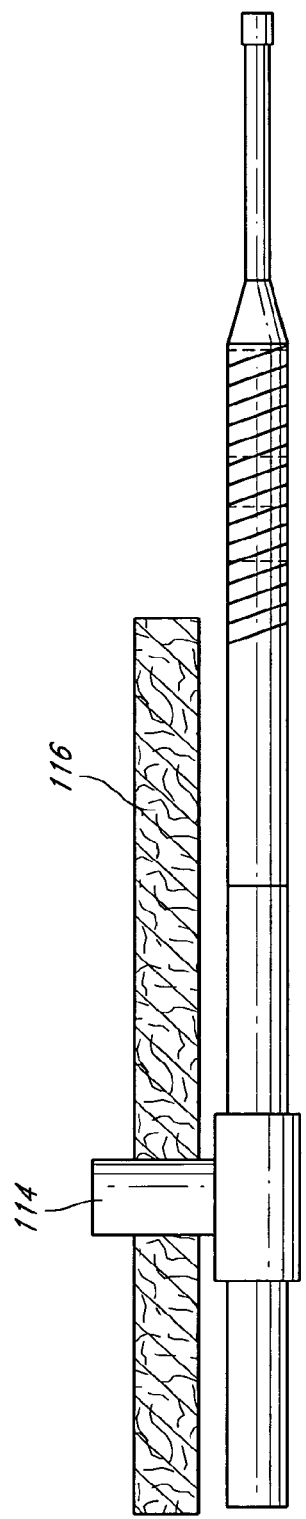

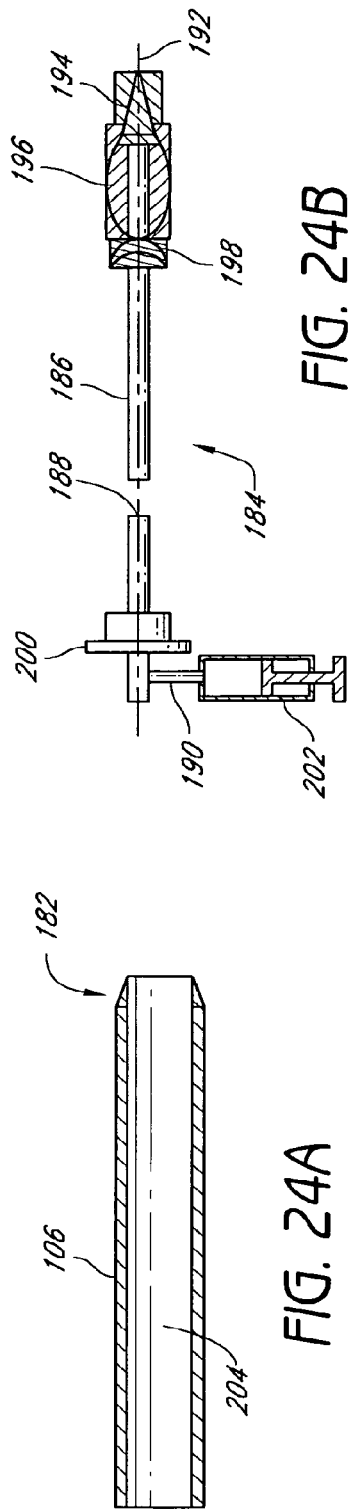
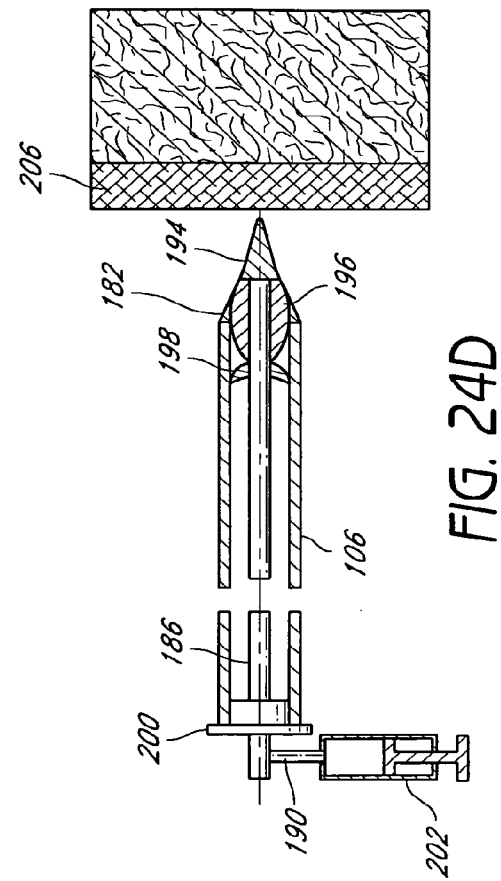
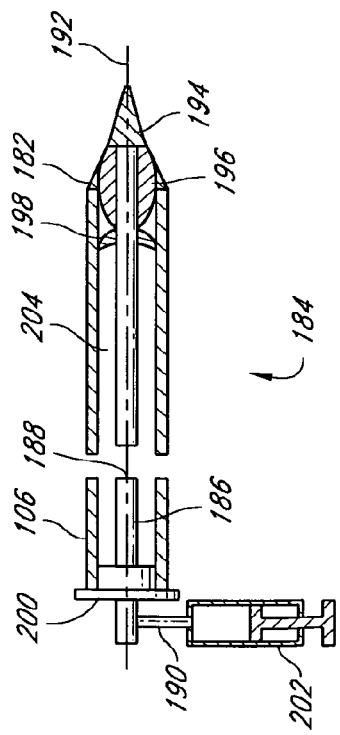
FIG. 24A
FIG. 24B
FIG. 24C
FIG. 24D

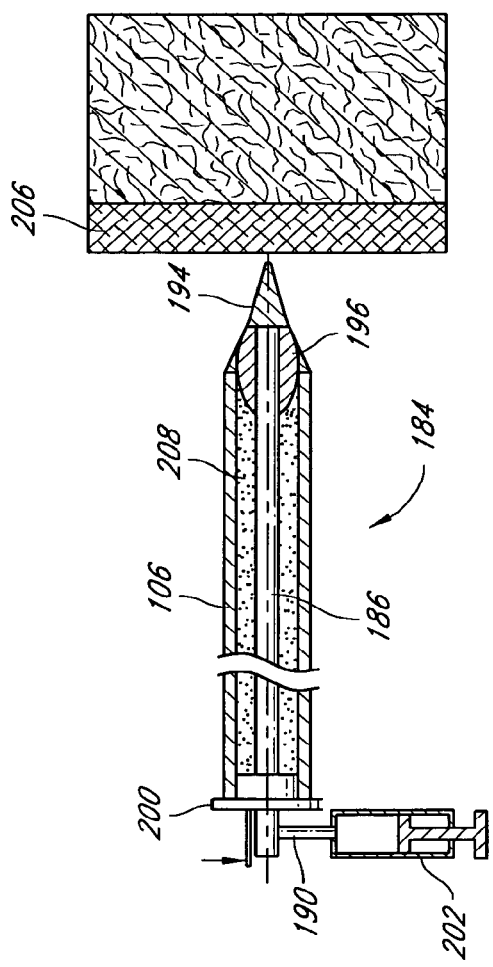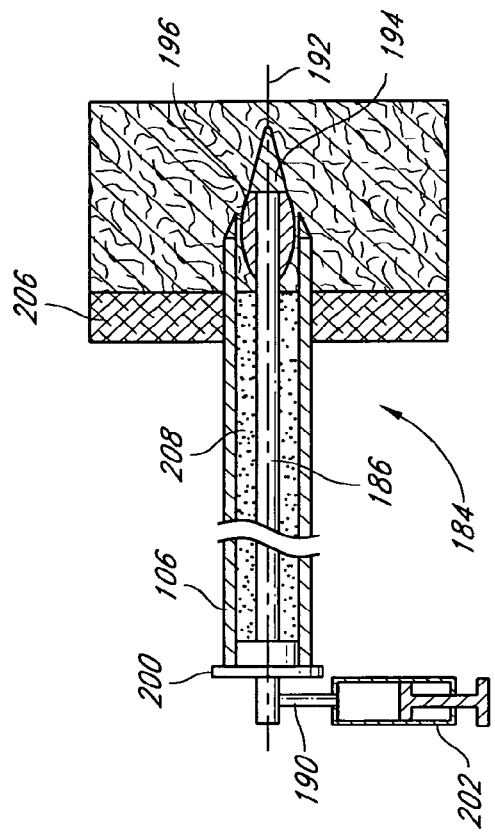

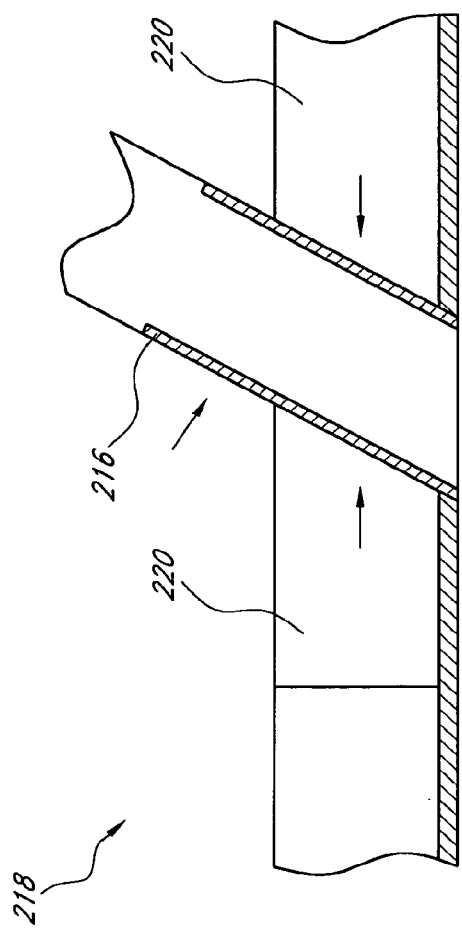
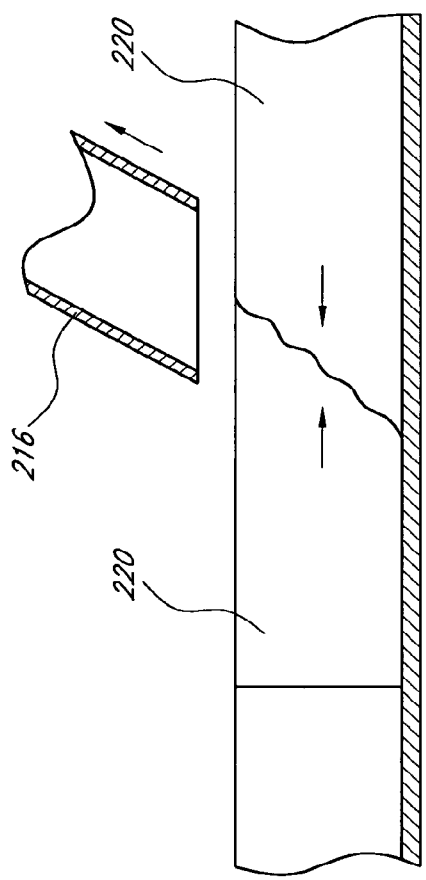
FIG. 27A
FIG. 27B

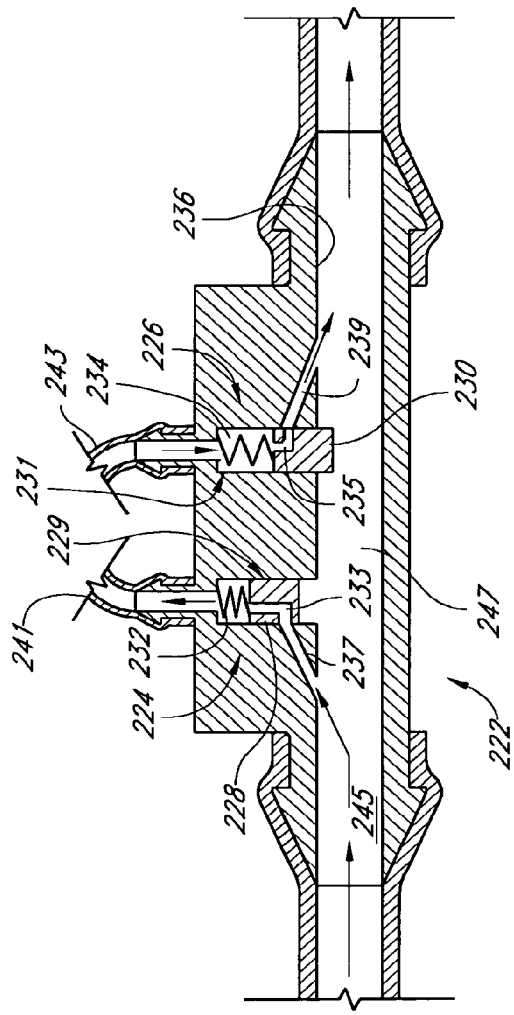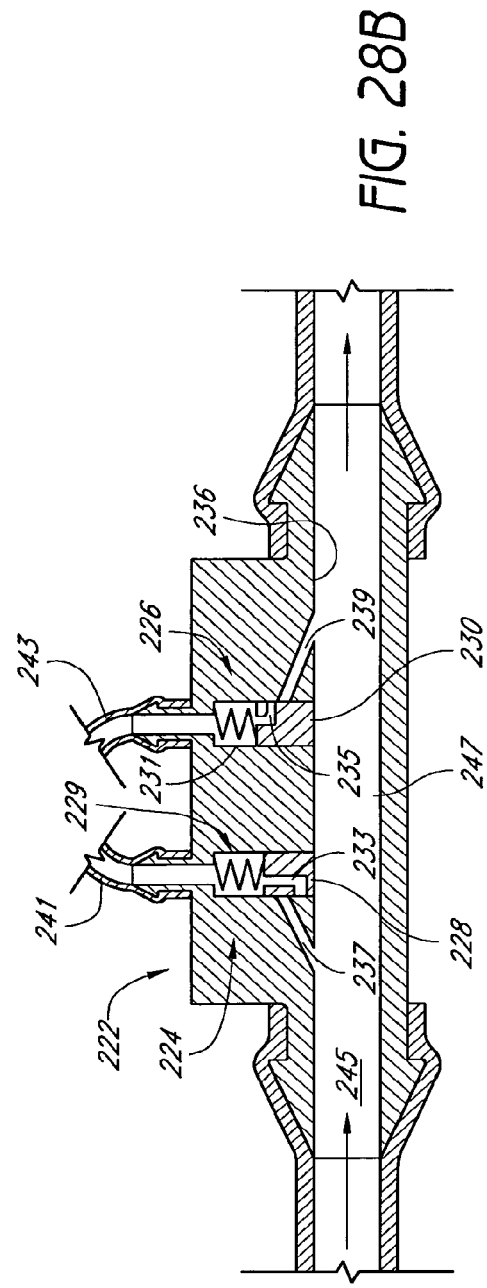

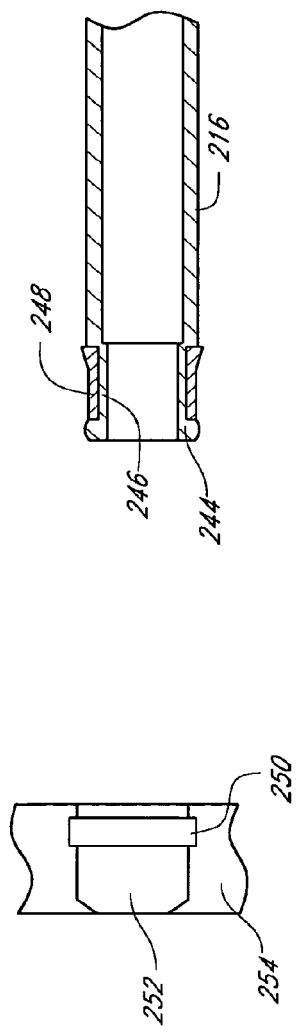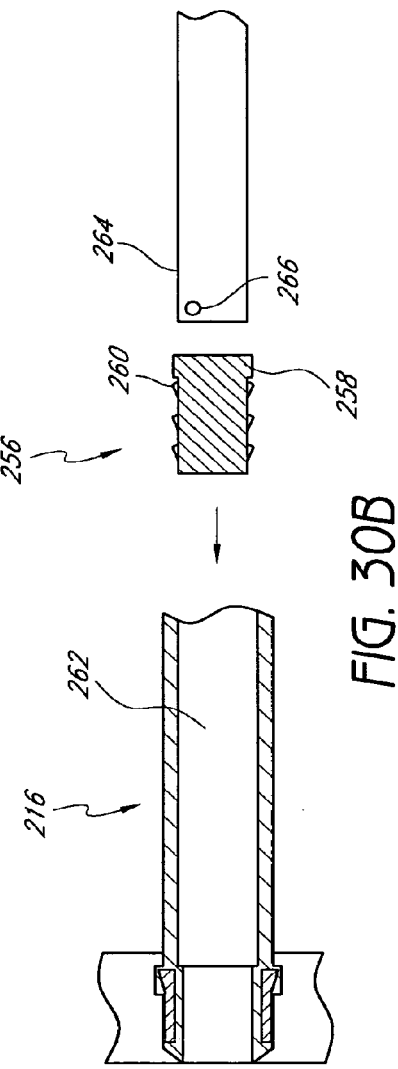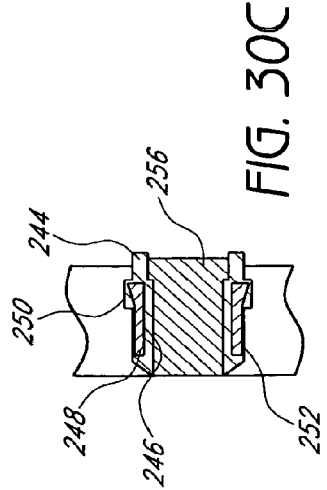
FIG. 30A
FIG. 30B
FIG. 30C

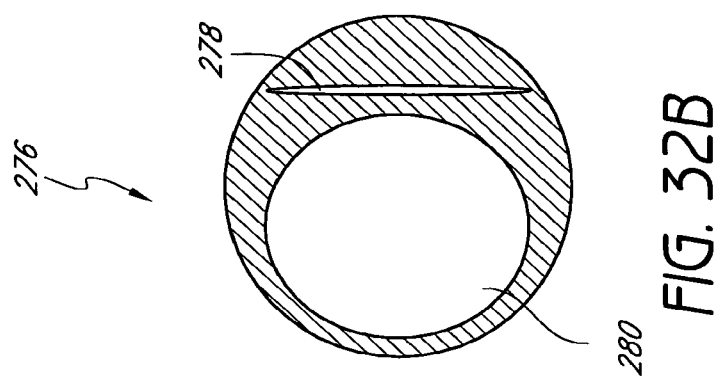
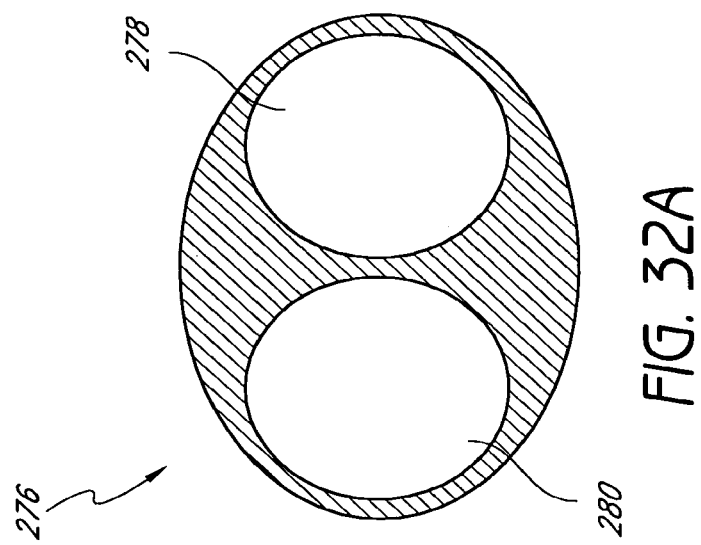

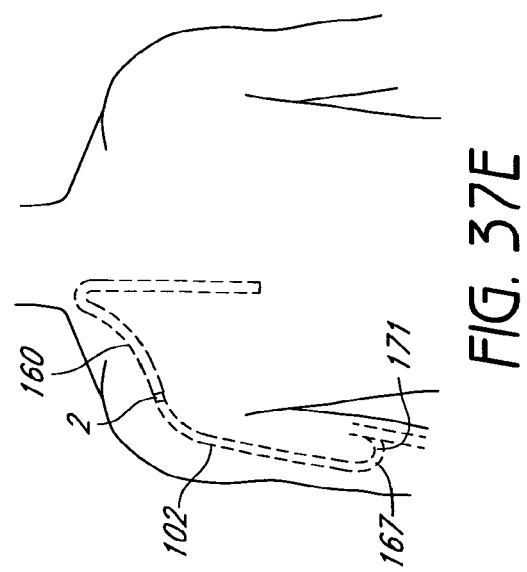

DEVICE AND METHOD FOR VASCULAR ACCESS

CROSS-REFERENCE TO RELATED APPLICATIONS

The present application is a continuation of U.S. application Ser. No. 11/216,536 filed on Aug. 31, 2005, which is a continuation-in-part of U.S. application Ser. No. 10/962,200 filed on Oct. 8, 2004, which claims priority under 35 U.S.C. §119(e) to U.S. Provisional Application No. 60/509,428 filed on Oct. 8, 2003, and to U.S. Provisional Application No. 60/605,681 filed on Aug. 31, 2004, the disclosures of which are incorporated by reference herein in their entirety.

BACKGROUND OF THE INVENTION

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take 6 to 8 weeks before the venous section of the fistula has sufficiently matured to provide adequate blood flow for use with hemodialysis. Moreover, a direct anastomosis may not be feasible in all patients due to anatomical considerations. Other patients may require the use of artificial graft material to provide an access site between the arterial and venous vascular systems. Although many materials that have been used to create prosthetic grafts for arterial replacement have also been tried for dialysis access, expanded polytetrafluoroethylene (ePTFE) is the preferred material. The reasons for this include its ease of needle puncture and particularly low complication rates (pseudo-aneurysm, infection, and thrombosis). However, AV grafts still require time for the graft material to mature prior to use, so that a temporary access device, such as a Quinton catheter, must be inserted into a patient for hemodialysis access until the AV graft has matured. The use of temporary catheter access exposes the patient to additional risk of bleeding and infection, as well as discomfort. Also, patency rates of ePTFE access grafts are still not satisfactory, as the overall graft failure rate remains high. Sixty percent of these grafts fail yearly, usually due to stenosis at the venous end. (See Besarab, A & Samararpungavan D., "Measuring the Adequacy of Hemodialysis Access". *Curr Opin Nephrol Hypertens* 5(6) 527-531, 1996, Raju, S. "PTFE Grafts for Hemodialysis Access". *Ann Surg* 206(5), 666-673, November 1987, Koo Seen Lin, L C & Burnapp, L. "Contemporary Vascular Access Surgery for Chronic Hemodialysis". *J R Coll Surg* 41, 164-169, 1996, and Kumpe, D A & Cohen, M A H "Angioplasty/Thrombolytic Treatment of Failing and Failed Hemodialysis Access Sites: Comparison with Surgical Treatment". *Prog Cardiovasc Dis* 34(4), 263-278, 1992, all herein incorporated by reference in their entirety). These failure rates are further increased in higher-risk patients, such as diabetics. These access failures result in disruption in the routine dialysis schedule and create hospital costs of over $2 billion per year. (See Sharafuddin, M J A, Kadir, S., et al. "Percutaneous Balloon-assisted aspiration thrombectomy of clotted Hemodialysis access Grafts". *J Vasc Interv Radiol* 7(2) 177-183, 1996, herein incorporated by reference in its entirety).

SUMMARY OF THE INVENTION

Vascular access systems for performing hemodialysis are disclosed. The vascular access system contemplates a catheter section adapted for insertion into a vein and a graft section adapted for attachment to an artery. The catheter section may have metal or polymer wall reinforcements that allow the use of thin-walled, small outer diameter conduits for the vascular access system. One or more of the adhered, embedded or bonded conduit reinforcement structures may be removable without significant damage to the conduit sections to facilitate attachment of the sections, or to a connector between the sections. Various self-sealing materials are provided for use in the vascular access system, as well as temporary access sites and flow control/sensor systems.

In one embodiment, an apparatus for providing needle access to a blood pathway is provided, comprising a graft conduit for attachment to an artery, a catheter conduit for insertion in a vein, and a self-sealing element, comprising a wall structure defining, at least in part, an internal passageway in fluid communication with said graft and catheter conduits so that, in use, said conduits and said passageway can form said blood pathway, said wall structure being formed of a tubular material that can be punctured by a needle to permit needle access to said passageway and re-seals upon withdrawal of said needle, wherein said self-sealing element may be formed a wall of the catheter conduit or located between the graft conduit and catheter conduit. The apparatus may be selected from the group consisting of material subject to compressive stress, material having a porous structure enhancing microthrombosis, low durometer materials, thixotropic materials and/or a gelatinous material. Said material may comprise at least two layers subject to compressive stress of different orientations. Said conduit connector may be pre-connected to the graft conduit at the point of manufacture. Said conduit connector may be integral with the graft conduit. The apparatus may further comprise a strain relief tube about the catheter conduit, said strain relief tube having a first end and a second end, the second end comprising two or more flexural sections and two or more separations between the flexural sections, a means for controlling blood flow rate through the blood pathway, and/or a means for monitoring blood flow rate through the blood pathway.

In one embodiment, an implantable graft for providing needle access to a blood pathway shortly after implantation is provided, said apparatus comprising an elongate, generally tubular body having a graft portion for attachment to an artery and a catheter portion having an end and being adapted for at least a section of said catheter portion to be inserted into a vein with said end distanced from the vein insertion location, a zone for repeated needle access formed of a generally tubular material which seals with respect to blood after withdrawal of the needle, said zone being formed in said catheter portion. Said catheter portion may have walls forming said tubular zone. Said zone may be an element connected between said catheter section and said graft portion. The implantable graft may comprise a connector joining said graft and catheter portions, reinforcement to reduce kinking in said graft portion, and/or reinforcement to reduce kinking in said catheter portion.

In one embodiment, an apparatus for providing needle access to a blood pathway is provided, comprising a graft conduit for attachment to an artery, a catheter conduit for insertion in a vein, and a self-sealing element, comprising a flexible wall structure defining, at least in part, a flexible internal passageway in fluid communication with said graft and catheter conduits so that, in use, said conduits and said flexible passageway can form said blood pathway, said wall structure being formed of a material that can be punctured by a needle to permit needle access to said passageway and re-seals upon withdrawal of said needle.

In one embodiment, an arteriovenous graft comprising a separate graft portion for attachment to an artery and attachable catheter portion for placement in a vein is provided, said graft portion and said catheter portion comprising a tubular structure having an internal passageway for conducting, in use, blood from said artery to said vein, and at least two lumens in fluid communication with said passageway and may further comprise a structure for interrupting said fluid communication to provide temporary access to said passageway. The means for interrupting said fluid communication may comprise a region of compressive material at the fluid communication between said tubular structure and said lumens, the compressive material biased to interrupt said fluid communication if said lumens are removed, at least one flap valve biased to interrupt the fluid communication between said tubular structure and said lumens, at least one mechanical valve biased to interrupt the fluid communication between said tubular structure and said lumens, and/or at least one lumen plug to interrupt the fluid communication between said tubular structure and said lumens. The at least one mechanical valve may be an at least one piston valve, an injectable lumen sealing compound to interrupt the fluid communication between said tubular structure and said lumens, and/or an at least one spring-biased piston valve. At least one lumen plug may be an at least one proximal lumen plug. The at least one lumen plug may be an at least one lumen plug with a locking stop. The arteriovenous graft may further comprise a connector for facilitating attachment of the catheter portion to the graft portion. The connector may be pre-connected to the graft portion, or may be integral with the graft portion. The arteriovenous graft may also further comprise a strain relief tube about the catheter portion, said strain relief tube having a first end and a second end, the second end comprising two or more flexural sections and two or more separations between the flexural sections. The arteriovenous graft may also further comprise a means for controlling blood flow rate through the internal passageway, and/or a means for monitoring blood flow rate through the internal passageway.

In one embodiment, a method for treating a patient is provided, comprising providing a first and second conduit of a vascular access system, accessing a vein at a first access site, inserting the first conduit of the vascular access system into the vein, forming a subcutaneous pathway between the first access site and an intermediate access site, accessing an artery at a second access site, attaching the second conduit to an artery through the second access site, and positioning the first conduit and second conduit of the vascular access system in the subcutaneous pathway. The method may further comprise connecting the first conduit and second conduit of the vascular access system. The positioning of the first conduit and second conduit in the subcutaneous pathway may comprise passing an end of the first conduit from the first access site to the intermediate access site and passing an end of the second conduit from the second access site to the intermediate access site. The method may further comprise connecting the end of the first conduit and the end of the second conduit and reinserting the connected ends of the first conduit and second conduit back through the intermediate access site. The positioning of the first conduit and second conduit in the subcutaneous pathway may comprise passing an end of the first conduit from the intermediate access site to the first access site and passing an end of the second conduit from the intermediate access site to the second access site, or connecting the end of the first conduit and the end of the second conduit and inserting the connected ends of the first conduit and second conduit back through the intermediate access site. The positioning of the first conduit and second conduit in the subcutaneous pathway may comprise passing an end of the first conduit from the first access site to the intermediate access site and passing an end of the second conduit from the intermediate access site to the second access site, or passing an end of the first conduit from the intermediate access site to the first access site and passing an end of the second conduit from the second access site to the intermediate access site.

In one embodiment, a method for treating a patient is provided, comprising providing a means for providing a blood pathway between a vein and an artery, accessing a vein at a first access site, inserting the means for providing a blood pathway between a vein and an artery into the vein, forming a subcutaneous pathway between the first access site and a second access site, attaching the means for providing a blood pathway between a vein and an artery at the second access site, and positioning the means for providing a blood pathway between a vein and an artery in the subcutaneous pathway.

In one embodiment of the invention, a device for treating a patient is provided, comprising a graft conduit comprising a first end, a second end, a lumen therebetween, an outer wall surface, an outer diameter, a lumen wall surface, and an inner diameter, a catheter conduit comprising a first end, a second end, a lumen therebetween, an outer wall surface, an outer diameter, and a lumen wall surface, an inner diameter, and a filament on or at least partially embedded at the outer wall surface, the filament being peelable from the outer wall surface, and a conduit connector having a first end, a second end, a lumen therebetween, wherein the first end of the conduit connector may be adapted to join the second end of the graft conduit, and the second end of the conduit connector may be adapted to joint the first end of the catheter conduit. The first end of the connector may be joined to the second end of the graft conduit. The catheter conduit may further comprise a wire reinforcement generally located between the outer wall surface and lumen wall surface and at least about the second end of the catheter conduit, a trimmable section about the first end of the catheter conduit and having an inner diameter and outer diameter, and an insertion section about the second end of the catheter conduit and having an inner diameter and outer diameter, wherein said trimmable section is adapted for implantation generally outside the vein and the insertion section is adapted for implantation generally inside the vein. The filament may be located within the trimmable section. The wire reinforcement may be a nitinol wire reinforcement. The insertion section may further comprises a wire reinforcement generally located between the outer wall surface and lumen wall surface of the catheter conduit. The catheter conduit may further comprise a wire reinforcement located within the trimmable section. The device may further comprise a means for temporary catheterization, and/or a self-sealing interface. The self-sealing interface comprises a multi-layer material wherein at least two layers of the material have different directional orientations, or a multi-layer material wherein at least one layer comprises a sealing gel between two polymeric layers.

In one embodiment, a device for treating a patient is provided, comprising a graft conduit comprising a first end, and a second end, wherein the second end comprises an elastic material, a catheter conduit comprising a first end, a second end, and a conduit connector having a first end, a second end, wherein the first end of the conduit connector may be adapted to join the second end of the graft conduit, wherein said elastic material of the graft conduit provide a snug fit with the first end of the conduit connector. The elastic material may be coated onto the second end of the graft conduit, and/or embedded into the second end of the graft conduit.

In one embodiment of the invention, a device for treating a patient is provided, comprising a catheter component with a lumen and at least one radio-opaque marker about a distal end of the catheter component, wherein the at least one radio-opaque marker comprising two or more layers of one or more radio-opaque materials having crush resilience to maintain patency of the lumen at the distal end. The at least one radio-opaque marker may be surrounded by radiolucent material.

In one embodiment, a device for treating a patient is provided, comprising a catheter component with a lumen and at least one multi-layer radio-opaque marker about a distal end of the catheter component, wherein the at least one multi-layer radio-opaque marker exhibits improved crush-resilience compared to a single-layer radio-opaque marker having the same radio-opacity to maintain patency of the lumen at the distal end In one embodiment, an arteriovenous graft is provided, comprising a generally tubular body having an outer wall and comprising a graft section adapted for attachment to an artery, a catheter section adapted to be inserted at least partially into a vein, and a strain relief element extending around at least a portion of said tubular body and comprising a generally tubular member mounted directly or indirectly to said outer wall and having at least one end formed into two or more flexural sections by two or more slots extending inwardly from said end between said flexural sections.

Said outer wall may have an outer diameter and said tubular member may have an internal diameter at said end, said internal diameter being greater than said outer diameter. The flexural sections may be petal-shaped. The slots may comprise rounded ends. The arteriovenous graft may comprise three to six slots.

In one embodiment, a device for relieving strain on a flexible tube subject to kinking is provided, said device comprising a generally tubular body having a first end and a second end, said second end having a periphery, comprising a plurality of flexible flap elements distributed around said periphery for distributing strain. The device may further comprise three to six slots between said flexible flap elements.

In one embodiment, a device for delivering a catheter is provided, comprising a shaft comprising a proximal end, distal end and a guidewire lumen therebetween, a distal end outer diameter and a collapsible distal tip, and a catheter section comprising a first end a second end, and a catheter lumen therebetween, wherein the collapsible distal tip has an expanded configuration comprising tapered surface and a reduced configuration adapted to move within the catheter lumen. The tapered surface of the collapsible distal tip may form a generally conical shape, may comprise an expandable balloon and the shaft further comprises a balloon lumen for inflating and deflating the expandable balloon, and/or may be further configured in its expanded configuration to seal the catheter lumen at the second end of the catheter section to resist retrograde fluid flow. In some embodiments, the collapsible distal tip comprises an expandable slotted tube.

In one embodiment, a method for inserting a catheter is provided, comprising providing a catheter insert comprising an insert shaft with a guidewire lumen, and a collapsible distal tapered tip having an expanded configuration and a reduced configuration, providing a catheter having a first end a second end, and a lumen therebetween, inserting the catheter insert into the lumen of the catheter, expanding the collapsible distal tapered tip to its expanded configuration, passing the distal tapered tip of the catheter insert into a vein, positioning the catheter and catheter insert into the vein, and collapsing the collapsible distal tapered tip to its reduced configuration. In some embodiments, the method may further comprise sealing the second end of the catheter with the collapsible distal tapered tip in the expanded configuration, removing the catheter insert from the catheter lumen, and/or clamping the catheter to resist blood flow out of the catheter lumen.

In one embodiment, a device for treating a patient is provided, comprising an implantable arteriovenous graft, comprising a vein insertion end, an artery attachment end, a tubular wall and a lumen therebetween, and a flow rate control element for reversibly changing a net cross-sectional surface area of the lumen. The flow rate control element may be a compression element or a distensible fluid compartment. The distensible fluid compartment may expand to compress the blood pathway cross-sectional area by at least about 25%, at least about 50%, at least about 75%, at least about 90% or at least about 95%. The compression element may comprise a clamp structure about the lumen of the implantable arteriovenous graft conduit. The clamp structure can clamp to compress the blood pathway cross-sectional area by at least about 25%, at least about 50%, at least about 75%, at least about 90% or at least about 95%. The flow rate control element may be a contiguous secondary lumen having an expanded configuration during at least a portion of a dialysis treatment and a reduced configuration between dialysis treatments. The secondary lumen may be biased to the reduced configuration.

In one embodiment, a method for performing dialysis, comprising providing an implantable arteriovenous graft, comprising a vein insertion end, an artery attachment end, a tubular wall, a lumen therebetween, and a flow rate control element for reversibly changing net blood flow rate in the lumen, increasing the net blood flow rate during at least portion of a dialysis treatment, and reducing the net blood flow rate between dialysis treatments.

In one embodiment, a device for treating a patient is provided, comprising an implantable arteriovenous graft conduit, comprising a vein insertion end, an artery attachment end, a tubular wall and a lumen therebetween, and a flow sensor system at least partially embedded within the tubular wall. The flow sensor system may comprise a flow sensing element and an antenna, and may further comprise an external receiver. The external receiver may comprise a power supply, a transmitter, a receiving element, a signal processor and a flow readout. The flow sensor element may be a heat sensor, a pressure sensor, a magnetic sensor, a Doppler ultrasound sensor, and/or an ion sensor.

Further features and advantages of the present invention will become apparent to those of skill in the art in view of the disclosure herein, when considered together with the attached drawings and claims.

BRIEF DESCRIPTION OF THE DRAWINGS

The structure and method of using the invention will be better understood with the following detailed description of embodiments of the invention, along with the accompanying illustrations, in which:

FIG. 15 is an elevational view of one embodiment of the invention comprising a multi-component vascular access system with an access region of self-sealing material.

FIG. 16 is a schematic representation of a vascular access system with a transcutaneous port.

FIG. 19B depicts the removal of a portion of the filament from FIG. 19A. FIG. 19C illustrates the catheter section of FIGS. 19A and 19B prepared for fitting to a connector.

FIGS. 24A to 24I are schematic cross-sectional views of one embodiment of a device for inserting the catheter section of the vascular access system into a blood vessel.

FIGS. 27A and 27B are detailed schematic representations of vascular access system coupled to a temporary catheter using a compressive interface.

FIGS. 28A and 28B are schematic cross-sectional views of a conduit connector with a pair of mechanical valves for attaching a temporary catheter in the open and closed configurations, respectively.

FIGS. 30A to 30C are schematic representations of a locking temporary catheter used with a proximal plug and catheter cutter.

FIGS. 32A and 32B are schematic axial cross-sectional views of another embodiment of the invention comprising a dual-compartment flow control section of a vascular access system in high-flow and low-flow states, respectively.

FIGS. 37A to 37E are schematic representations of another embodiment of the invention for implanting a two-section vascular access system.

DETAILED DESCRIPTION OF THE PREFERRED EMBODIMENT

Figures 1A, 1B, 1C:
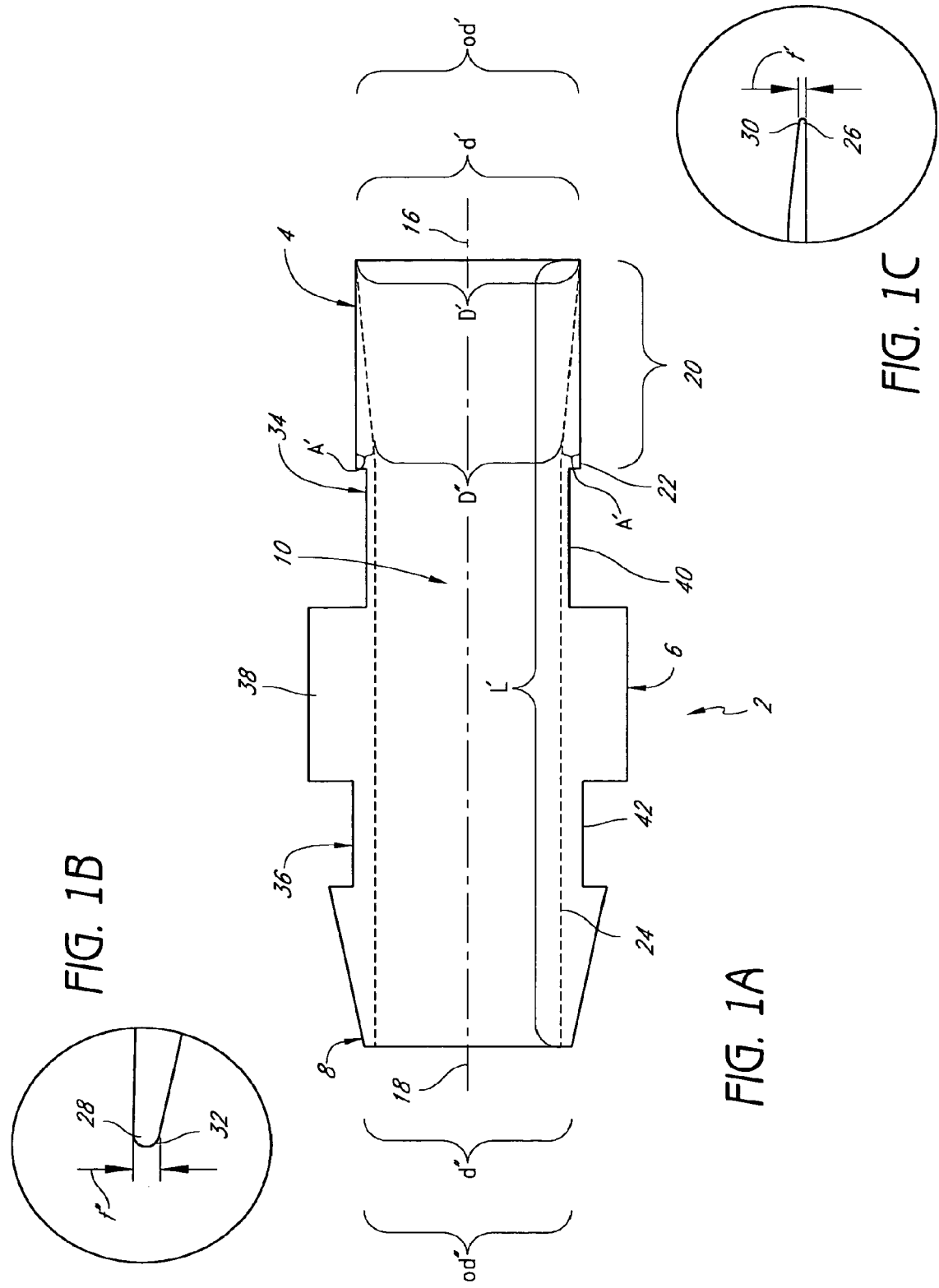
FIG. 1A is a cross-sectional schematic view of one embodiment of the connector.
FIGS. 1B and 1C depict the connector edges of the connector in FIG. 1A.

Research indicates that graft failures from localized stenosis at the venous end of AV grafts are primarily due to intimal hyperplasia, compliance mismatch between the graft and the native vein anastomosis, and turbulent flow at the anastomosis site. Kanterman R. Y. et al "Dialysis access grafts: Anatomic location of venous stenosis and results of angioplasty." Radiology 195: 135-139, 1995. We hypothesize that these causes could be circumvented by eliminating the venous anastomosis and instead, using a catheter to discharge the blood directly into the venous system. We have developed vascular access system that eliminates the venous anastomosis in the AV shunt, using a catheter element at the venous end and a synthetic graft element anastomosed to the artery in the standard fashion. We believe that such system should eliminate or reduce venous hyperplasia, which is the largest reason for AV shunt failure.

A. Vascular Access System

Although these devices may be may be constructed as a single-piece, integrated device, a multi-piece device comprising separate components that are later joined together may also be designed. A multi-component device may have several advantages. First, a multi-piece device allows switch-out of one or more components of the device. This allows the tailoring of various device characteristics to the particular anatomy and/or disease state, for instance, by using components of different dimensions. This also reduces the cost of treating patients in several ways. It reduces the amount of inventory of a given device by stocking an inventory range of components, rather than an inventory range of complete devices. Also, if an incorrect device is initially selected for use in a patient, only the incorrect component is discarded, rather than the entire device. Second, separate multiple components of a device may be easier to manufacture compared to an integrated form of the device. Third, it may be easier for a physician to implant separate components of a device and then join them together rather than implanting an integrated device. Fourth, it allows the components to be trimmable as needed to accommodate various patient anatomies. An integrated device may be excessively bulky and can slow the implantation procedure, thereby increasing operating room time and costs as well as increasing the risk of physician error.

The interfaces where separate components are joined or attached, however, are potential sources of turbulent flow along the blood flow path of the device. Sharp indentations or protrusions of the lumen will cause alterations in flow at the interface that may result in hemolysis and clot formation. Such an interface may create an increased risk of creep or separation of joined components over time that can worsen the flow characteristics at the interfaces or even result in loss of flow, respectively. Thus, the connector system used to attach the various components may benefit from one or more design features that maintain smooth flow between components through the interface and also resist creep or separation of the joined components. Such a connector system may be used with AV grafts, peripherally inserted central catheters (PICC), implantable infusion catheters with and without fluid reservoirs, implantable infusion pumps, left ventricular assist devices, and any other device where providing laminar flow between two body fluid conduits may be beneficial. For example, such a connector may be used to join an arterial graft and a venous catheter as described by Squitieri in U.S. Pat. Nos. 6,102,884 and 6,582,409, and by Porter in U.S. Provisional Application No. 60/509,428, herein incorporated by reference in their entirety. In addition to joining tubular conduits, the connector may also be used to join conduit or reservoir containing devices such as needle access ports as described by Porter in U.S. Provisional Application No. 60/605,681, herein incorporated by reference in their entirety. The connectors may also be integrated with such conduit or reservoir containing devices.

In one embodiment of the invention, a connection system for attaching a catheter to a graft in an AV hemodialysis shunt is provided. The connection system may comprise a biocompatible and/or hemocompatible material. The connection system may also provide for the attaching of a graft and a catheter having different internal and/or outer diameters. In some embodiments of the invention, the connection system provides a lumen with a smooth fluid path from one end of the connection system to the other. The smooth fluid path may reduce the risk of clot formation and hemolysis of red blood cells. The connector system may also have a securing system for resisting disconnection of the joined components. An anti-kink system may also be provided to resist occlusion along portions of the catheter and/or graft. An anti-kink system may be advantageous for an AV graft comprising PTFE or a catheter comprising silicone or polyurethane, which may be prone to bending and/or twisting. It may also be advantageous to preconnect one element to the connector before the start of surgery which then makes the procedure easier to perform in the operating room and it may also reduce the chance of error.

Figure 2A:
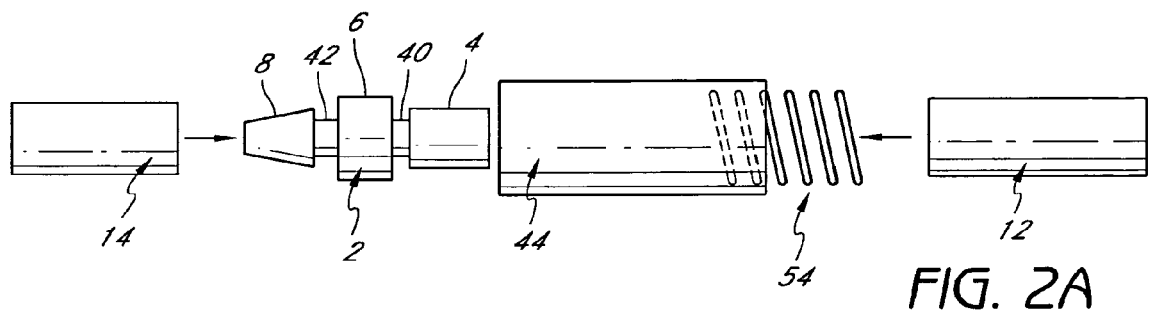
FIG. 2A is an exploded view of one embodiment of the connector system.

FIG. 1 depicts one embodiment of the invention. The invention comprises a connector 2 having a first end 4 for connecting to a first fluid conduit, a middle portion 6 and a second end 8 for connecting to a second fluid conduit, and a lumen 10 from the first end to the second end. Referring to FIG. 2A, the first fluid conduit 12 is typically a hemodialysis graft component while the second fluid conduit 14 is typically a catheter, but other combinations may also be used, such as graft/graft, catheter/graft or catheter/catheter. Other combinations may also be useful in performing bypass grafts for peripheral vascular disease and liver cirrhosis, and for connecting blood pumps or cardiopulmonary bypass machines. Multiple conduits may also be joined in a serial fashion. The invention disclosed is also applicable to Y-connectors or other branching connectors. The connector may be designed with fluid flow in a direction from the first conduit to the second conduit. This direction of fluid flow may also be defined from upstream to downstream, or from proximal to distal. In other embodiments, the connector may be configured without a particular fluid flow direction.

Where the connector is used to join conduits having generally similar inside diameters, the lumen diameter of the connector may be generally constant from the proximal portion of the first end to the distal portion of the second end. More typically, however, the conduits have different inner diameters, where the first fluid conduit has a greater diameter than the second fluid conduit. Referring back to FIG. 1A, in such circumstances, the most proximal portion 16 of the lumen 10 generally has a larger diameter d' and the most distal portion 18 of lumen generally has a smaller diameter d". A smooth transition between the larger diameter d' and the smaller diameter d" is provided to reduce turbulent or non-laminar blood flow and hemolysis that may result from abrupt changes in diameter. The change in diameter may be any non-abrupt transition, and may be linear or non-linear. The transition in lumen diameter occurs in a transition zone 20 occupying a portion or the entire length of the lumen 10, but preferably at least about 20% of the lumen length L', sometimes at least about 25% of the lumen length L', other times at least about 50% of the lumen length and occasionally over at least about 90% to about 100% of lumen length L'. In some embodiments, the tapering or diameter change of the lumen 10 occurs at no more than about a 30 degree angle as measured on a longitudinal cross section of the connector by the angle A' between the lumen wall 22 and a line parallel to the longitudinal axis of the lumen and intersecting the lumen wall at the most proximal portion 16. In other embodiments, the diameter change of the lumen 10 occurs at no more than about a 20 degree angle. In some embodiments, the tapering occurs at no greater than about a 10 degree angle, or no greater than about a 5 degree angle. In still other embodiments, the diameter of the connector changes as a percentage of the largest lumen diameter per unit percentage of lumen length. For example, in one embodiment, the diameter decreases by no more than about 3% of the largest lumen diameter per 1% of the lumen length. In other embodiments, the diameter decreases by no more than about 2% of the largest lumen diameter per 1% of the lumen length, and in still other embodiments, the diameter decreases by no more than about 1% or 0.5% of the diameter per 1% of the lumen length. One skilled in the art can select the length of the transition zone based upon the total length of the lumen and/or the amount of diameter change required.

In other embodiments, the first fluid conduit 12 may have a smaller diameter than the second fluid conduit 14 and the connector 2 may be configured so that the most proximal portion 16 of the lumen 10 generally has a smaller diameter and the most distal portion 18 of lumen 10 generally has a larger diameter.

In one embodiment, the transition zone 20 of the connector 2 where the lumen diameter transitions from the larger diameter D' to the smaller diameter D" is preferably located at the most proximal portion 16 of the connector and extends distally to at least to the distal portion 22 of the first end 4. The transition zone 20 may also begin at the distal portion 22 of the first end 4, the middle portion 6, or the proximal portion 24 of the second end 8 of the connector 2, and terminate at the middle portion 6, the proximal portion 24 of the second end 8 or the distal portion 18 of the second end 8 of the connector 2, depending on the length of the transition zone 20 desired. FIG. 1A depicts one embodiment with a transition zone 20 from a larger diameter D' to a smaller diameter D" generally within the first end 4 of the connector 2, and a constant diameter d" within the remaining portions of the lumen 10. As shown in FIG. 1C, a transition zone 20 with a larger diameter D' located at the most proximal portion 16 of the first end 4 may be advantageous because it allows a smaller thickness t' of connector material at the leading edge 26 of the connector. The reduced connector wall profile or thickness provides a smaller effective surface area that is perpendicular to the fluid flow from the first conduit 12 to the connector 2, thereby reducing disruption of laminar flow, yet maintains the integrity of the connector 2 by allowing an increased connector material thickness as the internal diameter of the connector lumen tapers.

Figure 3:
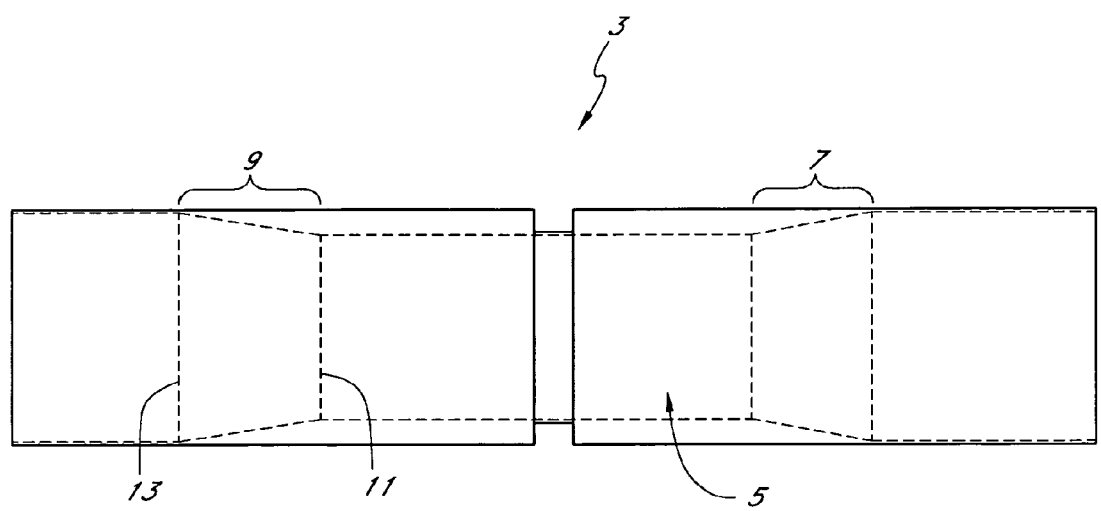
FIG. 3 is a schematic representation of one embodiment of the invention comprising a double-tapered connector.

A connector may also have more than one transition zone. Referring to FIG. 3, in one embodiment, the connector 3 comprises a lumen 5 with a first transition zone 7 and a second transition zone 9. The second transition zone 9 has a third inside diameter 11 that is smaller than its fourth inside diameter 13, thus a transition zone may be configured to go from a smaller diameter to a larger diameter, as well as a larger diameter to a smaller diameter.

FIGS. 1B and 1C depict one embodiment of the invention comprising a reduced thickness of the connector wall t', t" at the edges 26, 28 of the connector 2. The reduced connector wall thicknesses t', t" allows the lumen 10 of the connector 2 to remain generally flush or nearly flush with the lumens of the conduits joined at each end 4,8. In some embodiments, the connector wall thicknesses are configured to reduce t' and t" sufficiently to decrease the flow disturbance in the lumen while having an edge profile shaped in such a way that reduces the risk of cutting the lumens of the tubing or pose a hazard to the surgeon. In one embodiment, the connector wall thicknesses are optimized to reduce t' and t" as small as possible to prevent flow disturbance in the lumen while having an edge profile shaped in such a way that it does not cut the lumens of the tubing or pose a hazard to the surgeon. For some embodiments, the thickness of the connector wall t', t" may be determined at a measurement point in the lumen about 0.5 mm or 1.0 mm from the lumen opening. The measurement point of the thickness t', t" of the connector wall may also be defined at the inflection point 30, 32 where the connector edge 26, 28 joins the linear lumen wall as identified on a longitudinal cross section of the connector 2. Where the connector edges 26, 28 are rounded or smoothed, the inflection points are where the curves of the edges 26, 28 meet the linear lumen wall edges as defined on a longitudinal cross section of the connector 2. In some embodiments of the invention, the connector edges 26, 28 at the ends 4, 8 of the connector 2 generally have a thickness t', t" no greater than about 20% of the inner diameter of the lumen d', d" at the most proximal portion 16 and most distal portion 18 of the lumen 10, respectively. In some instances, the thickness of at least one connector edge t', t" is less than about 10% of the inner diameter d', d" of the lumen 10 at one connector edge, respectively, and in still other circumstances, the thickness t', t" is preferably less than about 5% or about 3% of the inner diameter d', d" of the lumen 10, respectively. The connector wall thickness t', t" may also be defined relative to the outer diameter od', od" of the connector 2 at the same measurement point. Thus, the connector wall thickness t', t" may be no greater than about 20% of the outer diameter od', od" of the connector 2, respectively, and in some instances no greater than about 10% of the outer diameter od', od" of the connector 2, respectively, and preferably less than about 5%, about 3% or about 1% of the outer diameter od', od" of the connector 2 at the measurement point, respectively.

As depicted in FIG. 1C, in another embodiment, the thickness t' of the edge 26 of the first end 4 at the selected measurement point is generally within the range of about 0.030 mm to about 0.250 mm, sometimes within the range of about 0.075 mm to about 0.200 mm, and occasionally about within the range of about 0.100 mm to about 0.180 mm. As illustrated in FIG. 1B, in another embodiment, the thickness of the trailing edge 28 of the second end 8 is generally within the range of about 0.030 mm to about 0.400 mm, sometimes within the range of about 0.125 mm to about 0.300 mm, and occasionally within the range of about 0.175 mm to about 0.250 mm.

To further reduce flow turbulence or non-laminar flow and prevent damage to the surface of the inner surface of the conduits at one or more edges 26, 28 of the connector 2, the first end 4 and/or second end 8 of the connector 2 may be advantageously rounded or smoothed. Rounded edges may also decrease the risk of trauma to the conduits 12, 14 during insertion of the connector 2 into the conduits 12, 14. As shown in FIGS. 1B and 1C, the rounded edges may have a generally semi-circular cross-section, but the edges may also have a cross-section with a generally partial elliptical profile or polygonal profile. For embodiments having a semi-circular cross-sectional edge, the radius of the edge 26, 28 is generally about half of the thickness of the edge at the selected measurement point. Typically, the edge radius is within the range of about 0.025 mm to about 0.200 mm, and sometimes within the range of about 0.025 mm to about 0.125 mm, or occasionally within the range of about 0.075 mm to about 0.100 mm. The rounding or smoothing of the connector edge may be performed using electropolishing, mechanical polishing, or a chemical etchant such as hydrofluoric acid.

The outer diameter od' of the first end 4 of the connector 2 may be generally constant or it may taper from distal to proximal. In some circumstances, a first end 4 with a generally constant outer diameter may be preferable because the generally constant outer diameter reduces the deformation of the first conduit 12 at the junction of the connector edge 26 and the first conduit 12. The reduced deformation may preserve the structural integrity of the first conduit 12 when joined to the connector 2. It may also reduce the inward deformation that may occur at the junction of the connector edge 26 and the first conduit wall, which can provide a smoother fluid path transition from first conduit 12 to the connector 2. A tapered end, however, may facilitate insertion of the connector 2 into the lumen of the first conduit 12 while providing resistance to separation between the conduit 12 and connector 2.

The outer diameter od" of the second end 8 of the connector 2 may also be generally constant or have a taper to facilitate insertion into the second conduit 14. In some embodiments, a tapered outer diameter of the connector 2 may be preferred because the effect on flow dynamics, if any, from the lumen 10 of the connector 2 to the larger lumen of the second conduit 14 may not be significant. A taper at the second end 8 of the connector 2 may facilitate insertion of the second conduit 14 with little or no increase in flow turbulence or non-laminar flow. The configuration of one or both connector ends 4, 8 may be the same or different, and may be selected by one skilled in the art depending upon the flow direction, desired flow characteristics, conduit materials and characteristics, and other factors.

The middle portion 6 of the connector 2 has a proximal end 34 adjacent to the first end 4 of the connector 2, a distal end 36 adjacent to the second end 8 of the connector 2, and contains a segment of lumen 10. In one embodiment of the invention, the middle portion 6 has a radially outwardly extending annular flange 38 along at least one portion of its outer diameter that limits the insertion of the first end 4 and second end 8 into their respective conduits 12, 14. The insertion limit may prevent overinsertion of the connector 2 into the conduit, resulting in possible loss of the connector and/or damage to the conduit.

In some embodiments, the middle portion 6 of the connector 2 comprises one or more regions with indentations or a reduced outer diameter 40, 42 with respect to the adjacent outer diameters of the first end 4 and/or second end 8 of the connector 2. Preferably, the connector 2 has a first reduced outer diameter region 40 such as an annular recess adjacent to the first end 4 of the connector 2 and a second reduced outer diameter region 42 such as an annular recess adjacent to the second end 8 of the connector 2, but this is not required. The two regions 40, 42 need not be configured similarly. The regions 40, 42 on the middle portion 6 of the connector 2 allow conduits 12, 14 inserted over the first end 4 and/or second end 8 of the connector 2 to be secured to the connector 2 by placing a radially inward force on the conduits 12, 14 that can partially deform the conduits 12, 14 radially inward and increase resistance to separation from the connector 2 through a friction fit and/or mechanical interfit by abutting against the larger diameter of the first end 4 and/or second end 8 of the connector 2. The indentation or reduced outer diameter regions 40, 42 may involve only a portion of the circumference of the connector 2, but typically will involve the entire circumference of the connector 2. Structures for securing the conduits 12, 14 onto the connector 2 are described in further detail below.

In one embodiment, the connector 2 has a length of about 10 mm to about 50 mm, and preferably about 15 mm to about 30 mm and more preferably about 20 mm to about 25 mm. The connector may comprise any of a variety of biocompatible materials, such as titanium or a titanium alloy, nickel or a nickel alloy, MP35N, stainless steel, polysulfone, PEEK, nylon, polypropylene or polyethylene or any flexible or chip-resistant polymer. All or a portion of the outer and/or inner surface of a metallic connector may be passivated or anodized. All or a portion of the outer and/or inner surface of the connector may be coated or insert molded with silicone or other hemocompatible material to provide a lubricious characteristic or to augment other properties of the connector, such as corrosiveness and/or clot formation. The connector may further comprise a drug eluting surface capable of eluting a therapeutic agent that can reduce the risk of infection, clot formation or affect tissue growth about the connector 2.

Figure 2B:
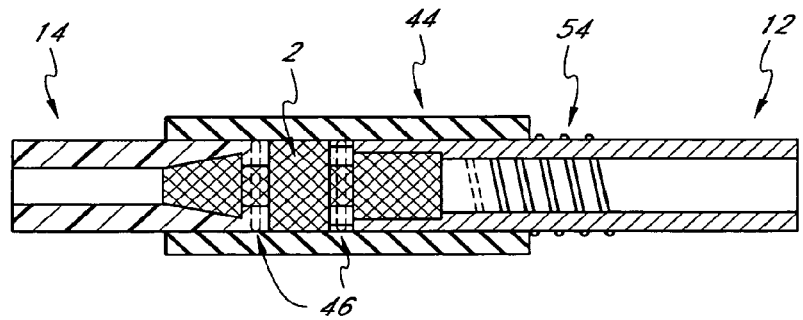
FIG. 2B is a cross-sectional view of the connector system in FIG. 2A when assembled.

FIGS. 2A and 2B depict one embodiment of the invention comprising a first conduit 12, second conduit 14, a connector 2 and a connector sleeve 44. The connector sleeve 44 comprises a tubular structure capable of fitting over the connector 2 and at least one and preferably both conduits 12, 14 joined to the connector 2. The connector sleeve 44 may be capable of applying a radially inward compressive force onto the connector 2 and joined conduits 12, 14. The compressive force may further depress portions of the conduits 12, 14 into the reduced outer diameter regions 40, 42 of the connector 2 and further secure the conduits 12, 14 onto the connector 2. In some embodiments where the connector sleeve 44 is positioned to extend beyond the first end 4 and/or second end 8 of the connector 2, the compressive force may impart a slight radially inward deformation of the joined conduits 12, 14 relative to the connector edges 26, 28 that may reduce the difference, if any, between the lumen diameter of the conduit and the lumen diameters d', d" of the connector ends 4, 8 to which the conduits 12, 14 are joined. The connector sleeve 44 may also reduce exposure of any crevices or spaces along the outer surfaces of the connector 2 and thereby eliminate infection risk posed by such areas. Although a single sleeve 44 is depicted in FIGS. 2A and 2B, separate sleeves to cover and/or compress each conduit may also be used.

In one embodiment, the connector sleeve 44 comprises silicone, polyurethane or other polymer in its unexpanded state, has an average inner diameter less than that of the largest outer diameter and/or average outer diameter of the connector 2. The connector sleeve 44 is radially expanded as it is placed over the connector 2 and joined conduits 12, 14, thereby imparting a radially inward compression force.

In another embodiment, the connector sleeve 44 comprises a polymer that may be UV or heat shrunk onto the connector 2. UV and heat shrink polymers include but are not limited to PTFE, FEP, PFA, PET, and PTFE/FEP. In still other embodiments, the connector sleeve 44 may be adhered to the connector 2 and/or conduits 12, 14 with cyanoacrylate, a curable glue, or other adhesive. In still another embodiment, the connector sleeve 44 comprises a tubular lattice structure similar to a stent that is crimped onto the connector system. The stent may also comprise a shape memory material such as Nitinol that is capable of expanding with increased temperature and reducing in diameter with cooling to apply a radially inward force to the sleeve 44 or connector 2.

Securing structures or devices may be applied to the conduits to secure the conduits to the connector. These securing devices 46 may be applied directly to the outer surface of the conduits 12, 14, as shown in FIG. 2B, or they may be applied indirectly on the outer surface of the connector sleeve 44, or both. Application of one or more securing devices 46 onto the connector sleeve 44 may prevent or resist migration of the sleeve 44 with respect to the connector 2. The securing structures are described in greater detail below.

The radially inwardly facing surface of the connector sleeve 44 may also comprise at least one inner ring, indentation or other structure that is complementary to a corresponding structure on the outside surface of the connector and/or conduits that can facilitate positioning and/or securing of the sleeve 44 onto the connector 2. For example, the sleeve 44 may have a radially inwardly extending ring or thread that is complementary to a circumferential indentation area 40, 42 on the connector 2. The inner ring of the sleeve 44 may be segmented and complementary to a series of circumferential indentations on the connector to facilitate rotational alignment of the sleeve and connector in addition to longitudinal alignment.

Figure 4:
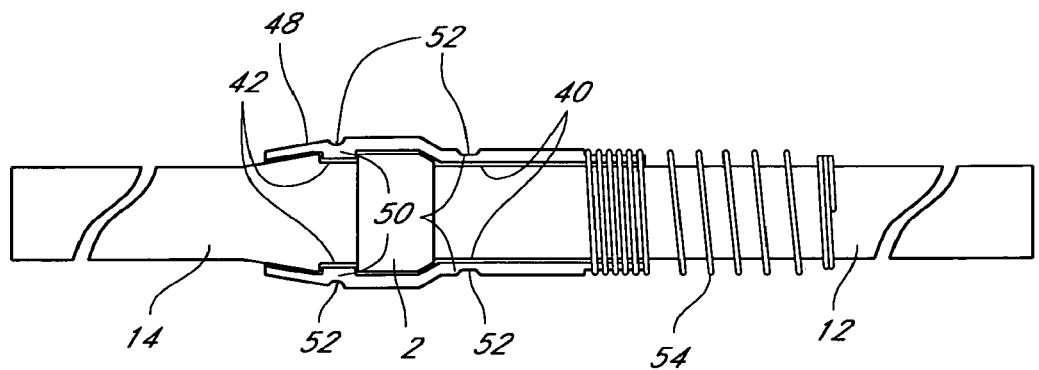
FIG. 4 is a schematic representation of one embodiment of the invention comprising a compression sleeve.

FIG. 4 illustrates one embodiment where the securing device comprises a compression sleeve 48 with radial protrusions 50 on the inner surface of the sleeve 48 capable of exerting radially inward pressure along the indented or reduced diameter portions 40, 42 of the connector 2 and/or conduits 12, 14 when positioned over the connector 2 and joined conduits 12, 14. The compression sleeve 48 may also have indentation points or regions 52 on its outer surface to facilitate use of other securing devices 46 such as clips, rings, sutures or others disclosed elsewhere herein to provide supplemental compression of the compression sleeve 48 onto the connector system.

In some embodiments of the invention, the interior surface of the connector sleeve 44 may have a lubricious coating to facilitate sliding of the sleeve 44 over the connector 2 and/or conduits 12, 14. The sleeve 44 may also comprise a porous material to facilitate tissue ingrowth and fixation of the connector system position within the body. Fixation of the connector system position may be advantageous when attempting puncture or obtain access to the joined conduits/grafts by preventing rolling or lateral displacement of the conduits caused by a puncturing force.

As shown in FIGS. 2A and 2B, the invention may further comprise a strain relief structure 54 to resist kinking of one or more conduits or grafts attached to the connector 2. This may be advantageous for conduits or grafts that comprise PTFE or other flexible materials and may prevent occlusion of the conduit or graft. The strain relief structure 54 typically comprises a flexible spiral or coil that extends from an end of the connector system and onto the outer surface of or within the wall of the conduit/graft. The strain relief structure may comprise a biocompatible metal or plastic. Other strain relief structures that may be used include a tubular or trumpet-shaped strain relief structure. The strain relief structure may be a separate structure from the connector 2 and/or connector sleeve 44, or may be embedded or integrated with the connector 2 or sleeve 44. FIG. 2A is a schematic of a connector system with a connector sleeve 44 and a separate strain relief structure 54. When all components are joined together as in FIG. 2B, the first conduit/graft 12 is inserted into the strain relief structure 54 and over the first end 4 of the connector 2. The second conduit 14 is inserted over the second end 8 of the connector 2. Both the first conduit 12 and second conduit 14 are secured to the connector 2 using securing devices. A connector sleeve 44 is located over a portion of the strain relief structure 54, first conduit 12, central flange 38, second conduit 14 and the securing structures 46 securing the first 12 and second conduits 14. A portion of the strain relief structure 54 is layered between connector sleeve 44 and first conduit 12 and is maintained at its position by radial compression from the connector sleeve and/or radial compression from the strain relief structure 54 onto the conduit 12.

Figure 5:
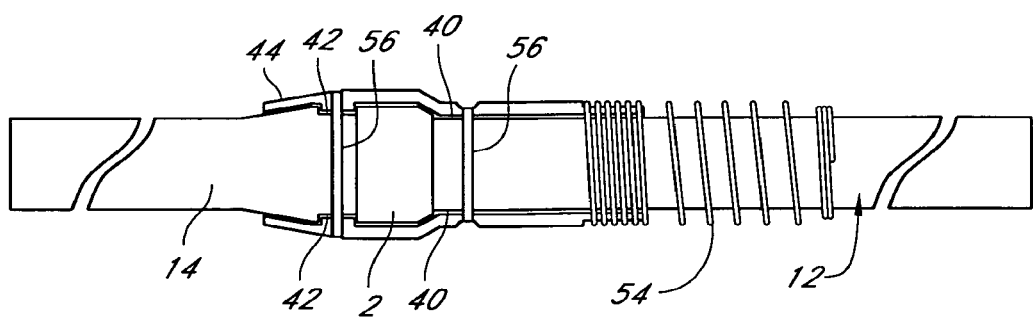
FIG. 5 is a schematic representation of one embodiment of the invention comprising a suture-secured sleeve.

Any of a variety of securing devices may be used to secure the conduits and/or connector sleeve 44 to the connector 2. FIG. 5 is a schematic view of one embodiment of the invention utilizing sutures 56 or wires to secure the conduits 12, 14 and connector sleeve 44 to the connector 2. The connector sleeve 44 is shown in cross-section to illustrate the interaction of the suture/wire 56, conduits 12, 14 and sleeve 44 with the reduced diameter portions 40, 42 of the connector 2. In one embodiment, one or more securing devices comprise nonabsorbable sutures well known in the art, and are tied around the connector sleeve 44 and conduits 12, 14 about the reduced diameter portions 40, 42 of the connector 2. In other embodiments, the securing device comprises a wire that is wound around the connector system and twisted several times to tighten the wire. FIG. 5 also depicts one embodiment of the strain relief assembly 54 that is positioned concentrically around the outer surface of the connector sleeve 44.

Figure 6:
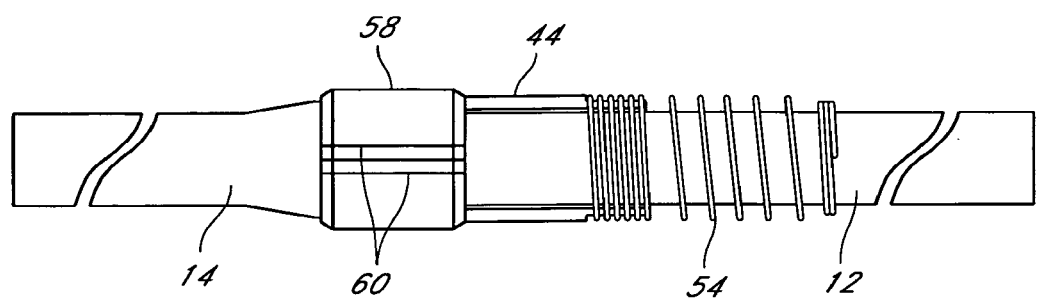
FIG. 6 is a schematic representation of one embodiment of the invention comprising a clamshell-secured sleeve.

FIG. 6 depicts another embodiment of the invention where the securing device comprises a clamshell assembly 58 configured to clamp around a portion of the connector 2. The clamshell assembly 58 may have one or more radially inwardly extending protrusions that interface with the reduced diameter portions 40, 42 or indentation points on the connector 2 that secure the conduits 12, 14 and sleeve 44 onto the connector 2. The clamshell assembly 58 may be configured to secure the conduits 12, 14 at one or both ends 4, 8 of the connector 2. A two-end clamshell assembly 58 is depicted in FIG. 5. The clamshell assembly 58 is generally C-shaped comprise a pair of complementary connecting structures 60 that can be joined to close the C-shape and form a tubular structure around the connector 2. The connecting structures 60 may be any of a variety of snap fits or other mechanical interfits.

Figure 7:
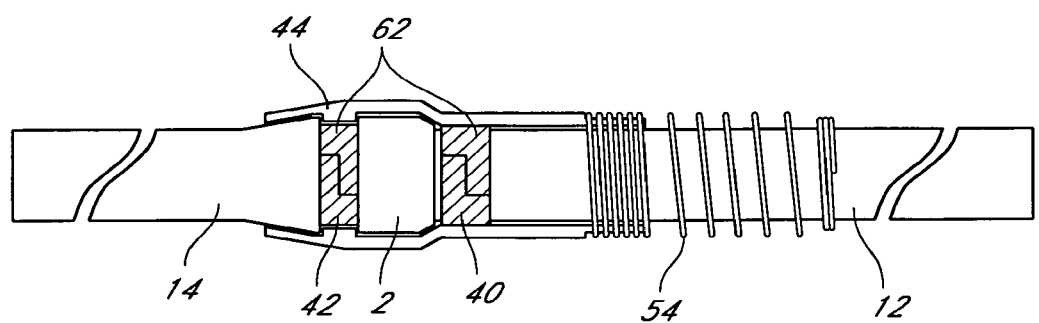
FIG. 7 is a schematic representation of one embodiment of the invention comprising clips for securing the graft and/or catheter to the connector system.

FIG. 7 is another embodiment where the securing devices comprise tension clips 62. The tension clips 62 are deformable C-shaped devices adapted for placement about the indentation points or regions 40, 42 of a connector 2 and are capable of exerting radially inward force as the arms of the tension clips 62 are separated. The tension clips 62 may have a rectangular, square, circular, elliptical, triangular or other polygonal cross-sectional shape. The width of the clip 62 for each end 4, 8 of the connector 2 may be the same or different. The cross-sectional shape and/or width of each clip 62 may be the same or different along the circumference of the clip. The cross-sectional shape and width may be selected based upon the particular material and characteristics of the conduit attached at that particular connector end. For example, a conduit or graft comprising PTFE may be more prone to damage with a relatively high securing force and may benefit from a tension clip 62 that exerts less force per surface area but maintains sufficient securing force through a wider clip with increased surface area. A catheter-type conduit, however, may comprise a more durable material than PTFE and can withstand higher radial compression force from a thinner clip that has an inverted triangle cross-sectional shape that is capable of applying a higher compression force at the bottom tip of the triangle, for example. In another embodiment, the tension clip may also be crimped to further increase the radial force acting on the connector and to secure the conduits. In still another embodiment, the securing device comprises a crimp ring that may lack inherent tension and is crimped onto the connector system to secure the joined conduits to the connector.

Figure 8:
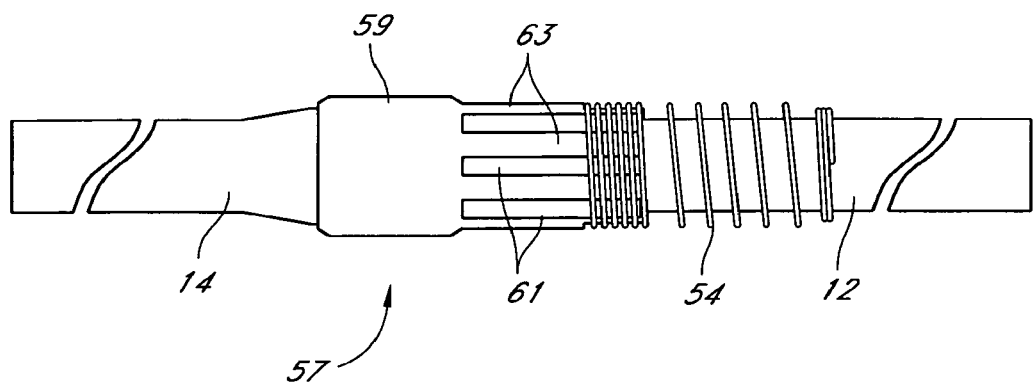
FIG. 8 is a schematic representation of one embodiment of the invention comprising a collet-secured sleeve.

FIG. 8 illustrates another embodiment of the invention comprising a collet securing device. In one embodiment, the collet 57 comprises a tubular assembly 59 with a series of radially-spaced longitudinal slits 61 between prongs 63 of the tubular assembly 59. After the conduits 12, 14 are attached to the connector 2, the collet 57 is slipped over the joined connector system. The prongs 63 may or may not have a radially inward bias capable of applying radially inward force against the connector sleeve 44 and/or conduits 12, 14. The prongs 63 of the collet 57 may be crimped to increase the radially inward force exerted by the collet 57. A strain relief assembly 54 may be placed around the prongs 63 of the collet 59 with sufficient radially inward force to at least secure the strain relief assembly 54 and may or may not exert radially inward force to further secure the sleeve 54 or conduits 12, 14. The collet may be configured to secure one or both of the conduits 12, 14.

Figure 9:
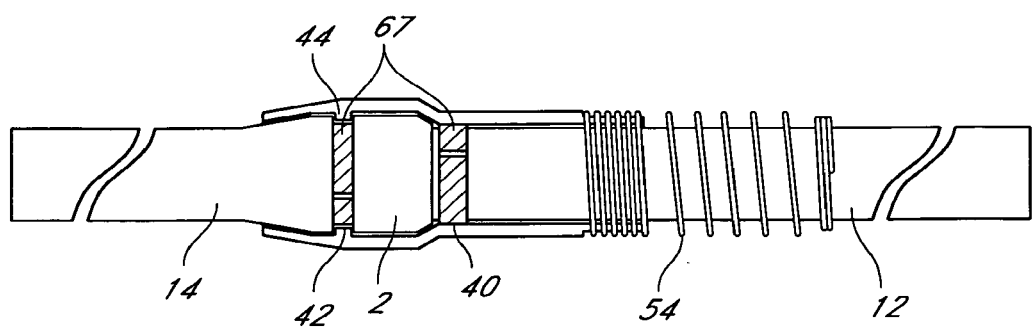
FIG. 9 is a schematic representation of one embodiment of the invention comprising a compression ring-secured sleeve.

FIG. 9 illustrates another embodiment of the invention where the securing device comprises a crimp or compression ring/collar 65. The compression ring/collar 65 is slipped over one or both conduits 12, 14 joined to the connector 2 and then collapsed with a crimp tool onto the surface of the conduits 12, 14. The compression ring/collar 67 may also be slipped over the connector sleeve 44 overlying the joined conduits and connector. The compression ring/collar 67 may then be crimped to secure the connector sleeve 44 in addition to the joined conduits 12, 14. As depicted in FIG. 9, the connector sleeve 44 may also be positioned onto the connector system after crimping of the compression rings or collars 67. The compression ring/collar 67 may have any of a variety of cross sectional shapes, including circular, oval, square, rectangular, triangular or other polygonal shape. The cross sectional shape of the compression ring/collar may be complementary to the corresponding indentation regions 40, 42 of the connector 2.

Figure 10:
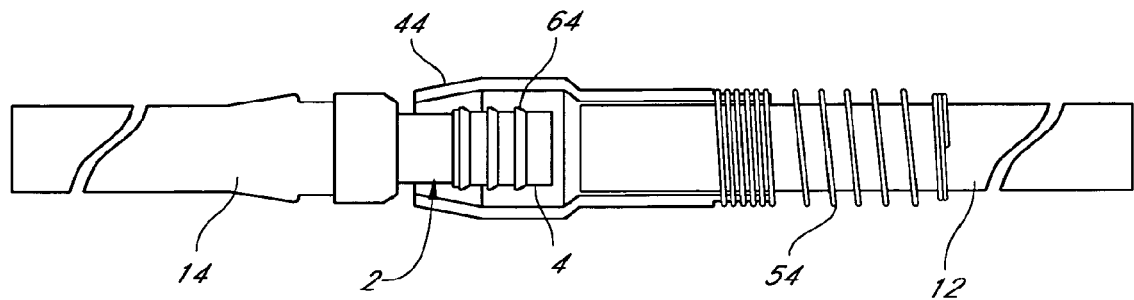
FIG. 10 is a schematic representation of one embodiment of the invention comprising barbs on the end of a connector end.

FIG. 10 depicts one embodiment of the invention comprising one or more barb-like protrusions 64 along the outer surface of at least one end 4 of the connector 2. The barb-like protrusions 64 may completely encircle the end 4 of the connector 2, as shown in FIG. 10, or partially encircle the connector end. The barb-like protrusions 64 include a ramped surface which inclines radially outwardly from the base of the protrusion to the tip of the protrusion in a direction away from the connector end 4. This orientation allows relative ease of insertion of the conduit 12 over the connector 2 but resists separation of the conduit 12 from the connector end 4. The barb-like protrusions 64 in FIG. 10 are located at the first or inflow end 4 of the connector 2 having a constant outside diameter, but may also be located on the second or outflow end 8 of a connector 2, or on a connector end with a tapering outside diameter.

Figure 11:
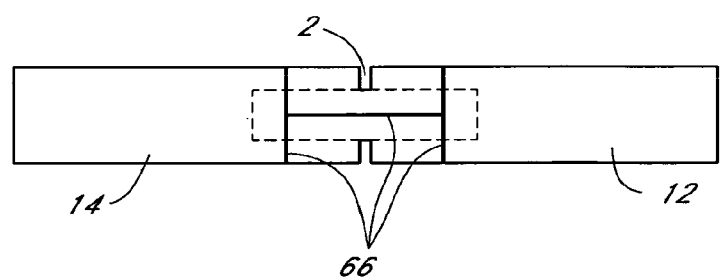
FIG. 11 is a schematic representation of one embodiment of the invention comprising a suture-secured connector system.

In one embodiment, shown in FIG. 11, the invention comprises a connector 2 without a central flange. This embodiment of the invention allows the ends of the two conduits 12, 14 to come in contact with each other and to encase the connector 2 completely. This embodiment minimizes surface protrusions along the AV graft. To secure the two conduits 12, 14, sutures 66 may be used to tie each conduit 12, 14 directly to the other conduit. Other securing devices, such as tension clips 62 or a clamshell/collet assembly 58, may be attached around the conduits 12, 14 about the connector 2, but these devices may increase the surface profile of the AV graft.

Figure 12:
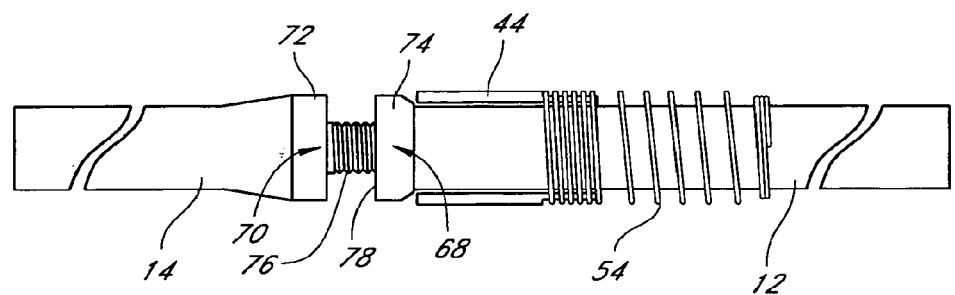
FIG. 12 is a schematic representation of one embodiment of the invention comprising a two-part connector.

FIG. 12 illustrates an embodiment of the invention comprising a two-component 68, 70 connector. The first component 68 and second component 70 of the connector each comprises a first end and a second end 72, 74 with a lumen therethrough. The first ends are adapted to receive a catheter or graft conduit. Each second end 72, 74 comprises a securing region for attaching a securing device to each component of the connector to secure the conduit to the connector component. Each second end also comprises a complementary portion 76, 78 of a mechanical interlock interface which is capable of releasably or permanently joining the two components 68, 70 of the connector. The mechanical interlock interface may comprise a male/female luer or other threaded interface, a flare or compression fit, or any other sealable mechanical interfit known in the art.

Figure 13:
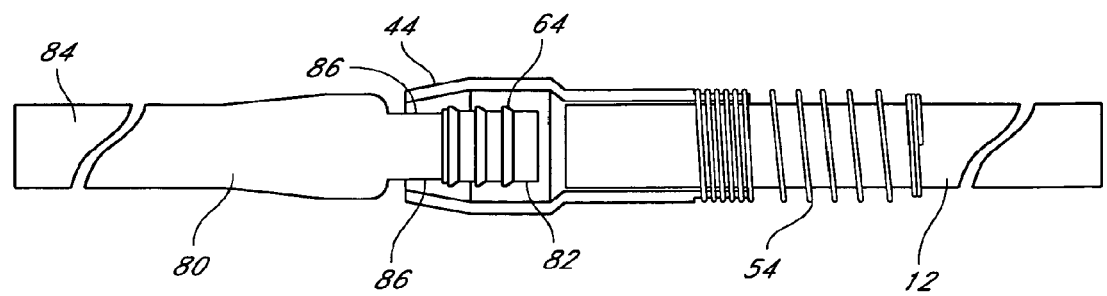
FIG. 13 is schematic representation of one embodiment of the invention comprising an integrated catheter and connector end.

In one embodiment of the invention, the connector system comprises a catheter 80 integrated with a connector-like end 82. FIG. 13 illustrates a catheter 80 comprising a first end 82 adapted for receiving a conduit or graft, a second end 84 configured for insertion into a vein, and a lumen from the first end to the second end. The second end 84 of the catheter 80 comprises a rounded connector edge and/or reduced catheter wall thickness at the selected measuring point as previously described. The second end 84 of the catheter 80 may further comprise one or more indentation points or regions 86 for securing the conduit or graft to the first end 82 of the catheter 80 with a securing device. A connector sleeve 44 may be placed over the second end of the catheter and graft to secure the graft to the catheter and/or to reduce exposure of the catheter/graft joint to the body.

In another embodiment of the invention, an AV shunt comprising a first body fluid segment, a second body fluid segment and a connector is provided. The first body fluid segment is configured for attachment to an artery and the second body fluid segment is adapted for insertion into a vein. The first body fluid segment may comprise a synthetic vascular graft. The synthetic vascular graft comprises a porous structure made from materials such as PTFE, polyurethane or silicone. In some embodiments of the invention, access to the AV shunt may be obtained by direct needle puncture of the vascular graft. The synthetic vascular graft may also comprise a biological material derived from humans or animals. Some embodiments of the vascular graft may be using needles or other access device after a maturation period, while other embodiments of the vascular graft may be used immediately following implantation of the graft.

The second body fluid segment may comprise a catheter or other conduit that is adapted to transport blood or other body fluid into the venous system. The second body fluid segment may have a first outer diameter that transitions to a second outer diameter adapted for insertion into a vein. In one embodiment, the second outer diameter may be within the range of about 3 mm to about 10 mm, sometimes within the range of about 4 mm to about 8 mm, and preferably about 5 mm. In some embodiments, the second body fluid segment is designed to be trimmable at the point of use to facilitate further customization of the device to a particular patient. The second body fluid segment may also have an embedded or external spiral support to provide kink resistance.

The selection of the inner diameter, outer diameter and length of the two segments may be selected by one skilled in the art, based upon factors including but not limited to the vein into which the second body fluid segment is being inserted into, the length of catheter to be inserted through the vein wall, as well as the desired flow rate and fluid resistance characteristics.

In one embodiment, the invention further comprises a conduit access or needle access site. The needle access site may be on the catheter and/or the graft, involving direct puncture of the catheter and/graft components with a needle. The invention may further comprise a separate needle access site structure attached to the catheter, graft or to both, using one or more connectors. The conduit access site may be subcutaneous or transcutaneous. Access to the conduit is typically obtained by using needle puncture, but other sealable or valved interfaces capable of non-piercing access are known in the art and may also be used.

Figure 14:
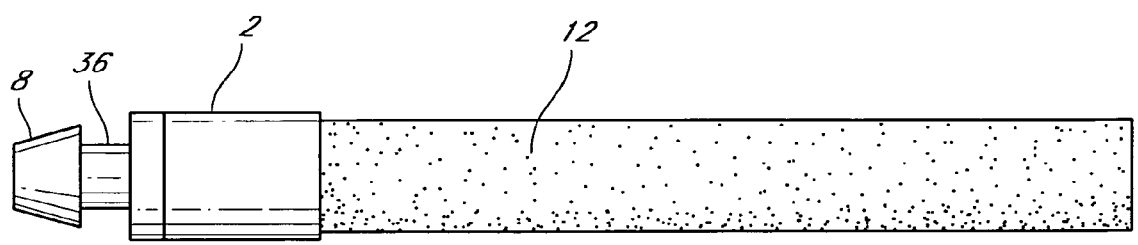
FIG. 14 is an elevation view of one embodiment comprising a preconnected conduit and connector.

In one embodiment, the invention comprises a method of forming an AV hemodialysis graft. A connector system comprising a graft, a catheter and a connector is provided. The first end of the graft is attached to an artery in the body and the second end of the catheter is inserted into the lumen of a vein. The second end of the graft is attached to the first end of the connector and the first end of the catheter is attached to the second end of the connector. The artery may be the radial artery, ulnar artery, brachial artery, axial artery, femoral artery, popliteal artery, anterior tibial artery, posterior tibial artery, dorsalis pedis artery, hypogastric artery, external iliac artery, thoracic aorta, abdominal aorta, common carotid artery, external carotid artery, internal carotid artery, vertebral arteries, renal artery or any other artery where AV anastomosis is desired. The vein may be a cephalic vein, basilic vein, brachial vein, axillary vein, subclavian vein, a pulmonary vein, an innominate vein, internal mammary vein, azygous vein, a basivertebral vein, an intervertebral vein, external jugular vein, internal jugular vein, a vertebral vein, saphenous vein, popliteal vein, femoral vein, deep femoral vein, external iliac vein, common iliac vein, hypogastric vein, the inferior vena cava, the superior vena cava, renal vein, hepatic vein, portal vein or any other vein or a lymphatic duct in the body. In some embodiments of the invention, the connector may be attached to the graft and/or catheter at the point of manufacture. In some embodiments, the connector may be attached to the graft and/or catheter prior to attaching or inserting the graft and/or catheter to the blood vessel, respectively. FIG. 14 depicts one embodiment of the invention comprising a connector 2 preconnected to a conduit 12.

B. Improvements to Vascular Access System

In the one embodiment of the invention, depicted in FIG. 15, the vascular access system (VAS) 100 comprises a first section 102 of graft material with an integrated connector end 104 attachable to a second section 106 comprising a catheter component that is adapted to transport the blood and also to be inserted into the venous system using a venotomy or even less-invasive procedure. The second section 106 may have a small diameter of about 7 mm or less, preferably about 6 mm or less, and most preferably about 5 mm or less so it does not require a large venotomy to implant the second section 106 and whereby the second section 106 does not occupy an excessive amount of space in the venous system. The VAS 100 preferably has thin walls to maximize the area available to flow through the VAS 100, which may be achieved using reinforced thin-wall tubing. The second section 106 has an opening adapted to be within the vein itself and wherein the opening is distant or is located downstream from the insertion site where the second section 106 inserts into the vein. The portion of the second section 106 insertable into the vein has an outer diameter which is less than an inner diameter of the vein in which it is disposed such that, in operation, blood can flow through the second section into the vein and also through the vein itself around the outer surface of the second section 106. The second section 106 may be adapted to be entirely subcutaneous in use and configured to avoid, in use, a blood reservoir therein and to provide continuous blood flow. The selection of the diameter and length of the two sections 102, 106 may be determined by assessing the vein in which the VAS 100 is to be inserted, the insertion length of the second section 106, and/or possibly the flow rate and pressure drop criteria needed to perform hemodialysis.

The second section 106 may be trimmed and then attached to the graft section 102 to achieve the desired total length. The graft and catheter sections 102, 106 are made to resist kinking and crushing, yet not be excessively stiff. In one embodiment of the invention, these properties may be provided by a spiral reinforcement 108 in a silicone tubing 110. Other materials that may be used include PTFE, polyurethane and other hemocompatible polymers. Also shown in FIG. 15 is a section of the catheter element 106 comprising a self-sealing area 112 that provides access by needles to perform dialysis either temporarily while the graft 102 is healing in or on a long-term basis. The self-sealing area 112 is preferably self-supported (e.g. frameless), generally having the same diameter and shape as the catheter and/or graft sections of the VAS, generally having a tubular configuration so that is may be punctured at any point along its length and/or circumference. The self-sealing area 112 may comprise a self-sealing material that forms a layer of the wall of at least a portion of the graft and/or catheter section of the VAS. Unlike self-sealing material provided in an access port, the self-sealing area 112 remains flexible along its length or longitudinal axis to facilitate implantation of the VAS and also to provide a longer self-sealing area 112 than can be provided by a self-sealing region on a bulky access port. The longer length allows the insertion of dialysis needles within a larger surface area so that the same small skin region need not be repeatedly pierced and thereby significantly reducing the chance of forming a sinus tract, which could lead to infection and/or bleeding. This also allows a given needle tract more time to recover between needle piercings, and therefore may further reduce the risk of infection and/or bleeding compared to traditional access ports. In one embodiment, the self-sealing area 112 has a length of at least about 2 inches, in other embodiments at least about 3 inches, and in still other embodiments, at least about 4 inches or 5 inches. The VAS may also optionally comprise a flow sensor that is imbedded in the wall of the VAS which can be interrogated externally to give a reading of flow in the device, and/or a section of tubing that can be adjusted post implant to control flow. These and other features are described in greater detail below.

Other access sites may be provided using one or more other components, structures or materials, including the use a puncture-resistant, circumferentially compressed tubing material in a portion of or all of the catheter section, a gel material sandwiched within the walls of the tubing, a low durometer material, a needle-accessible graft section or any combination thereof, an implantable port than can be accessed by needles, and/or a transcutaneous port 114 accessible without piercing the skin 116, as depicted in FIG. 16. Some of these features are discussed in greater detail below.

In some embodiments of the invention, the graft and/or catheter sections may also be coated with one or more therapeutic agents to address any of a variety of VAS-related effects, including but not limited to resisting thrombosis, reducing infection, speeding up healing time, promoting cell growth and/or improving arterial anastomosis. These agents include but are not limited to heparin, carbon, silver compounds, collagen, antibiotics, and anti-restenotic agents such as rapamycin or paclitaxel. These agents may be bonded to a surface of the VAS, as is known in the art, with heparin and chlorhexidine-bonded materials, or these agents may be eluted from a drug-eluting polymer coating.

Similarly, the porosity and other characteristics of the self-sealing area 112 may also be altered to augment its effects. For example, this can be done by varying the porosity, construction and wall thickness of the conduit material. Some commonly used materials are ePTFE, polyurethane, silicone or combinations of these materials manufactured in such a way as to render the outer wall surface of the conduit porous. The porous nature facilitates tissue in-growth, which can help to reduce infection rates. It is believed that a porosity of about 20 µm or less in a material provides leak-resistance of the bulk material before needle puncture. Therefore it is preferred but not required that at least a portion of the wall thickness be constructed of a material with a porosity of about 20 µm or less. However, porosities of about 10 µm to about 1000 µm or more on the outer surface may facilitate cellular ingrowth into a porous surface that will reduce serous fluid accumulation surrounding the implant, which in turn reduces the infection rate associated with needle puncture. More preferably, porosities of about 20 µm to about 200 µm, and most preferably about 100 µm to about 200 µm are used. To provide a material that is leak-resistant and has improved cellular ingrowth, a multi-layer material may be provided, with a surface layer having a porosity and/or or other features for facilitating cellular ingrowth, and a subsurface material with features for facilitating leak-resistance. However, that cellular-ingrowth may also be achieved with smooth-surface devices through the use of various substrates or therapeutic agents coated onto the graft and/or catheter section. Furthermore, in regions of the VAS not intended for needle puncture, those regions may be provided with a porous layer or coating to facilitate tissue ingrowth without requiring a leak-resistant sub-layer. These materials are also biocompatible and may be manufactured, for example, so that they have a comparable compliance to the arteries to which they are attached to facilitate the creation and patency of the arterial anastomosis. The inner and outer surfaces of the conduit may also be of different materials, surface structure, and possess coatings to enhance reactions with the body such as patency, infection resistance, and tissue ingrowth.

1. Graft Section

As previously mentioned, the graft section of the vascular access system may comprise ePTFE, polyurethane, silicone, Dacron® or other similar material. The graft section 102 of the VAS 100 may have a length of at least about 20 cm, preferably greater than about 40 cm, and most preferably greater than about 60 cm. The graft section 102 may have an inside diameter within the range of from about 5.5 mm to about 6.5 mm, and sometimes about 5 mm to about 7 mm. The wall thickness of the graft section 102 may be about 0.3 mm to about 2 mm, sometimes about 0.4 mm to about 1 mm, and preferably about 0.5 mm to about 0.8 mm.

As mentioned previously, strain relief is provided in some embodiments of the invention. Strain relief may be advantageous for conduits or grafts that comprise PTFE or other flexible materials and may prevent occlusion of the conduit or graft. In some embodiments, such as those illustrated in FIGS. 4 to 10, the strain relief structure typically comprises a flexible spiral or coil that extends from an end of the connector 2 or connector sleeve 44 and onto the outer surface of or within the wall of the conduit/graft 12. The strain relief structure may comprise a biocompatible metal or plastic.

Figure 17:
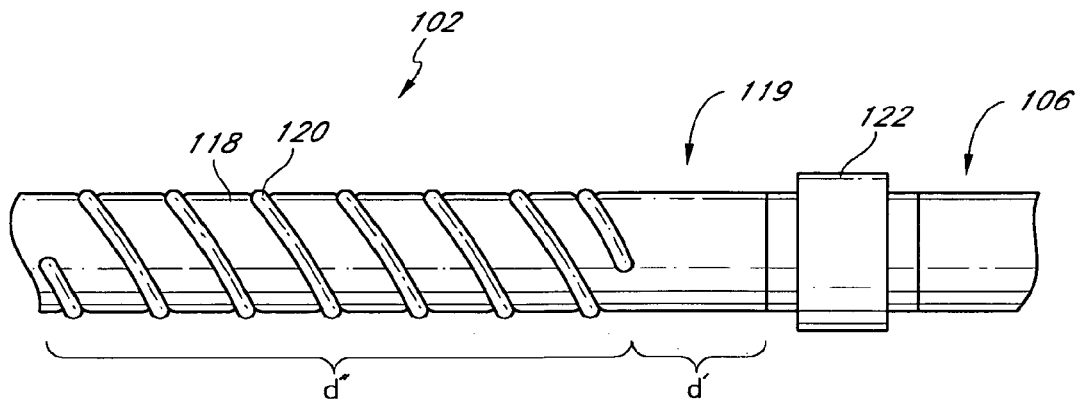
FIG. 17 is an elevational view of a graft section with an anti-kink support.

In an alternate embodiment of the invention, rather than providing a strain relief structure projecting from the connector or connector sleeve onto the graft section, the strain relief structure may be attached directly to the graft section. In one particular embodiment depicted in FIG. 17, the graft section 102 comprises ePTFE material 118 with a PTFE spiral strain relief structure 120 generally located at the connector end 119 of the graft section 102 that is attached or attachable to the catheter section 106 or conduit connector 122 of the vascular access system (VAS) 100. The embodiment depicted in FIG. 17 is a spiral strain relief structure 120, but one of ordinary skill in the art will understand that other strain relief structures may also be attached to the graft section 102. In some instances, the spiral PTFE support is configured to terminate generally at the connector end of the graft section, while in other embodiments, the spiral strain relief structure may extend beyond the end of the graft section to contact the connector or connector sleeve. In other embodiments, the spiral PTFE support is spaced within about 0.2 cm from the connector end 119 of the graft section 102. The spiral PTFE support may have a length of about 1 cm to about 8 cm, preferably about 2 cm to about 6 cm, and most preferably about 2 cm to about 4 cm. The spiral PTFE support may be staked (cold, heat, thermal, and/or ultrasonic) to the PTFE graft material, bonded to the graft material using an adhesive, or held in place by a coating on the graft section 102.

In another embodiment, the graft material is coated and/or embedded with silicone or other elastic material in the region near the connector to improve contact of the wall of the graft with the connector when graft is subjected to bending. This may be beneficial because the ePTFE graft material is naturally plastically deformable and, when it is subjected to a bend at the end of the connector, it may open up a gap that will disrupt blood flow (causing turbulence and pooling) and result in clot formation. The addition of elastic material may help maintain a tighter fit between the graft and connector surface. In one preferred embodiment, the graft is spray or dip coated using a silicone-xylene blend having a viscosity of approximately 200 cps. The viscosity may range from about 50 to about 1000 cps, more preferably about 100 to about 300 cps, and most preferably from about 150 to about 250 cps. Alternatives include low viscosity silicones, urethanes, styrenic block copolymers or other elastomers without solvents or with xylenes, toluenes, napthas, ketones, THF or other suitable miscible solvents.

The graft section of the VAS may optionally have length markers on its surface to facilitate trimming of the graft section to a desired length for individualizing the device to a particular patient's anatomy. The length markers or other markers provided in the graft section may also be radio-opaque to facilitate radiographic visualization of the graft section.

2. Catheter Section

As previously mentioned, the catheter section of the VAS may comprise a conduit having a non-uniform diameter. The end of the catheter section adapted for insertion into a vein or other blood vessel may have an inside diameter of about 3 mm to about 10 mm, sometimes within the range of about 4 mm to about 6 mm, and preferably about 5 mm, and may have an embedded or external spiral support to provide kink resistance. The end of the catheter section adapted for attachment to a connector or graft section may have a larger diameter because it does not reside within the lumen of a blood vessel. The selection of the inner diameter, outer diameter and length of the catheter section may be selected by one skilled in the art, based upon factors including but not limited to the vein into which the second body fluid segment is being inserted into, the length of catheter to be inserted through the vein wall, as well as the desired flow rate and fluid resistance characteristics.

The catheter section typically comprises PTFE, polyurethane or silicone. Other biocompatible materials that may be used include polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene, biocompatible elastomers such as medical grade silicone rubbers, polyvinyl chloride elastomers, polyolefin homopolymeric and copolymeric elastomers, styrene-butadiene copolymers, urethane-based elastomers, and natural rubber or other synthetic rubbers, and other similar compounds known to those of ordinary skilled in the art. See Polymer Handbook, Fourth Edition, Ed. By J. Brandup, E. H. Immergut, E. A. Grulke and D. Bloch, Wiley-Interscience, NY, Feb. 22, 1999.

Preferably the portion of the catheter section that is insertable into the vein is sized to allow collateral flow of blood around the inserted catheter and through the vascular site where the catheter section is inserted. It is also preferred in some embodiments that the catheter section of the VAS be dimensioned to allow percutaneous insertion of the catheter section into a vein using the Seldinger technique, rather than by venous cutdown or full surgical exposure of the vein. Percutaneous insertion of the catheter section into a vein, such as an internal jugular vein, for example, is facilitated by a catheter section having an outer diameter of no greater than about 6 mm, and preferably no greater than about 5 mm or about 4 mm.

In one embodiment of the invention, the catheter section of the VAS is reinforced with polymeric filament, metallic wire or fibers, or combination thereof, and preferably in a spiral configuration. Reinforcement of the insertion segment of the VAS, especially with metallic wire or fibers, may be used to provide an insertion segment with a reduced outer diameter and one that has improved anti-kink and/or crush-resistant properties compared to a similar catheter section lacking reinforcement. The wire or line may be bonded to the outer or inner surface of the catheter section, or may be extruded with or molded into the silastic material to form the catheter section. In some embodiments, a spiral wire is placed or bonded to the outer surface of a conduit material and then spray or dip coated with a material to provide a smooth outer surface that is not interrupted by the wire reinforcement. One of skill in the art will understand that other reinforcement configurations besides a spiral configuration may be used, including discrete or interconnected rings, circumferential and/or longitudinal fibers that may be aligned, staggered or randomly positioned in or on the walls of the VAS.

In one example, the catheter section comprises a silicone extruded tube with a nylon winding for reinforcement. The silicone may contain from about 1% barium to about 30% barium to improve the radio-opacity of the catheter section. In other embodiments, the silicone may contain from about 5% to about 20% barium, and in still other embodiments, the silicone may contain from about 10% to about 15% barium. Other radio-opaque materials may be substituted for barium or used in addition to barium. The nylon winding may comprise a nylon monofilament with a diameter of about 0.005 inch diameter to about 0.050 inch diameter, and preferably about 0.010 inch to about 0.025 inch diameter. The winding may be configured for a wrap of about 10 to about 60 per inch, preferably about 20 to about 40 per inch. Silicone over molding, step up molding and/or silicone spray may also be used to provide a more consistent and/or smoother outer diameter over the portions of the catheter section.

Figure 18A:
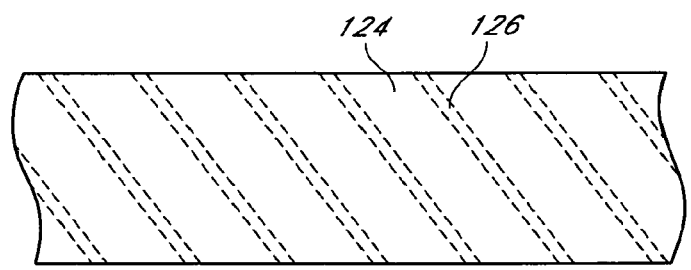
FIGS. 18A and 18B are schematic elevation and cross-sectional views, respectively, of one embodiment of a catheter section with embedded reinforcement.
Figure 18B:
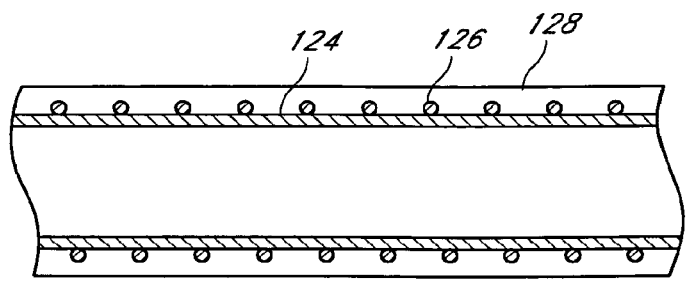

In another example illustrated in FIGS. 18A and 18B, the catheter section 106 comprises a silicone tube 124 with Nitinol winding 126 for reinforcement. The Nitinol winding 126 may have a diameter of about 0.002 inch diameter to about 0.020 inch diameter, and preferably about 0.003 inch diameter to about 012 inch diameter. The Nitinol winding 126 may be configured for a wrap of about 10 to about 100 per inch, and preferably about 20 to about 60 per inch. The outer surface of the catheter section 106 is sprayed with silicone 128 to provide a more uniform and smoother outer diameter.

It is well known to one skilled in the art that a radio-opaque marker band may be placed at the distal end of the catheter to improve the surgeon's ability to place the catheter tip at a desired location. However, current marker bands are made of a solid ring/band of radio-opaque material, such as platinum or gold, which may become permanently deformed if it is inadvertently compressed or squished. Referring to FIG. 35B, to improve the crush resilience of the marker band, the marker band 300 may be composed of two or more bands 302 or loops of metal stacked or layered on top of each other until a total material thickness is reached that achieves the desired radio-opacity.

For instance, two or more layers of a flat (thin and wide) ribbon may be wrapped on the tip of a catheter to produce the desired radio-opacity. The reason the crush resilience is improved is that the amount of flex that a material can withstand before it becomes permanently deformed is proportional to the thickness (because the material strain is proportional to thickness). For instance, by halving the thickness, the amount of flex is doubled before permanent deformation occurs. It is preferred that the individual layers should not be substantially adhered to one another; otherwise the effective thickness will be increased and the crush-resilience may be diminished. Thus, in the preferred embodiment, a minimum of two layers of 90% platinum/10% iridium ribbon wire are embedded within the tip of the catheter. The wire dimension is preferably about 0.0005 to about 0.001 inch thick by about 0.003 to about 0.010 inch wide. However other dimensions may also be used.

In one specific embodiment, the catheter section of the VAS comprises an insertion segment reinforced with spiral Nitinol wire, and a connecting segment reinforced with polymeric spiral filament. The insertion segment of the catheter section is adapted to be inserted into a vein while the connecting segment is adapted for attachment to a conduit connector and/or to the graft section of the VAS. By using metal wire for the insertion segment of the catheter section, smaller outer diameters may be achieved to facilitate insertion of the catheter section of the VAS through the skin and into a vein or other blood vessel. On the other hand, by providing polymeric reinforcement of the connecting segment, the diameter of the connecting segment may be reduced while maintaining the ability to trim the connecting segment of the catheter section without creating a sharp end or burr that may result when cutting through a metal wire reinforced portion of the catheter section. The insertion segment may have a length of about 10 cm to about 50 cm, preferably about 15 cm to about 35 cm, and most preferably about 20 cm to about 25 cm. The connecting segment of the catheter section can have a pre-trimmed length of about 10 cm to about 50 cm, preferably about 15 cm to about 35 cm, and most preferably about 20 cm to about 25 cm. In some embodiments of the invention, the total length of the catheter section is about 20 cm to about 250 cm, sometimes about 30 cm to about 60 cm, and other times about 120 cm to about 250 cm. Longer lengths may be used when implanting the device between axillary/femoral sites.

Figure 19A:
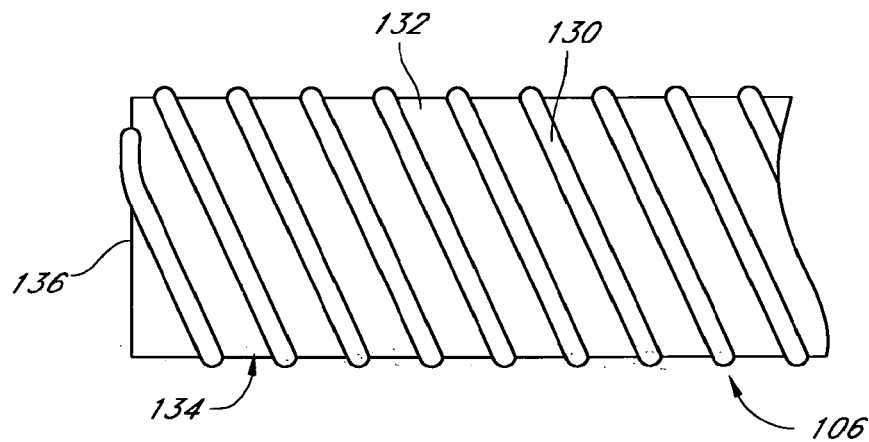
FIGS. 19A to 19C are detailed elevational views of one embodiment of a catheter section reinforced with a removably bonded filament.
Figure 19B:
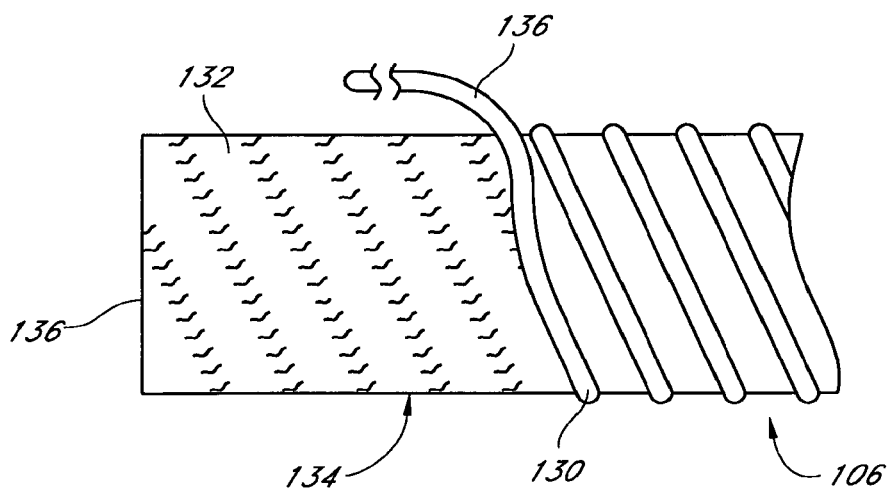
Figure 19C:
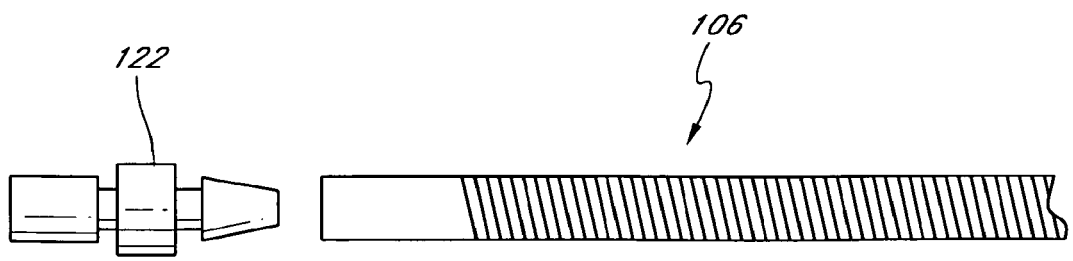

In further embodiments of the invention, depicted in FIG. 19A, the polymeric reinforcement 130 of the catheter section 106 is bonded or adhered to the outer surface 132 of the connecting segment 134, rather than embedded within the wall of the connecting segment 134. In some embodiments, such as those in FIGS. 19A and 19B, the polymeric reinforcement 130 is also bonded or adhered in a manner that allows the controlled peeling or separation of a portion of the polymeric reinforcement 130 from the outer surface 132 of the connecting segment 134, without damaging or violating the integrity of the remaining structure of the connecting segment 134. Referring to FIG. 19C, this feature may be beneficial in embodiments of the invention where the polymeric spiral reinforcement 134 resists or prevents the radial expansion of the connecting end 136 needed in order to fit the end of the connecting end 136 over a conduit connector 122. By allowing the controlled removal of a portion of the polymeric reinforcement 130, after trimming the connecting segment 134 of the catheter section 106 to its desired length, a portion 136 of the polymeric reinforcement 130 may be removed from the connecting segment 124 in order to prepare the catheter section 106 for fitting to a conduit connector 122 or an integrated connector on a graft section of a VAS. In a similar fashion, the reinforcement may preferably be embedded in the catheter wall but close to the outer surface to enable easy removal.

To reduce the risk of damage to the catheter section and/or blood vessel structures where the catheter section is inserted, and/or to reduce the turbulent blood flow at the distal opening of the catheter section, the edge of the distal tip of the catheter section may be rounded. In some embodiments, rounding may be performed with a silicone dip or shadow spray, or may be molded to a round shape.

Figure 35A:
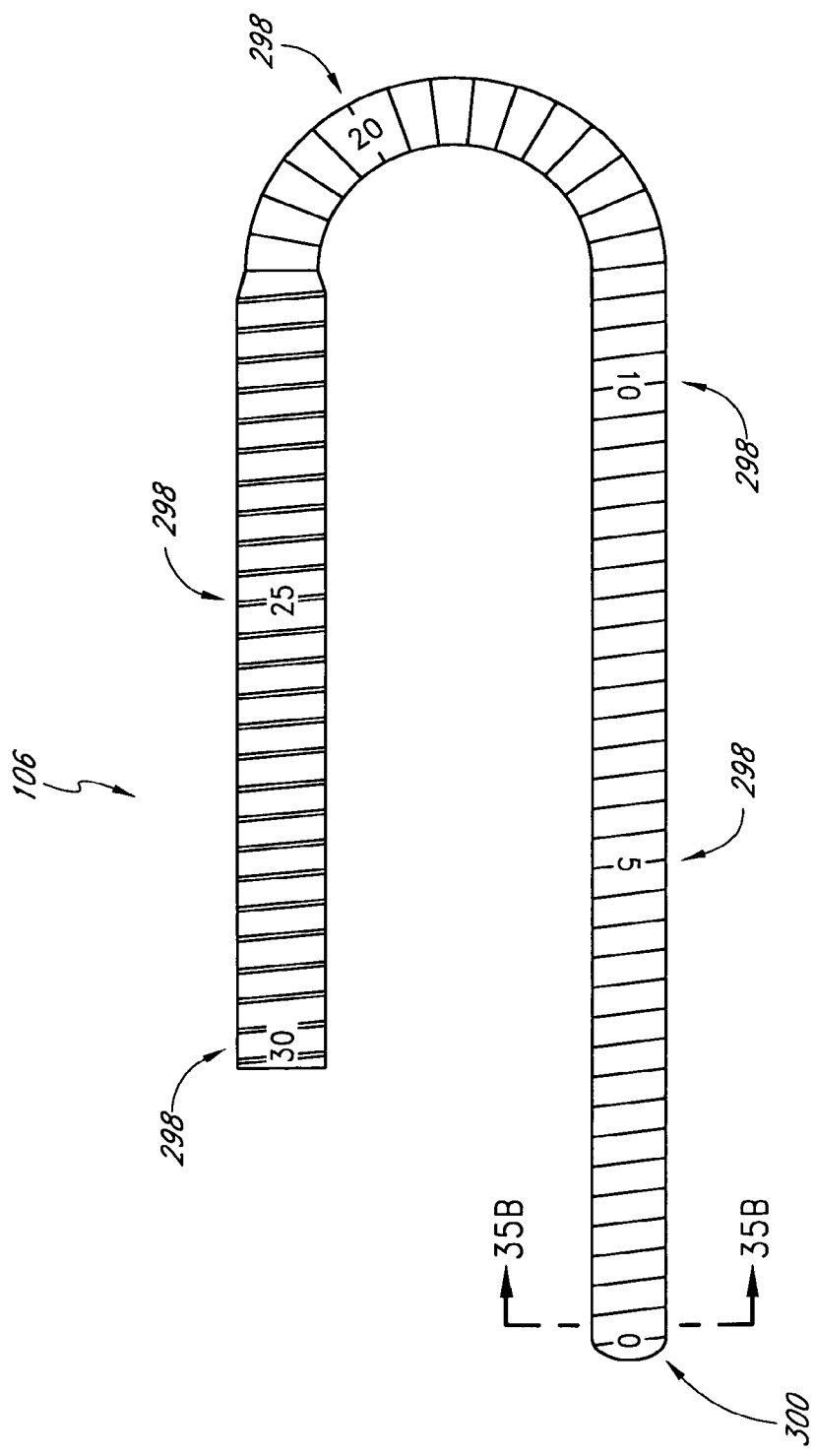
FIG. 35A depicts one embodiment of the invention comprising length markers and a crush-resilient radio-opaque marker.
Figure 35B:
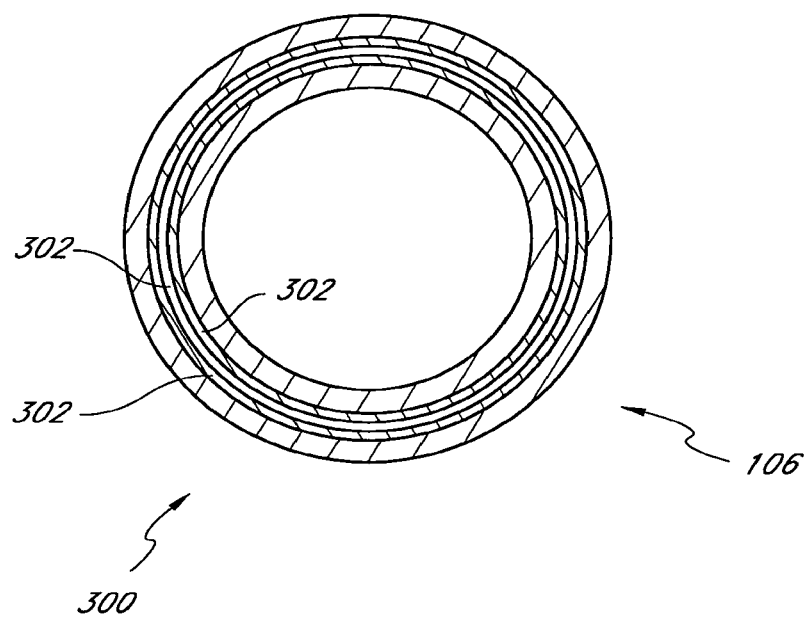
FIG. 35B is a cross-sectional view of the crush-resilient radio-opaque marker.

Referring to FIG. 35A, as with the graft section of the VAS, the catheter section 106 may optionally have length markers 298 on its surface to facilitate trimming of the catheter section 106 to a desired length for individualizing the device to a particular patient's anatomy. The length markers or other markers provided in the catheter section may also be radio-opaque to facilitate radiographic visualization of the catheter section. Likewise, the catheter section may be coated with one or more therapeutic agents to treat any of a variety of VAS related effects, including but not limited to resisting thrombosis and/or reducing infection.

3. Improved Strain Relief

As described above, the catheter and/or graft sections of the VAS may be provided with strain relief support to prevent or resist kinking that may occur around their connections with the conduit connector.

The use of a tapered strain relief to prevent kinking when a flexible tube or cable is connected to a rigid connector is well known. However, even when the taper transitions to a near-zero wall thickness, the end of the strain relief is often able to produce a force on the flexible conduit that can kink the conduit. The problem may relate to the observation that the flexural resistance of the strain relief structure is dominated by the diameter of the strain relief (e.g. the flexibility is roughly proportional to the diameter to the $4^{th}$ power). Since the diameter of the strain relief needs to be bigger than the tube in order to slide over the outside of tube, it tends to increase stiffness abruptly at this region. When flexural stiffness changes abruptly, it may produce a region that is prone to kinking.

Figure 22A:
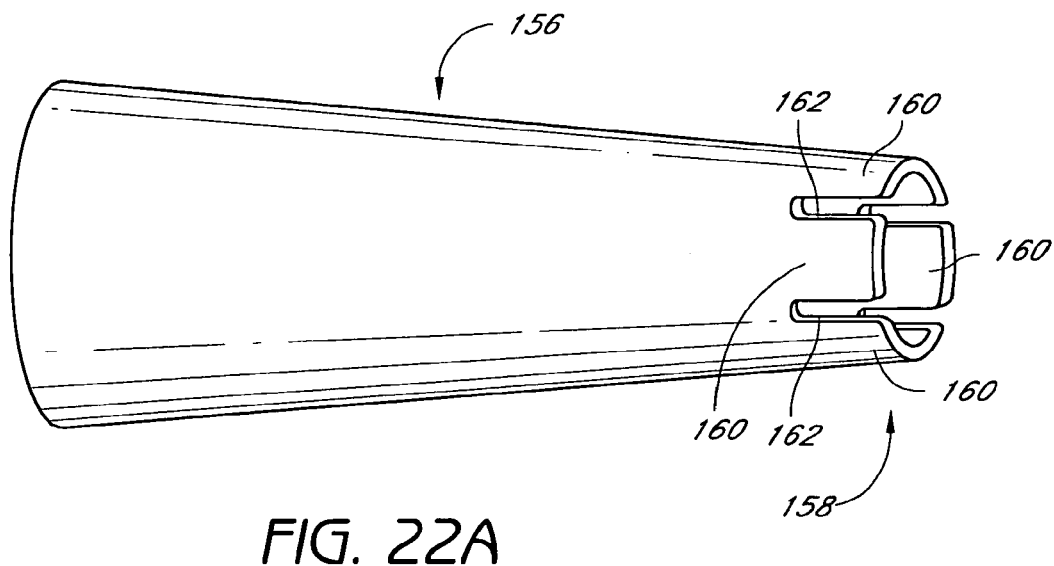
FIGS. 22A and 22B are elevational and cross sectional views, respectively, of one embodiment of a strain relief structure.
Figure 22B:
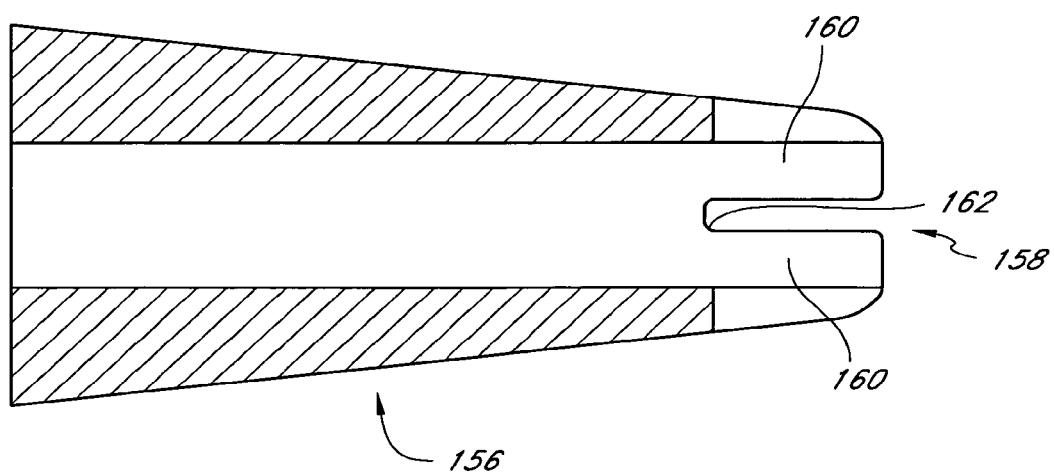

One embodiment of the invention, depicted in FIGS. 22A and 22B, provides a strain relief structure 156 that reduces such kink points with a "flower" configuration at the end 158 of the strain relief 156 (e.g. split the end of the strain relief into flexural sections 160, thus reducing or eliminating the problem caused by the diameter disparity) to produce a very gradual change in flexibility. In some embodiments, these flexural sections 160 may have a tapered thickness and/or width to gradually increase the flexural stiffness along their length. In addition, the number of flexural sections 160 may be varied in order to tailor the strain relief's flexibility to that of the tube. The separations 162 between the flexural sections 160 are preferably rounded, or even looped with larger base opening. A rounded or looped configuration is more resistant to tearing from movement of the flexural sections 160 than straight separations between the flexural sections 160. The slits are preferably about 0 to about 0.100 inch wide, and more preferably about 0.040 to about 0.080 inch wide. The length is preferably about 0.100 to about 0.500 inch long, and more preferably about 0.200 to about 0.300 inch long. The number of slits is preferably about 3 to about 8, and most preferably about 4. The preferable material is flexible and biocompatible, such as silicone or polyurethane, but other materials may be used. Other biocompatible materials that may be used include polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene, biocompatible elastomers such as medical grade silicone rubbers, polyvinyl chloride elastomers, polyolefin homopolymeric and copolymeric elastomers, styrene-butadiene copolymers, urethane-based elastomers, and natural rubber or other synthetic rubbers, and other similar compounds known to those of ordinary skilled in the art. Polymer Handbook, Fourth Edition, Ed. By J. Brandup, E. H. Immergut, E. A. Grulke and D. Bloch, Wiley-Interscience, NY, Feb. 22, 1999.

4. Improved Crimping

Figure 34A:
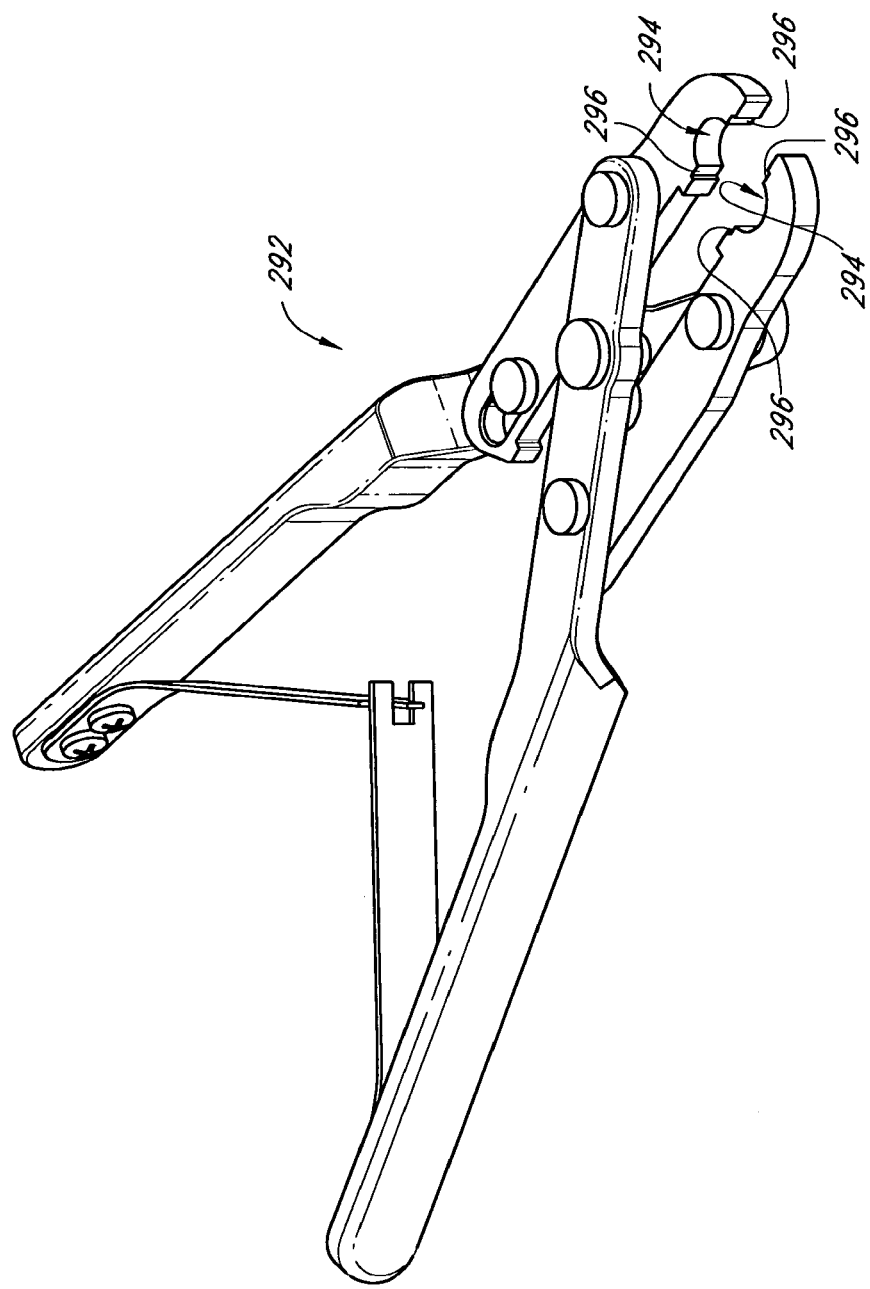
FIGS. 34A and 34B are oblique elevational views of one embodiment of the invention comprising a crimping tool for securing portions of the vascular access system to a connector.
Figure 34B:
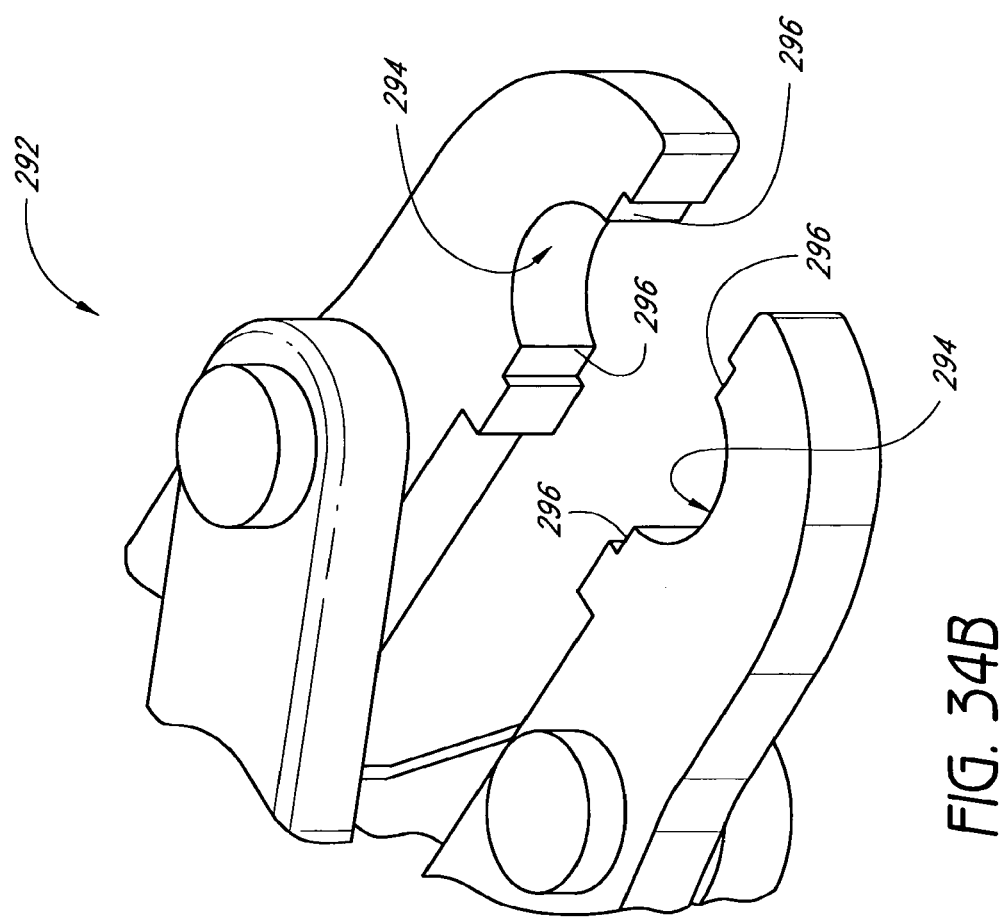

As previously disclosed, the graft and/or catheter sections of the VAS may be attached to a conduit connector using a variety of structures, including crimp rings. One of ordinary skill in the art will understand that many crimping methods may be suitably used for the invention. In one particular embodiment, the crimp ring, following the crimping procedure, comprises one or more protrusions on its outer surface. These projections provided friction sites for resisting displacement of a connector sleeve that may be overlying the crimp ring(s). Referring to FIGS. 34A and 34B, one embodiment of the invention for such a crimp ring may comprise a crimp tool 292 with crimping surfaces 294 with one or more indentations 292. The indentations 296 allow one or more portions of the crimp ring to project outwardly during the crimp process.

5. Implantation of the Vascular Access System

In some embodiments of the invention, the low profile of the VAS, combined with the ease of inserting the catheter section of the VAS into the vasculature, allows the use of a minimally invasive procedure to implant the device in the body. Depending upon the diameter of the catheter section of the VAS, the catheter section may be inserted into the vein using an open surgery technique, or preferably a venous cut-down, or most preferably by Seldinger technique. These techniques are well known procedures to those of ordinary skill in the art.

Once the insertion site of the catheter section of the VAS is established, a subcutaneous pathway from the catheter section insertion site to the desired graft section attachment site may be created using any of a variety of specialized tunneling instruments or other blunt dissection tools. The VAS system is then passed through the subcutaneous pathway and the graft section is attached to the desired site. A single, uninterrupted subcutaneous pathway may be created between the insertion site and attachment site of the VAS, particularly where the VAS device comprises a unibody design. Depending upon the sites selected, the particular anatomy of a patient, the tortuosity of the desired subcutaneous pathway, and/or the modularity of the VAS, it may be desirable to create one or more intermediate surface access sites along the subcutaneous pathway to make it easier to perform the subcutaneous tunneling and/or to pass one or more sections of the VAS along the pathway. The use of intermediate surface access sites is particularly desirable, but not necessary, when implanting a multi-section VAS. The individual sections of the VAS may be implanted separately along the sections of the subcutaneous pathway, and then attached via conduit connectors or other structures at the intermediate surface access points and then buried subcutaneously.

Figure 23A:
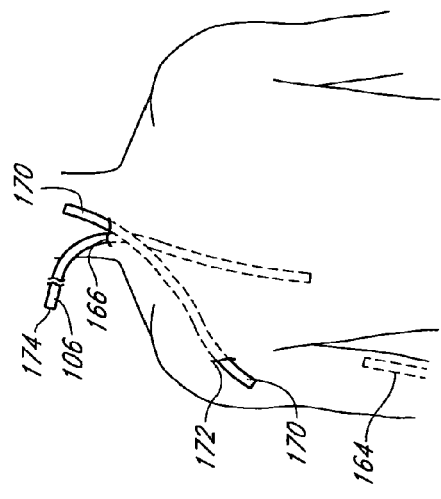
FIGS. 23A to 23F are schematic representations of one embodiment of the invention for implanting a two-section vascular access system.

Referring to FIGS. 23A to 23F, in one embodiment of the invention, the patient is prepped and draped in the usual sterile fashion. Either local or general anesthesia is achieved. In FIG. 23A, the brachial artery is palpated on the patient and terminal access site 164 is marked. The internal jugular (IJ) vein is located and an initial access site 166 to the IJ vein is selected using anatomical landmarks and/or radiographic visualization such as ultrasound. A guidewire is passed into the IJ vein and then a dilator is passed over the guidewire to facilitate insertion of an introducer into the IJ vein. A small scalpel incision may be needed at the guidewire insertion site if the skin and/or subcutaneous tissue create excessive resistance to the insertion of the dilator. The dilator is removed and an introducer 168 is inserted over the guidewire and into the IJ vein. The introducer 168 may be a standard or custom type of introducer. The catheter section 106 of the VAS is then inserted into the introducer, through the IJ vein and into the superior vena cava or right atrium. The position of the distal tip of the catheter section 106 is confirmed radiographically and the patient is checked for accidental collapse of the lung due to improper insertion. The introducer 168 is then removed, either by pulling the introducer over the proximal end of the catheter section, if possible, or by peeling away the introducer if a peel-away introducer was provided.

Figure 23B:
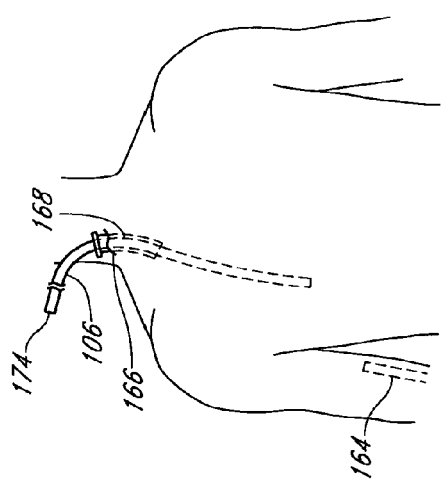
Figure 23C:
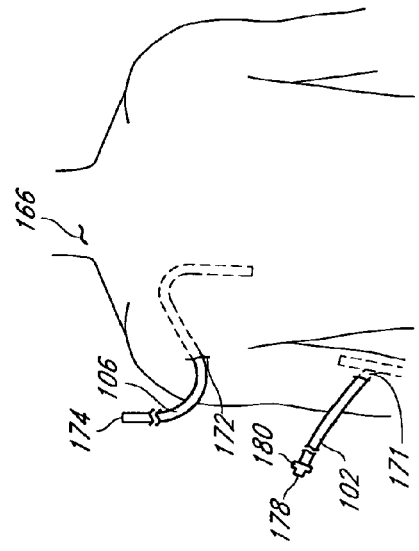
Figure 23D:
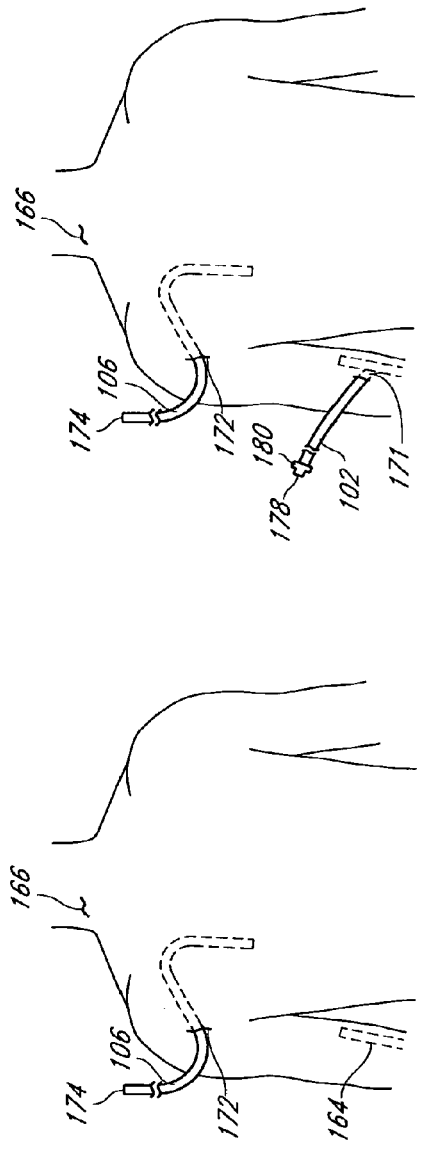
Figure 23F:
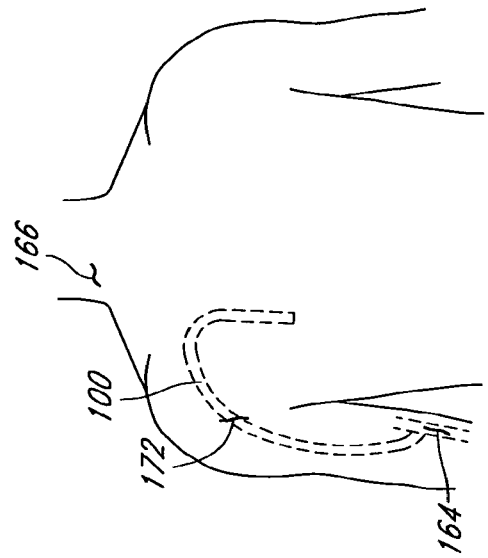
Figure 23E:
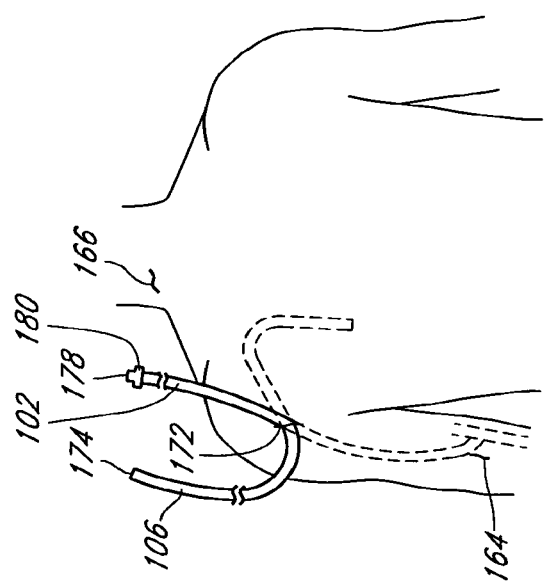

In FIG. 23B, a surgical rod 170 is then inserted into the subcutaneous space through the initial access site. The rod 170 is used to subcutaneously tunnel toward the anterior shoulder. In other embodiments, the subcutaneous tunneling and implantation of the VAS section may occur generally simultaneously. Once the anterior shoulder is reached, a scalpel is used to create an intermediate access site 172 to the rod 170. In FIG. 23C, the rod 170 is removed from the initial access site 166 and then the proximal end 174 of the catheter section 106 is passed through the subcutaneous pathway to exit from the intermediate access site 172. The same surgical rod 170 or a different rod is then inserted into the intermediate access site 172 and used to subcutaneously tunnel distally down the arm until the marked brachial artery site is reached. A terminal access site 164 to the rod is created and further exposed to access the brachial artery. The anastomosis end 171 of the graft section 102 of the VAS is attached to the brachial artery, as illustrated in FIG. 23D. Alternatively, the anastomosis may be performed after the graft section 102 is subcutaneously positioned. Referring next to FIG. 23E, the connector end 178 of the graft section 102, with pre-attached conduit connector 180, is passed from the terminal access site 164 to the intermediate access site 172. A connector sleeve with integrated strain relief structure may be passed over the proximal end 170 of the catheter section 172. The initial and terminal access sites 166, 164 are checked for any redundant conduit and pulled taut from the intermediate access site 172 if needed. The proximal end 174 of the catheter section 106 is trimmed to the desired length. About 0.5 cm to about 1 cm segment of nylon winding at the trimmed end of the catheter section is separated and cut away. The proximal end 174 of the catheter section 106 is fitted to the pre-attached conduit connector 180 of the graft section 102. The catheter section 106 is secured to the conduit connector 180 with a crimp ring and the connector sleeve is repositioned over the conduit connector. The exposed portions of the conduit connector 180, attached to the distal end 178 of the graft section 102 and the proximal end 174 of the catheter section 106, are either pulled from the graft end or pushed into the subcutaneous space through the intermediate access point 172, as illustrated in FIG. 23F. Flow through the VAS 100 is reconfirmed either by palpation or preferably by ultrasound and/or angiography. The three access sites 164, 166, 172 are sutured closed. The implanted VAS 100 is then accessed with hemodialysis needles to perform hemodialysis.

Figure 37B:
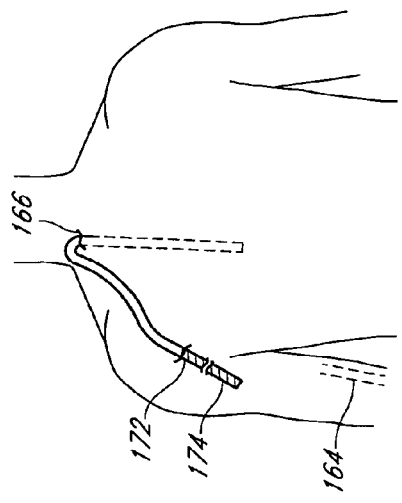
Figure 37A:
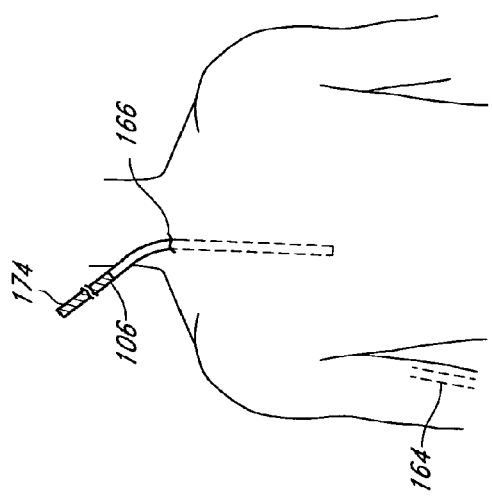
Figure 37D:
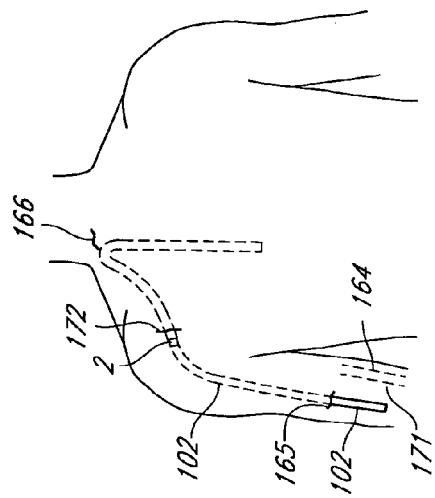
Figure 37C:
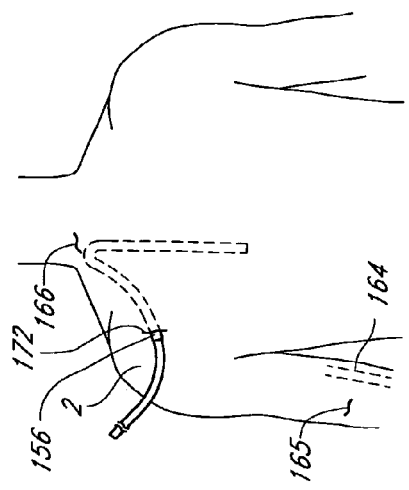

In a preferred embodiment of the invention, depicted in FIGS. 37A to 37E, the patient is placed under general anesthesia and the graft routing is marked on patient arm. The surgical site prepped, sterilized and draped. An incision 166 is made in the neck to access the lower portion of internal jugular vein. A small wire is inserted through the access site 166. The small wire is exchanged with a mid-sized introducer set (about 5 F to about 14 F) and the wire is removed. The vein may be angiographically assessed, and if a stenosis is identified that may preclude advancement of catheter, angioplasty may be used to enlarge the lumen of the vein. A larger wire is inserted through mid-sized introducer. The mid-sized introducer is exchanged with 20 F introducer. The patient is preferably placed in Trendelenberg position prior to the removal of the dilator to reduce the propensity for air introduction upon catheter insertion. The dilator and clamp introducer is removed and the introducer is closed off with a finger. The catheter 106 is filled with heparinzed saline, clamped and inserted through the introducer. The ventilator may be optionally turned off while catheter is inserted to reduce the propensity for introduction of air. The introducer is peeled away, leaving the catheter 106 in the IJ, as shown in FIG. 37A. A "Christmas Tree" valve or atraumatic clamp (preferably a Fogarty's clamp) may be used to stop back bleed through catheter. The patient may be brought out of Trendelenberg position. The position of the catheter tip is checked under fluoroscopy for a position in the proximal to mid-right atrium (RA), and is adjusted if needed. To tunnel the catheter subcutaneously, a delta-pectoral incision 172 is made, as shown in FIG. 37B. The catheter 106 is then tunneled to the delta-pectoral incision 172 by routing above the sternocleidomastoid muscle in a sweeping fashion. Depending upon the characteristics of the catheter 106, in some instances care should be taken to not create a bend in the catheter 106 with a diameter less than about 2.5 cm to avoid kinking. The nylon filament on the catheter 106 is wound down and the catheter 106 is cut to leave approximately an inch outside of delta-pectoral incision 172. An appropriate amount of nylon winding is removed in comparison to the length of the barb on the connector 2. A connector sleeve 156 (flower end first) and crimp ring are placed over the catheter, typically in that order, depending upon the particular securing mechanism used. As depicted in FIG. 37C, the connector 2, pre-attached to the graft 102, is then attached to the catheter 106, and the catheter 106 is secured to the connector 2 using the crimp ring. The connection is tested to ensure integrity. The connector sleeve is 156 placed over most if not all the exposed metal surfaces. A brachial incision 164 is made to expose the brachial artery. An auxiliary incision site 165 is made lateral to the brachial incision site 164. The graft 102 is tunneled from the delta-pectoral site 172 or connector incision site in a lateral-inferior direction until reaching the lateral aspect of the arm. It is preferable but not required to stay superficial and also lateral to the bicep muscle. Tunneling is continued inferiorly until the auxiliary incision site 165 is reached. A tunnel from the auxiliary site 165 to the brachial site 164 is then performed to create a short upper arm loop in a "J" configuration 167 just proximal to the elbow. The graft is then tunneled cephalad along the medial aspect of the upper arm to the brachial incision site 164. Preferably, the graft 102 should be parallel to the brachial artery to allow construction of a spatulated anastomosis. The orientation line or marks are checked for an orientation in the same direction at both ends 171, 178 of the graft 102 and to verify that the catheter 106 has not moved from the proximal RA. The graft 102 is checked for a sufficient amount of slack. A parallel end-to-side anastomosis is then constructed by cutting the graft at an oblique angle and making an arteriotomy along the long axis of the brachial artery. This may be advantageous as it may cause less turbulence at the anastomotic site and may be less prone to stressing the anastomosis. The anastomosis between the artery and graft is then performed as known to those of ordinary skill in the art, as shown in FIG. 37E. A Doppler scan of the lower right arm and hand may be performed prior to closing to check whether steal syndrome occurs with the shunt. The anastomosis is checked angiographically via back-filling along the length of the VAS. Tip placement in the RA and VAS integrity with movement of the subject's arm may also be checked. Patency and absence of significant bends or kinks is also checked. The incisions are closed and dressed.

Although the embodiment described above utilizes the internal jugular vein and the brachial artery as the insertion and attachment sites, respectively, of the graft system, one with skill in the art will understand that other insertion and attachment sites may be used, and were described previously above. For example, other arteries that may be used with the invention include but are not limited to the ulnar artery, radial artery, femoral artery, tibial artery, aorta, axillary artery and subclavian artery. Other venous attachments sites may be located at the cephalic vein, basilic vein, median cubital vein, axillary vein, subclavian vein, external jugular vein, femoral vein, saphenous vein, inferior vena cava, and the superior vena cava. It is also contemplated the implantation of the device may be varied to configure the graft system in a generally linear configuration or a loop configuration, and that the insertion and attachment sites of the invention need not be in close proximity on the body. For example, attachment and insertion of the device may be performed at an axillary artery and femoral vein, respectively, or from a femoral artery to an axillary vein, respectively.

6. Catheter Inserts for Implanting the Vascular Access System

Figure 24G:
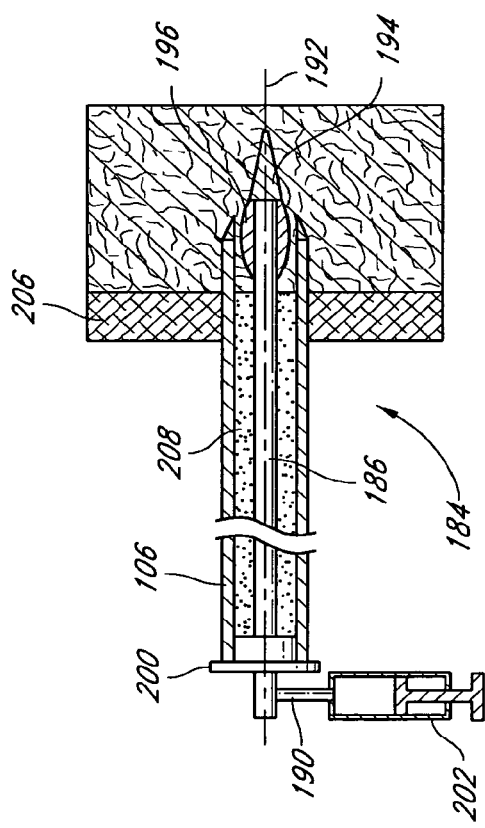
Figure 24H:
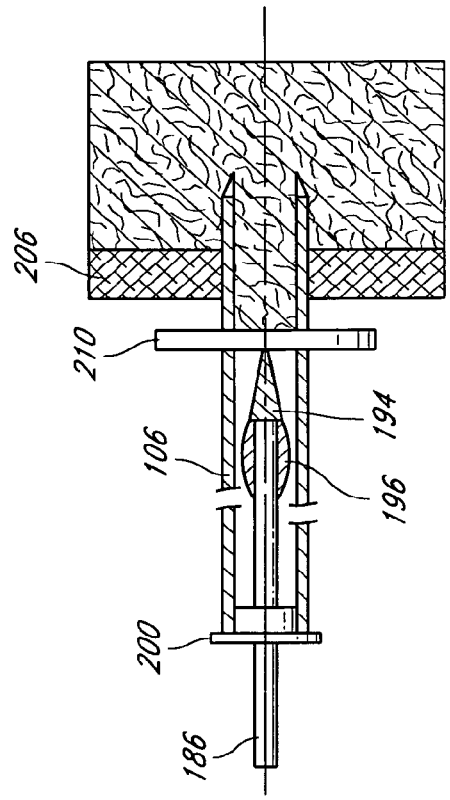
Figure 24I:
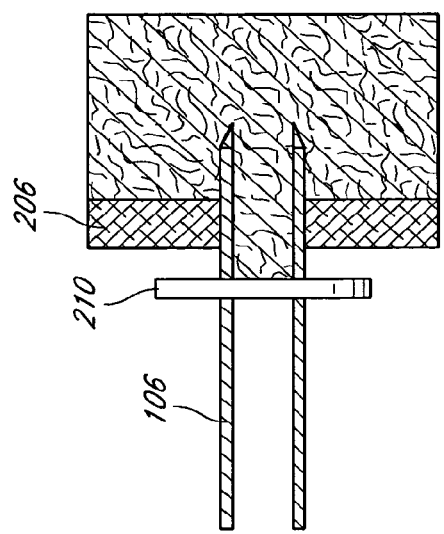
Figure 25B:
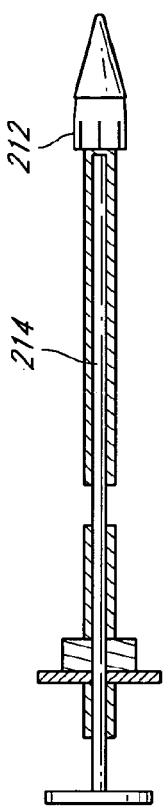
FIGS. 25A and 25B are schematic cross-sectional views of another embodiment of a device for inserting the catheter section of the vascular access system into a blood vessel.
Figure 25A:
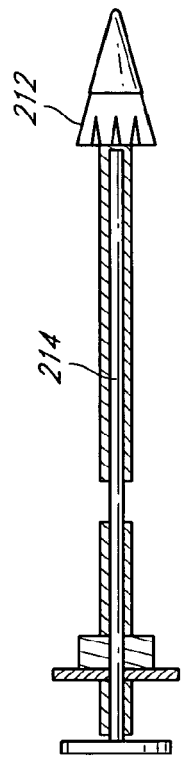

In some embodiments of the invention, specific delivery devices for inserting the VAS to a blood system are contemplated. In one specific embodiment, an insert for the catheter allows the catheter to become its own dilator. The insert is removed after implantation of the VAS. Referring to FIGS. 24A to 24I, the catheter section of the VAS is provided with a distal end 182 having a beveled edge. As illustrated in FIG. 24B, a catheter insert device 184 is provided, comprising an insert shaft 186 with a guidewire lumen 188, an expansion balloon lumen (not shown), an expansion balloon port 190, a guidewire 192, a distal tapered tip 194, an expansion balloon 196, an internal seal 198, a proximal seal 200, and a filling syringe 202. In FIG. 24C, the catheter insert device 184 is inserted into the catheter 106 and the expansion balloon 196 is inflated to preferably seal off the catheter lumen 204 at the beveled tip 182. In FIG. 24D, the catheter 106 and catheter insert 184 are advanced to the wall of a vein 206 by any of the access methods described above. Referring to FIG. 24E, the catheter lumen 204 containing the catheter insert device 184 is filled with saline or other biocompatible fluid, and the guidewire 192 is inserted into the vein. In FIG. 24F, the catheter section 106 and catheter insert 184 are then passed into the vein 206 over the guidewire 192. In FIG. 24G, the expansion balloon 196 is deflated. In FIGS. 24H and 24I, the catheter section 106 is externally compressed with a clamp 210 as the catheter insert 184 is withdrawn from the catheter section 106, to prevent blood leakage from the proximal end of the catheter section 106. The external clamp 210 is released prior to connection of the catheter section 106 to the conduit connector or graft section of the VAS. One of skill in the art will understand that many alternative catheter inserts structures are possible, including a mechanical expansion structure as depicted in FIGS. 25A and 25B, comprising a slotted tapered cylinder 212 and a plunger rod 214 that radially expands the slotted cylinder 212 by providing a radial expansion force as the plunger rod 214 is depressed against the inner surface of the slotted tapered cylinder 212.

C. Instant Access

In some embodiments of the invention, the VAS is configured to provide immediate hemodialysis access upon implantation, while reducing or eliminating the risk of hemorrhage associated with accessing the graft section of the VAS prior to its maturation or without inserting an additional catheter to provide temporary dialysis access. The instant access sites may be provided as subcutaneous needle access sites that use self-sealing materials or other structures to stop the bleeding once the hemodialysis needles are removed. The instant access sites may also comprise temporary catheters attached to VAS that exit the skin to provide external access to the VAS with a further benefit of eliminating the discomfort associated with piercing the skin to achieve hemodialysis access. These and other embodiments of the invention are discussed in further detail below. These embodiments may be well suited for integration into medical devices other than VAS, including but not limited to any of a variety of catheters, needle access ports or intravenous fluid tubing.

1. Instant Access Materials

In one embodiment of the invention, the graft or catheter material may have self-sealing properties. Self-sealing refers generally to at least at portion of the VAS wall having the ability to reseal following puncture with a sharp instrument, such as a needle. A material with self-sealing properties may be used immediately upon implantation, in contrast to traditional graft materials. No biological maturation process to improve the leakage properties of the material is required. A self-sealing material may also reduce the time required to stop bleeding from the access site following removal of the hemodialysis needles. Furthermore, the material may also be used to provide instant access sites at other sections of the VAS, or in other medical products which may benefit from self-sealing properties. The instant access material may be located anywhere along the VAS. In one embodiment of the invention, a low durometer material may be used as an instant access site. In one embodiment of the invention, low durometer materials comprise materials having a hardness of about 10 to about 30 on the Shore A scale, and preferably about 10 to about 20 on the Shore A scale. Other structures with self-sealing properties are described below.

a. Residual Compressive Stress

In one embodiment, the self-sealing conduit material is constructed by spraying a polymer, including silicone, onto a pre-existing tube of conduit material while undergoing various directional strains. The self-sealing material provides mechanical sealing properties in addition to or in lieu of platelet coagulation to seal itself. In one embodiment, the VAS comprises a self-sealing material having two or more alternating layers of residual stress coating.

Figure 20:
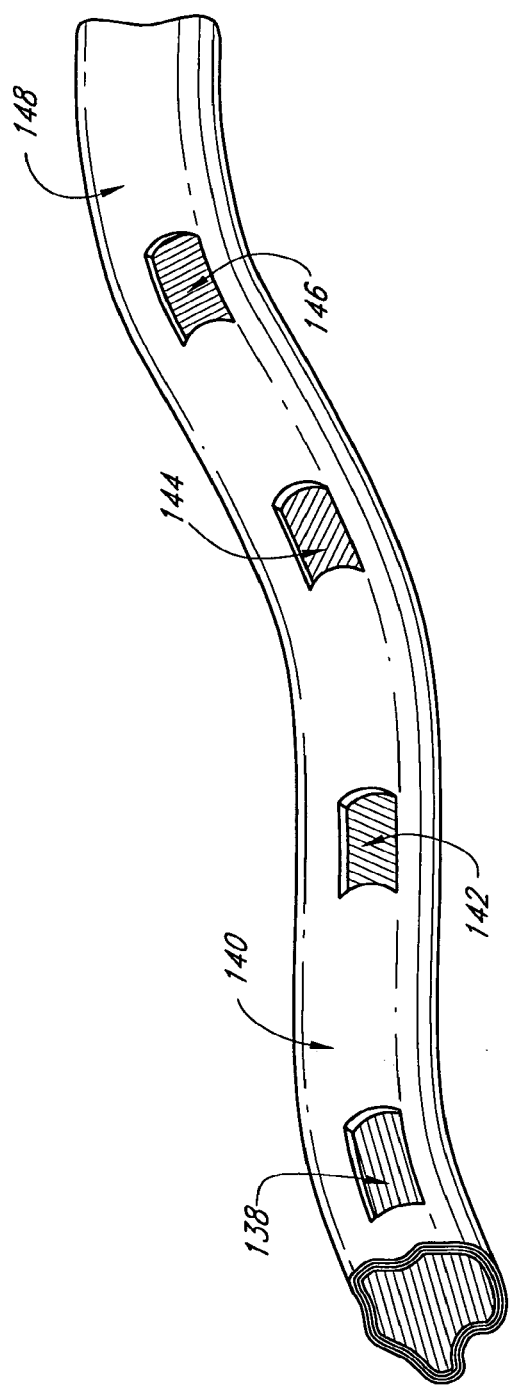
FIG. 20 is a schematic representation of a self-sealing conduit comprising multiple layers.

In one particular embodiment, illustrated in FIG. 20, the conduit material comprises four layers, wherein the inner layer 138 is formed by axially stretching the conduit material 140, spray coating the conduit material and allowing the coating to cure, then releasing the conduit material from tension. The second layer 142 (from inner layer) is formed by twisting the conduit material 142 about its axis, spray coating and curing it, then releasing it from torque. The third layer 144 is formed by taking the conduit material from the previous step and twisting it about its axis in the opposite direction of previous step, spray coating and curing it, then releasing it from torque. The fourth layer 146 is created by taking the product from previous step, expanding it with internal pressure, spray coating and curing it, then relieving the material of pressure. Note that this may also create an axial strain since the tube elongates with pressure. A fifth optional layer 148 of an additional strain coating or a neutral coating may also be provided. The additional layer 148 may aid in achieving consistent outer diameter.

Although one example is provided above for creating a self-sealing graft or catheter material, one of ordinary skill in the art will understand that many variations of the above process may be used to create a self-sealing conduit material. One variation is to produce residual stress in the graft material by inflating and stretching the material to a thin wall and applying polymer to the wall either by dipping or spraying. The amount of circumferential and/or axial stress in the final tube may be controlled separately by adjusting the amount of inflation or axial stretch. Also, the above steps may be performed in a different order, and/or or one or more steps may be repeated or eliminated. Other variations include spraying a mandrel without using a pre-existing tube or turning the conduit material inside out (for compressive hoop stress) for one or more steps.

b. Open, Porous Structure

In another embodiment of the invention, a self-sealing portion of the VAS comprises a porous structure (e.g. material similar to Perma-Seal by Possis Medical or Vectra by Thoratec) in the wall of the VAS catheter or graft. Resistance to blood leakage in this device results from a porous wall design that provides increased surface area to promote blood clotting. In addition, the porous design can recover more readily after a needle has been left in the wall for several hours. The outer surface of the catheter is preferably porous to facilitate in-growth of tissue in order to further facilitate sealing and, more importantly, to minimize the likelihood of infection.

c. Intrawall Gel

Figure 21:
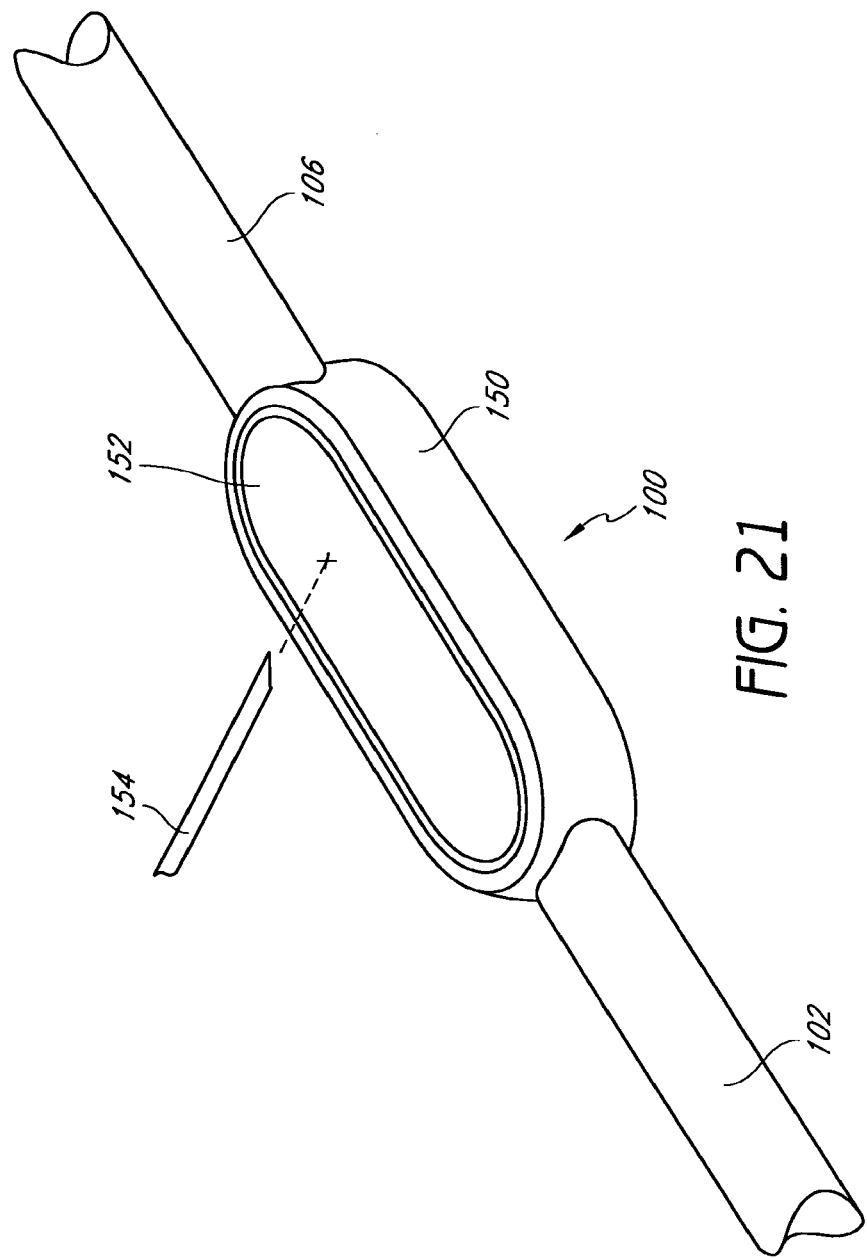
FIG. 21 is an oblique elevational view of an access port.

In another embodiment of the invention, the self-sealing material comprises one or more soft inner gel layers within a wall region of the VAS. The wall region and gel layers are pierceable by a needle. As the needle is removed, the gel seals the needle tract because the gel is flexible and semi-gelatinous. A whole range of materials could be used; one specific embodiment is described in U.S. Pat. No. 5,904,967 to Ezaki; another material classification is organosiloxane polymers having the composition of:

65%—Dimethyl Siloxane
17%—Silica
9%—Thixotrol ST
4%—Polydimethylsiloxane
1%—Decamethyl cyclopentasiloxane
1%—Glycerine
1%—Titanium Dioxide 2. Improved Access Port Referring to FIG. 21, some embodiments of the invention comprise an access port 150 with a layer of self-sealing material 152 as described above, or other self-sealing material known in the arts, such as urethane. The access port 150 provides needle access 154 to flowing blood (in order to perform hemodialysis) without the need to wait for the graft section 102 of the VAS 100 to mature or heal-in after surgery. The port 150 is constructed such that it may be accessed with needles 154 numerous times (preferably at least about approximately 12-15 times—enough for 1-month of hemodialysis). When the needle 154 is removed from the access port 150, the material 152 seals itself to prevent bleeding and hematoma formation. The access port 150 is subcutaneous and accessible via hemodialysis needles 154 through a layer of self-sealing material 152. The access port 150 may be configured to provide increased radio-opacity under either x-ray or ultrasound visualization. Other configurations for an access port are disclosed in U.S. Pat. No. 6,102,884 to Squitieri and U.S. Pat. No. 5,647,855 to Trooskin.

a. Connector Port at with Compressive Material to Seal Needle Tracts

In one embodiment, the access port comprises a layer of a compressed material as described previously, or some other type of self-sealing structure, incorporated into the connector. The compressed material causes the needle tract to close when the needle is removed. The preferred embodiment uses an elastomer, such as silicone or urethane, which is physically compressed when it is placed into the port body.

b. Needle-Activated Check Valve

Figure 36:
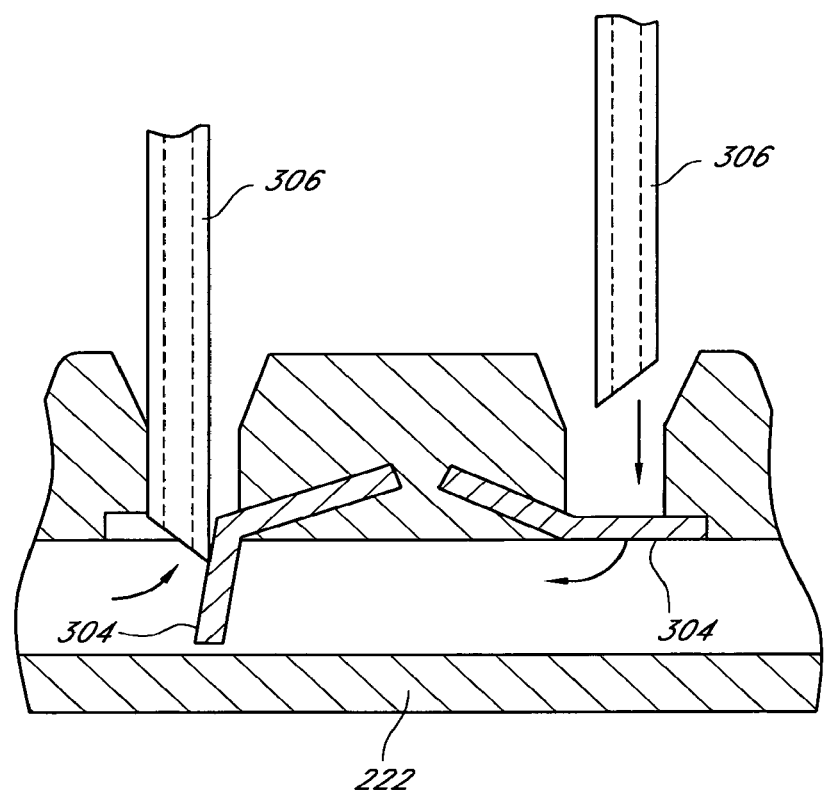
FIG. 36 is a cross-sectional view of a connector with biased flaps for providing access to the blood passageway.

In another embodiment, a check valve is incorporated into the conduit connector and is activated by inserting a needle into the connector, as shown in FIG. 36. A biased flap of material 304, such as silicone or urethane, may be used to provide normally closed opening to the blood passageway that are opened upon insertion of a needle 304 or other access device. Upon removal of the needle 306, the biased flap 304 resumes its bias so that the flap can cover or seal the hole. The connector will preferably incorporate a means to guide the needle or access device into the correct connector location. This may comprise a funnel shape and/or features that may be palpated through the skin to assist the dialysis technician in locating the connector to access it.

Figure 26:
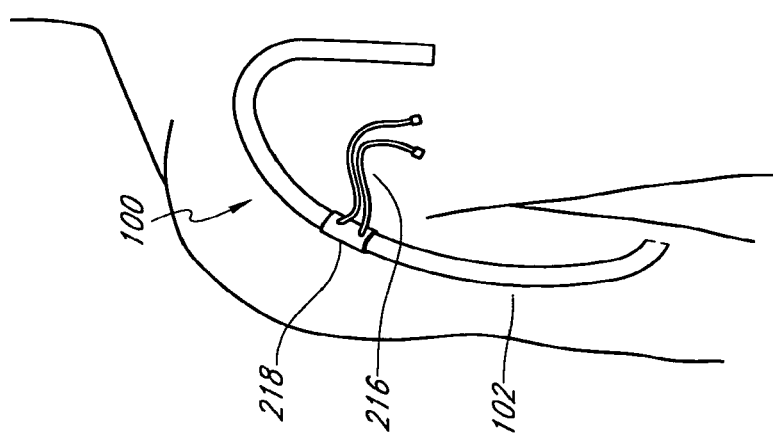
FIG. 26 is a schematic representation of a vascular access system with an attached temporary catheter.

3. Temporary Access of the Vascular Access System a. Temporary (Pull Out or Tear-Away) Catheter "Temporary" refers to a catheter being used short-term (about 90 days or less, but typically about a month or less) and configured to facilitate abandonment or removal after that time. Such a device could be used in the same manner as current hemodialysis catheters except it is expected to be abandoned or removed after limited use. A temporary catheter may be connected or formed with the permanent portion of the VAS so that both can be implanted in a single procedure, but later separated or severed when no longer needed. In some embodiments, as shown in FIG. 26, the temporary catheter 216 protrudes from the skin to eliminate the need to pierce the skin during use. Thus, one advantage of a temporary catheter 216 is that it would allow dialysis to be performed immediately after surgical implantation of the VAS 100 without the severe pain associated with needle sticks immediately following surgery (as is experienced with current instant stick grafts). Another possible advantage of abandoning or removing the catheter after a limited time period is that it will decrease the likelihood of infection, especially risks associated with long-term use of hemodialysis catheters and/or with vascular access extending from out of the skin. More than one temporary catheter may be provided.

In one embodiment, the temporary catheter 216 comprises a conduit with at least one lumen, but preferably at least two lumens, which are attached to the connector 218 of the VAS 100. In other embodiments, the temporary catheter may be attached at other locations of the VAS 100. With a single lumen, infusions or blood draws may be performed from the temporary catheter device, but dialysis is more difficult to perform due to recirculation. With two or more lumens, dialysis may be performed through the temporary catheter while the graft section 102 of the VAS 100 is healing-in (typically less than about one month). Once the graft section 102 is healed-in and the patient is able to dialyze through their VAS 100, the temporary catheter 216 is disabled by removing at least a portion of the temporary catheter device 216. It is desirable to disable the temporary catheter 216 because catheters which exit the skin have a higher long-term infection rate when compared to subcutaneous grafts. The temporary catheter may optionally have a Dacron cuff near the exit site in order to reduce the rate of infection.

i. Seal Using Compressive Material at Junction

Referring to FIGS. 27A and 27B, in one embodiment of the invention, a compressive material 220 is incorporated into the conduit connector 218 and the temporary catheter 216 is attached to the connector 218 at the point of manufacture. The temporary catheter is used for about 90 days or less, but preferably less than about 1 month, and after that time, is removed in a manner similar to removing current hemodialysis catheters—it is pulled out from the site where the catheter exits through the skin. When the catheter 216 is pulled from the connector site, the compressed material 220 in the connector 218 seals the hole where the catheter 216 was removed, as shown in FIG. 27B.

ii. Seal Using Flap at Junction

Alternatively, instead of employing a compressive material to seal off the hole in the connector when the temporary catheter is removed, a biased flap of material, similar to the needle access check valve as depicted in FIG. 36, may be adapted to provide a opening to the blood passageway when engaged to a temporary catheter or other access device. Upon removal of the temporary catheter, the biased flap resumes its bias so that the flap can cover or seal the hole.

iii. Mechanical Valve at Junction

Another alternative embodiment comprises a mechanical valve instead of a flap to seal the hole in the connector when the temporary catheter is removed. One particular example is constructed using a self-closing valve set in the conduit connector or other section of the VAS. The temporary catheter fits into and may inhibit the self-sealing connection feature until removal.

Referring to FIGS. 28A and 28B, the central hub of a connector 222 may be used to house a set of mechanical valves 224, 226. One valve is the outlet 224 while the other is the inlet 226. This embodiment involves creating a pressure differential to move pistons 228, 230 along internal pathways 229, 231 between an open position and closed position, as shown in FIGS. 28A and 28B, respectively. These pistons 228, 230 may be connected to springs 232, 234 for equilibrium positioning. In the resting or closed position depicted in FIG. 28B, the piston heads 228, 230 would be flush with the inside surface 236 of said connector 222 and the piston conduits 233, 235 are out of alignment with inlet and outlet conduits 237, 239. As pressure and/or vacuum is applied from the connected tubing 241, 243, the pistons 228, 230 move from resting position to the open position to align the piston conduits 233, 235 with the inlet and outlet conduits 237, 239 so that may flow commence. When the pressure and/or vacuum is shut off, the pistons 228, 230 return to resting position, inhibiting any flow. In some further embodiments, one or both of the pistons may be configured to protrude into the connector's lumen 245 in order to reduce or eliminate the flow through the middle portion 247 of the connector 222. This may be desirable because it will help prevent or eliminate recirculation of the blood during dialysis (i.e. prevents blood from flowing directly from the outlet port from the temporary catheter and then into the inlet port of the temporary catheter).

iv. Seal with Insert Plug with Positive Locking Stop

Figure 29A:
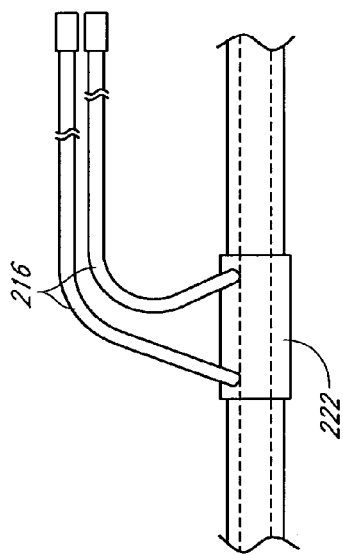
FIGS. 29A to 29C are schematic representations of a temporary catheter with a full-length plug.
Figure 29C:
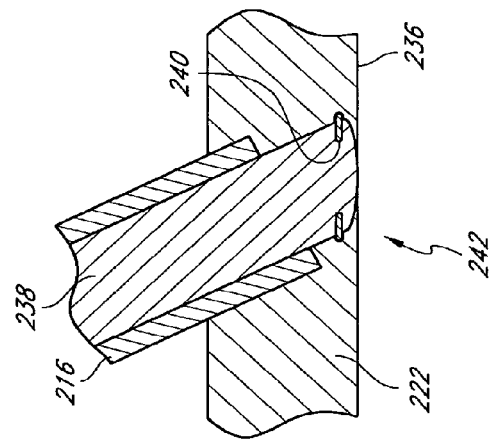
Figure 29B:
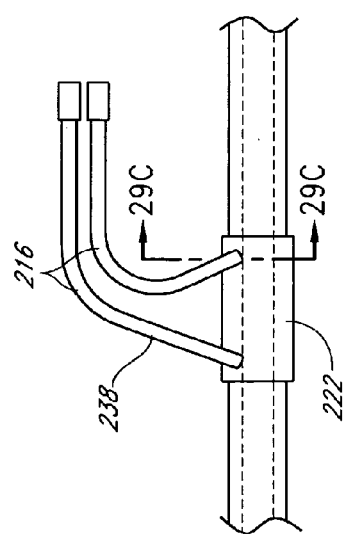
Figure 31A:
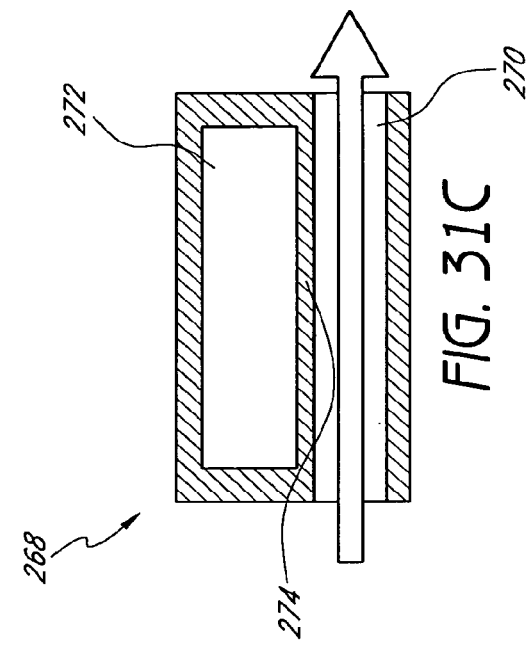
FIGS. 31A to 31D are schematic longitudinal and axial cross-sectional views of one embodiment of the invention comprising a dual-compartment flow control section of a vascular access system in high-flow and low-flow states, respectively.
Figure 31B:
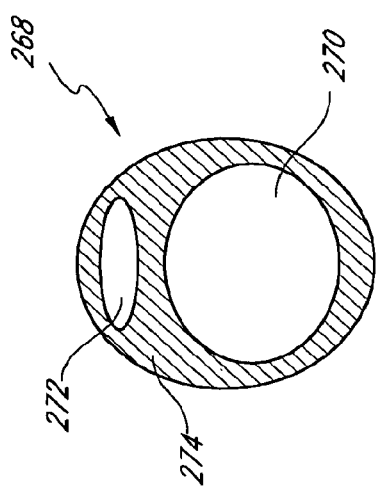
Figure 31C:
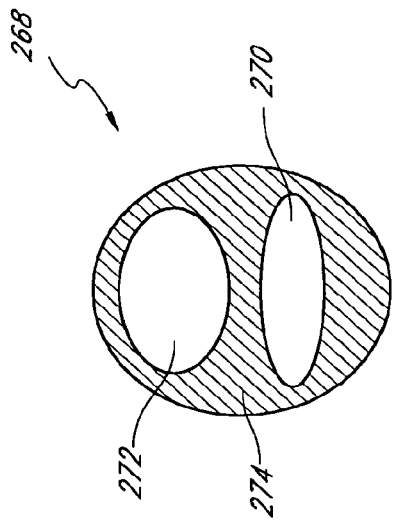
Figure 31D:
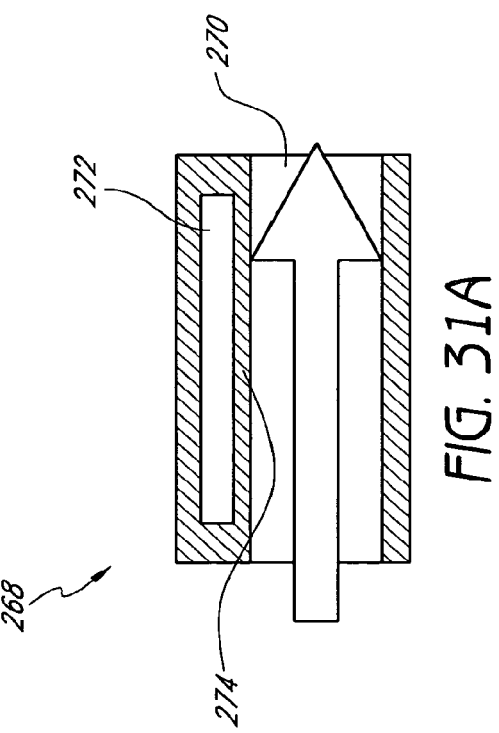

In another alternative embodiment, the temporary catheter may be completely separated from the connector. A plug is inserted through the temporary catheter and locks into place in order to seal the hole(s) in the connector.

b. Abandoned Catheter Section i. Seal Through Lumen Using Plug/Mandrel with Positive Locking Stop Referring to FIGS. 29A to 29C, in one embodiment, a plug 238 is inserted through the temporary catheter 216 and locked into place in order to seal the hole in the connector 222. The plug 238 may be configured such that it is generally flush with the lumen 236 of the connector 222, or where the plug minimizes sharp edges, bumps, holes or other surface irregularities that would cause turbulence as this could lead to thrombus buildup and eventual device occlusion. In this embodiment, the subcutaneous portion of the temporary catheter 216 remains in place and therefore a portion of the plug 238 may stay in the catheter 216. In some embodiments, as shown in FIG. 29C, one or more complementary detents/protrusions 240, 242 may be provided to further control the relative position of the plug 238 with the lumenal surface 236 of the connector 222.

ii. Inject Sealing Compound into Lumen

In one embodiment of the invention, a material that has the ability to solidify may be used to plug the lumens. There are several materials that may be used, such as cements, epoxies, and polymers. A preferred material is Onyx® from Micro Therapeutics, Inc. Onyx® is a liquid embolization material that may be injected through the lumens under fluoroscopic or other type of visualization. When the material comes in contact with the flowing blood, it will form a smooth surface and become solid through a precipitation reaction (e.g. DMSO is exchanged with the water in blood). More specifically, Onyx® is a liquid mixture of ethylene vinyl alcohol copolymer (EVOH) dissolved in dimethyl sulfoxide (DMSO). Micronized tantalum powder is suspended in the liquid polymer/DMSO mixture to provide fluoroscopic visualization. The Onyx material is delivered in a liquid phase to fill the catheter lumens under fluoroscopic control. Upon contact with blood (or body fluids) the solvent (DMSO) rapidly diffuses away, causing in-situ precipitation of a soft radiopaque polymeric material. After the lumen is filled and the filling material has solidified, the temporary catheter may be cut so it lies subcutaneously. (Clinical Review of MTI, Onyx® Liquid Embolization System, available at http://www.fda.gov/ohrms/dockets/ac/03/briefing/3975b1-02-clinical-review.pdf, accessed Aug. 29, 2005).

iii. Plug Lumen at Proximal End Only

In another embodiment, the proximal end of the temporary catheter 216 is sealed using a plug, clamp, winding, suture or other method and the temporary catheter 216 is cut subcutaneously. The temporary catheter 216 may be sealed then cut, or cut then sealed. The disadvantage of this method is that there is a chance of producing turbulence where the temporary catheter ends inside the connector because there would be an abrupt transition and a blind end where blood stasis will occur.

In particular one embodiment, depicted in FIG. 30A, the temporary catheter 216 and connector 2 form a complementary lock/latch mechanism, whereby the end 244 of the temporary catheter 216 comprises a hard material, either metal or plastic, and a recess 246 containing a biased-split ring 248, and is capable of interfacing with a coupling lumen 252 in the wall 254 of the conduit connector. As shown in FIG. 30B, the coupling lumen 252 is configured with a complementary groove 250 whereby when the temporary catheter 216 is fully inserted into the coupling lumen 252, the biased-split ring 248 can snap into the groove 250 to lock the temporary catheter 216 into the coupling lumen 252 on the conduit connector. In an alternative embodiment, the recess and biased-spit ring may be positioned in the coupling lumen while the end 244 of the temporary catheter 216 has a complementary groove. One of skill in the art will understand that any of a variety of other securing structures may also be used, including but not limited to biased projecting prongs and threaded rotation interfaces.

Once the temporary catheter 216 is no longer needed, the temporary catheter 216 may be plugged or filled, and severed about its proximal end 244. By severing the temporary catheter 216, the amount of foreign body remaining in the patient is reduced, which in turn may reduce the risk of infection, immune system response, and/or cosmetic effect.

Referring back to FIG. 30B, a plug 256 with an insertion stop 258 and one or more ramped edges 260 along its surface is inserted into the lumen 262 of the temporary catheter 216. The ramped edges 260 of the plug 256 provide resistance to backout for the plug 256 while the insertion stop 258 allows the plug 256 to seat in the end 244 of the temporary catheter 216 without protruding excessively past the wall 254 of the connector. The plug 256 is inserted into the temporary catheter 216 using a catheter cutter 264 with a retractable blade 266. The catheter cutter 264 is used to push the plug 256 into the catheter lumen 262. Once the plug 256 is in place, the retractable blade 266 is extended from the catheter cutter 264 and the catheter cutter 264 is rotated or otherwise manipulated to sever at least a portion of the temporary catheter 216 from its end 244. The retractable blade 266 is retracted and the separated portion of the temporary catheter 216 is removed from the patient along with the catheter cutter 264. The end 244 of the temporary catheter 216 and plug 256 remain in the coupling lumen 252 of the wall 254 of the connector and seal it from blood leakage.

c. Implantation of Temporary Access

In one embodiment for implanting the VAS with a temporary access structure, the pathway for the catheter section of the VAS is tunneled first, the pathway for the pre-connected graft section of the VAS is tunneled next, followed preferably by the tunneling of a pathway from the intermediate access site to a temporary catheter exit site. It is preferable that the temporary catheter be located at a tunneled exit site rather than project directly out of the intermediate access site where the catheter section is attached to the graft section, in order to reduce the risk of infection of the main VAS assembly. By increasing the distance between the connector to the skin site where the temporary catheter exits the body, infection of the connector is reduced. After the temporary catheter is tunneled from the chest to the connector, the catheter is locked or latched into the connector, as described in embodiments disclosed above. The temporary catheter may also be tunneled from the connector to the exit site.

D. Flow Control

Typically, when using an AV shunt for hemodialysis access, the blood is directly taken from an artery and shunted to a vein. The flow through the shunt needs to be sufficiently high so that there is more blood flow in the shunt than is required by the dialysis circuit, otherwise recirculation of already-dialyzed blood will occur in the system, reducing dialysis efficiency. Thus, for dialysis, high flow in the shunt is desirable. On the other hand, high flow can be detrimental to the patient. The shunted blood is not available for perfusing the body tissue. The body will try to compensate for the reduced tissue perfusion by increasing the cardiac output. This creates in an increased workload on the heart, which can result in high-output heart failure. The shunt can also result in insufficient flow below the point where the blood exits the artery in the shunt, thereby under-perfusing the tissue below that point (steal syndrome). Ideally, flow through the shunt should be controlled to have high flow during dialysis and low flow between dialysis. One way of accomplishing this is to build a shunt that can be manipulated to provide high flow rates during dialysis and then low flow between dialysis.

Referring to FIGS. 31A to 31D, in one embodiment, the VAS contains at least one flow control section 268 comprising a dual-compartment deformable tubing. One compartment is the blood path 270 for the VAS, while the other acts as a distensible reservoir 272 for fluid. The reservoir 272 shares a compliant common wall 274 with the blood path 270 of the VAS. When the reservoir 272 is distended, the compliant common wall 274 is able to compress the blood path 270 to a reduced cross-sectional area, thereby reducing blood flow through the blood path 270. Some degree of blood flow through the blood path 270 is generally preferred at all times to maintain patency and to reduce the risk of thrombosis. To use the flow control section 268, fluid is injected into the reservoir 272 between dialysis procedures, which restricts the blood flow between sessions. At the time of dialysis, fluid is withdrawn from the reservoir 272, which allows the blood flow through the blood path 270 to increase.

In an alternate embodiment of the invention, depicted in FIGS. 32A and 32B, multi-lumen tubing 276 is provided wherein one lumen 278 is shut off between dialysis but two or more lumens 278, 280 are available during dialysis. This tubing 276 may be formed by manufacturing the tubing 276 with a lumen 278 biased to the reduced configuration, but can be expanded to an enlarged position by the increased flow and/or pressure provided during hemodialysis. In another alternative embodiment, flow control may be achieved by a mechanical clamp integrated with the VAS that is actuatable through the skin and is able to at least partially compress the blood path to reduce flow through the VAS when dialysis is not being performed.

E. Flow Monitoring

In one embodiment of the invention, the VAS further comprises a flow sensor mounted in the device, typically in the catheter section. A flow sensor allows the dialysis unit to directly determine the flow rate in the VAS and verify that it is sufficient to perform routine dialysis. For example, if flow through the VAS is too low, dialysis will occur with a large amount of recirculation in the system, resulting in inadequate dialysis. Real-time detection of reduced flow during the dialysis will also provide an early indication of blockage in the graft and provide the opportunity to take preventative action to prevent the system from shutting down. There are a variety of methods known in the art by which blood flow can be measured. Ideally, the measurement should be non-invasive which would mean some sort of imbedded sensor which can be interrogated by a measuring device using electromagnetic signal from the device. This is done frequently with pacemakers and implanted electronic devices.

Figure 33:
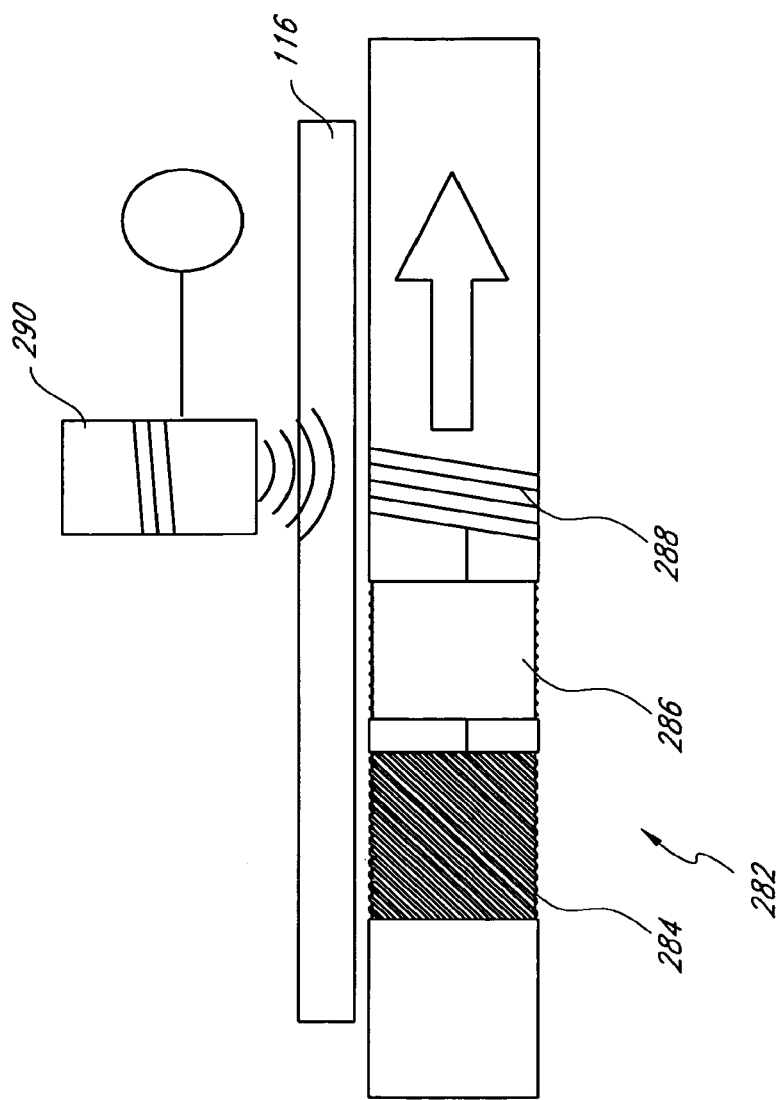
FIG. 33 is a schematic view of one embodiment of the invention comprising a flow sensor assembly.

One embodiment of a flow sensor is depicted in FIG. 33. The flow sensor 282 may be housed in part of the conduit connector or another region of the VAS. The sensing element 284 of the flow sensor 282 may be based upon any of a variety of methods known in the art, which include but are not limited to thermal, heat dissipation as a function of flow, thermal rise for a specific heat input, pressure drop across a known distance, along a length of the device, across a metering orifice, impact pressure, wall stress from fluid shear, magnetic flow, Doppler flow, a sensor for saline injection, or any a combination thereof. Those with skill in the art will understand that many flow sensor designs may also be used.

The flow sensing element 284 is attached to the various additional electronics 286 that may also be located in the wall of the VAS, or in a separate housing attachable to the wall of the VAS. This in turn is connected to an antenna 288 imbedded in the wall of the catheter or in the separate housing. The antenna 288 can be used to transmit data from the flow sensor 282 to an external receiver 290, but also preferably to power the device from and external source. In other embodiments, a wired connection that is accessible from outside the body may be provided from the flow sensor, in lieu of or in additional to wireless transmission between the components.

The measurement of blood flow may be performed directly, or more typically, indirectly. In a preferred embodiment of the invention, the pressure differential between two (or more) locations in the catheter are measured and the flow is calculated. The flow in the catheter is approximately given by Poiseuille's Equation:

$$Q = \Delta P \pi r^4 / 8 \eta l$$

Where Q is flow rate, ΔP is the pressure differential, r is the radius of the catheter lumen, η is the viscosity, and l is the distance between the pressure measurement points. The equation shows that the flow rate is very sensitive to the radius of the catheter. However, the catheter is relatively non-thrombogenic compared to the graft and therefore one may approximate the flow rate by assuming that the catheter remains at a constant radius. In the preferred embodiment, the flow monitoring components of the VAS comprise an external component and an internal component.

In one embodiment, the external component comprises a power supply, a transmitter, a receiver, a signal processor and a flow readout. The VAS flow monitor may be powered by standard wall outlet electricity or by battery. If standard wall outlet power is used, the power supply regulates the voltage to match the requirements of the other components. The power supply may be used to power both the external device and the internal device. The transmitter comprises an antenna and a tuned circuit that transmits a radio frequency (RF) signal. The RF signal is tuned for optimal coupling to the implanted device in order to transfer power to the implanted device. A receiver is also contained in the external component. The receiver receives the flow signals from the implanted portion of the flow monitor. This antenna is tuned for optimal reception with the output signal of the implanted device. Preferably, the transmitter and receiver would use the same antenna. The signal processor takes the signal from the receiver, analyzes the signals to determine the flow rate, and converts the flow rate into an electronic format so the flow can be displayed by the flow readout. Electronic circuits are well known for converting electronic signals to a format that can be readily displayed. More details of the signal analysis are given below. In other embodiments of the invention, the flow rate information is not converted to an electronic format and instead is displayed on a calibrated analog display. Thus, the flow readout may comprise a standard digital or analog readout that provides a display of the flow value.

The internal or implanted component of the flow monitor comprises a receiver, a flow sensing unit, a signal processor and a transmitter. The receiver receives the RF signal from the external device and uses it to provide power to operate the other components in the implanted device. The preferred shape of the antenna is a coil embedded into the catheter wall. The preferred embodiment of the flow sensing unit comprises a series of individual pressure transducers embedded into the wall of the catheter. In some embodiments, the transducers are embedded into the catheter rather than the graft (ePTFE) because the catheter typically is made of a material (e.g. silicone) that is considerable less thrombogenic than the graft, thus allowing one to assume that the catheter diameter remains constant. One group of pressure transducers are separated by a known distance from another group of transducers by a known distance in order to measure the pressure drop from one portion of the catheter to another portion of the catheter. In one embodiment, each group of pressure transducers comprises one transducer, but in other embodiments, one or more group comprise at least two transducer each, spaced along the circumference, in order to allow averaging for more accurate measurements. Pressure transducer groups with multiple transducers about a circumference may compensate for possible localized pressure variations due to bends in the catheter and other local bias factors.

Although various types of pressure transducers are contemplated for the invention, one of the most common is the strain-gauge transducer. The conversion of pressure into an electrical signal is achieved by the physical deformation of strain gauges which are bonded into the diaphragm of the pressure transducer and wired into a Wheatstone bridge configuration. Pressure applied to the pressure transducer produces a deflection of the diaphragm which introduces strain to the gauges. The strain will produce an electrical resistance change proportional to the pressure. The strain gauges may be covered with a thin, flexible biocompatible material such as silicone or urethane and be positioned on the inside surface of the catheter for maximum sensitivity.

The signal processor for the implantable component takes the signals from each one of the transducers and, in the preferred embodiment, it amplifies, encodes, and multiplexes each signal for transmission by the transmitter so the external component can decode and identify the readings from each of the individual transducers. The electronics may be preferably designed to keep all of the time-dependent information (the pulse waveform) of the signals for analysis by the external system.

In another embodiment, the pressure monitoring system may be used to assess for possible clot formation in the catheter using the temporal information of the pulse waveform to help determine flow rate. For example, if the graft section begins to clot while the catheter remains patent, the absolute pressure in the catheter will drop, the pressure differential between the transducers will also drop, and the waveform shape will change to a less resistive shape (pressure waveform looks more like waveform of the central venous system). The external component of the flow monitoring system will analyze this information and determine the flow rate. On the other hand, if the catheter begins to form clot and the flow slows, the waveform shape will continuously become more resistive with decreased flow. In addition, the pressure differential will increase and the absolute pressure will decrease as the flow decreases. This will occur until the pressure differential reaches a threshold, at this point both pressures will drop with decreased flow. The transmitter is driven by the electronics and preferable uses the receiver antenna to transmit the RF signals to the external device.

While this invention has been particularly shown and described with references to embodiments thereof, it will be understood by those skilled in the art that the various changes in form and details may be made therein without departing from the scope of the invention. For all of the embodiments described above, the steps of the methods need not be performed sequentially. Furthermore, any references above to either orientation or direction are intended only for the convenience of description and are not intended to limit the scope of the invention to any particular orientation or direction.

What is claimed is:

1. An apparatus for providing needle access to a blood pathway comprising:
   a first fluid conduit comprising a graft conduit configured for attachment to an artery at a proximal end of the first fluid conduit;
   a second fluid conduit separate from the first fluid conduit comprising a catheter conduit configured for insertion in a vein at a distal end of the second fluid conduit, the distal end of the second fluid conduit being sized to permit collateral flow of blood around the second fluid conduit and through the vein in which the second fluid conduit is inserted;
   a connector element having an internal passageway in fluid communication with the first and second fluid conduits to form a blood pathway, the first end of the connector element being connected to a distal end of the first fluid conduit and a second end being connected to a proximal end of the second fluid conduit; and a self-sealing element comprising a wall structure forming, at least in part, a portion of a wall of the second fluid conduit or the connector element, the wall structure being formed of a tubular material that can be punctured by a needle to permit needle access to the blood pathway and that re-seals upon withdrawal of the needle, wherein the connector element has a transition zone occupying at least a portion of the internal passageway therein, the transition zone being configured to reduce turbulent or non-laminar flow in the blood pathway between the first and second fluid conduits.

2. The apparatus for providing needle access to a blood pathway as in claim 1, wherein the tubular material is selected from the group consisting of: material subject to compressive stress; material having a porous structure enhancing microthrombosis; low durometer materials, thixotropic materials; gelatinous materials; and combinations thereof.

3. The apparatus for providing needle access to a blood pathway as in claim 1, wherein the tubular material comprises material subject to compressive stress.

4. The apparatus for providing needle access to a blood pathway as in claim 1, wherein the tubular material comprises at least two layers subject to compressive stress of different orientations.

5. The apparatus for providing needle access to a blood pathway as in claim 1, wherein the tubular material comprises material having a porous structure.

6. The apparatus for providing needle access to a blood pathway as in claim 1, wherein the tubular material comprises gelatinous material.

7. The apparatus for providing needle access to a blood pathway as in claim 1, wherein the connector element is integrally formed with the second fluid conduit.

8. The apparatus for providing needle access to a blood pathway as in claim 1, wherein the connector element is integrally formed with the first fluid conduit.

9. The apparatus for providing needle access to a blood pathway as in claim 1, further comprising a strain relief tube about the second fluid conduit, the strain relief tube having a first end and a second end, the second end comprising two or more flexural sections and two or more separations between the flexural sections.

10. The apparatus for providing needle access to a blood pathway as in claim 1, further comprising a means for controlling blood flow rate through the blood pathway.

11. The apparatus for providing needle access to a blood pathway as in claim 1, further comprising a means for monitoring blood flow rate through the blood pathway.

12. The apparatus for providing needle access to a blood pathway as in claim 1, wherein the connector element further comprises one or more securing structures for securing the connector element to the first and second fluid conduits.

13. The apparatus for providing needle access to a blood pathway as in claim 12, wherein the securing structure is selected from the group consisting of a clamshell assembly, a tension clips, a collet securing device, a compression ring/collar, one or more barb-like protrusions, and combinations thereof.

14. A vascular access system for hemodialysis comprising:
a catheter conduit having a proximal end and a distal end with a lumen therethrough, wherein the distal end is configured for insertion in a vein and sized to permit collateral flow of blood around a distal end of the catheter conduit and through the vein in which the catheter conduit is inserted;
a connector element having a fluid passageway therethrough, wherein the connector element comprises a first end configured for connection to a distal end of a graft conduit that is separate from the catheter conduit and a second end connected to the proximal end of the catheter conduit; and
a self-sealing element integrally formed with the catheter conduit or connector element, the self-sealing element comprising a wall structure formed of a self-sealing material suitable for puncture by a needle to permit needle access to the fluid passageway and configured to re-seal upon withdrawal of said needle,
wherein the connector element has a different internal diameter at its first and second ends and is configured to provide a smooth transition in the fluid passageway between the proximal end of the catheter conduit and the distal end of the graft conduit.

15. The vascular access system as in claim 14, further comprising a graft conduit connected to the first end of the connector element.

16. The vascular access system as in claim 14, wherein the connector element is integrally formed with the catheter conduit.

17. The vascular access system as in claim 14, wherein the connector element further comprises one or more securing structures for securing the catheter conduit and graft conduit to the connector element.

18. The vascular access system as in claim 17, wherein the securing structure is selected from the group consisting of a clamshell assembly, a tension clips, a collet securing device, a compression ring/collar, one or more barb-like protrusions, and combinations thereof.

19. The vascular access system as in claim 17, wherein the securing structure comprises a clamshell assembly having a pair of complementary connecting structures configured to secure the conduit to the connector element.

20. A vascular access system for hemodialysis comprising:
a graft conduit having a proximal end and a distal end, wherein the proximal end is configured for anastomosis to an artery;
a connector element having a fluid passageway therethrough, wherein the connector element comprises a first end connected to the distal end of the graft conduit and a second end configured for connection to a proximal end of a catheter conduit that is separate from the graft conduit; and
a self-sealing element integrally formed with the graft conduit or connector element, the self-sealing element comprising a wall structure formed of a self-sealing material suitable for puncture by a needle to permit needle access to the fluid passageway and configured to re-seal upon withdrawal of said needle,
wherein the connector element has a different internal diameter at its first and second ends and is configured to provide a smooth transition in the fluid passageway between the distal end of the graft conduit and the proximal end of the catheter conduit.

* * * * *